US010842812B2

(12) United States Patent
Mootha et al.

(10) Patent No.: US 10,842,812 B2
(45) Date of Patent: Nov. 24, 2020

(54) COMPOSITIONS AND METHODS THAT PROMOTE HYPOXIA OR THE HYPOXIA RESPONSE FOR TREATMENT AND PREVENTION OF MITOCHONDRIAL DYSFUNCTION AND OXIDATIVE STRESS DISORDERS

(71) Applicants: THE GENERAL HOSPITAL CORPORATION, Boston, MA (US); Massachusetts Institute of Technology, Cambridge, MA (US)

(72) Inventors: Vamsi K. Mootha, Boston, MA (US); Isha Jain, Cambridge, MA (US); Warren M. Zapol, Cambridge, MA (US); Luca Zazzeron, Boston, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/751,585

(22) PCT Filed: Aug. 12, 2016

(86) PCT No.: PCT/US2016/046791
§ 371 (c)(1),
(2) Date: Feb. 9, 2018

(87) PCT Pub. No.: WO2017/027810
PCT Pub. Date: Feb. 16, 2017

(65) Prior Publication Data
US 2019/0015444 A1 Jan. 17, 2019

Related U.S. Application Data

(60) Provisional application No. 62/268,213, filed on Dec. 16, 2015, provisional application No. 62/204,285, filed on Aug. 12, 2015.

(51) Int. Cl.
| | |
|---|---|
| A61K 33/00 | (2006.01) |
| A61P 25/14 | (2006.01) |
| G01N 33/50 | (2006.01) |
| A61K 31/198 | (2006.01) |
| A61K 31/472 | (2006.01) |
| A61K 31/225 | (2006.01) |
| A61K 31/19 | (2006.01) |
| A61K 31/4745 | (2006.01) |
| A61K 31/194 | (2006.01) |
| A61K 31/44 | (2006.01) |
| A61K 31/4704 | (2006.01) |
| C07K 14/00 | (2006.01) |
| A61K 31/5377 | (2006.01) |
| A61K 9/00 | (2006.01) |
| C12N 15/11 | (2006.01) |

(52) U.S. Cl.
CPC .............. *A61K 33/00* (2013.01); *A61K 9/007* (2013.01); *A61K 31/19* (2013.01); *A61K 31/194* (2013.01); *A61K 31/198* (2013.01); *A61K 31/225* (2013.01); *A61K 31/44* (2013.01); *A61K 31/472* (2013.01); *A61K 31/4704* (2013.01); *A61K 31/4745* (2013.01); *A61K 31/5377* (2013.01); *A61P 25/14* (2018.01); *C07K 14/00* (2013.01); *C12N 15/11* (2013.01); *G01N 33/50* (2013.01); *G01N 33/5008* (2013.01); *G01N 33/5041* (2013.01); *G01N 33/5079* (2013.01); *C12N 2310/20* (2017.05); *G01N 2800/04* (2013.01); *G01N 2800/7009* (2013.01); *G01N 2800/7038* (2013.01); *G01N 2800/7095* (2013.01)

(58) Field of Classification Search
None
See application file for complete search history.

(56) References Cited

U.S. PATENT DOCUMENTS

| | | |
|---|---|---|
| 2003/0176349 A1 | 9/2003 | Semenza |
| 2012/0282353 A1 | 11/2012 | Roth et al. |
| 2013/0123341 A1 | 5/2013 | Parker, Jr. |
| 2013/0288328 A1 | 10/2013 | Dunning et al. |
| 2014/0294842 A1 | 10/2014 | Maxwell et al. |
| 2016/0038710 A1 | 2/2016 | Zapol et al. |

FOREIGN PATENT DOCUMENTS

| | | |
|---|---|---|
| WO | WO 1997/03631 | 2/1997 |
| WO | WO 2009/143268 | 11/2009 |
| WO | WO 2011/051357 | 5/2011 |

OTHER PUBLICATIONS

Zeviani et al. Blood 2004, vol. 127, pp. 2153-2172.*
Michiels, "Physiological and Pathological Responses to Hypoxia," American Journal of Pathology 164(6): 1875-1882 (Jun. 6, 2004).
Buckley et al., "Targeting the von Hippel-Lindau E3 Ubiquitin Ligase Using Small Molecules to Disrupt the VHUHIF-1a Interaction," Journal of the American Chemical Society 134: 4465-4468 (Feb. 27, 2012).

(Continued)

*Primary Examiner* — Tracy Vivlemore
(74) *Attorney, Agent, or Firm* — Fish & Richardson P.C.

(57) ABSTRACT

Methods of promoting hypoxia or the hypoxia response for the treatment or prevention of mitochondrial dysfunction and oxidative stress disorders are described. Methods for screening for targets of mitochondrial dysfunction and oxidative stress disorders are also described.

35 Claims, 28 Drawing Sheets

Specification includes a Sequence Listing.

(56) References Cited

OTHER PUBLICATIONS

Roberts et al "Inhaled Nitric Oxide and Persistent Pulmonary Hypertension of the Newborn," The New England Journal of Medicine 336(9): 605-610 (Feb. 27, 1997).
Advanced Life Support Group, "Oxygen Therapy Guidelines," Safe Transfer and Retrieval: The Practical Approach, Second Edition. Blackwell Publishing Ltd. Jan. 28, 2008; pp. 197-200; DOI: 10.1002/9780470757437.
Young et al., "Response Time of Pulse Oximeters Assessed Using Acute Decompression," Anesthesia Analogs 74:189-95 (Feb. 1992).
Rossaint et al "Inhaled Nitric Oxide for the Adult Respiratory Distress Syndrome," The New England Journal of Medicine 328(6): 399-405 (Feb. 11, 1993).
International Search Report and Written Opinion dated Feb. 1, 2017 in international application No. PCT/US2016/046791, 25 pgs.
Jain et al., "Leigh Syndrome Mouse Model Can Be Rescued by Interventions that Normalize Brain Hyperoxia, but Not HIF Activation," Cell Metabolism, Oct. 2019, 30:1-9, 13 pages.
EP Extended European Search Report in EP Application No. EP16835981.8, dated Aug. 22, 2019.
Haas et al., "Mitochondrial Disease: A Practical Approach for Primary Care Physicians," Pediatrics, 2007, 120: 1326-33.
International Preliminary Report on Patentability in International Application No. PCT/US2016/046791, dated Feb. 13, 2018, 16 pages.
Parikh et al., "A Modern Approach to the Treatment of Mitochondrial Disease," Curr Treat Options Neurol, 2009, 11:414-30.
Vafai and Mootha., "Mitochondrial disorders as windows into an ancient organelle," Nature, 2012, 491:374-83.
EP Partial Supplementary European Search report in EP Application No. EP16835981.8, dated May 20, 2019, 20 pages.
Jain et al, "Hypobaric Hypoxia Imbalances Mitochondrial Dynamics in Rat Brain Hippocampus," Neurology Research International, 2015, pp. 1-12.

* cited by examiner

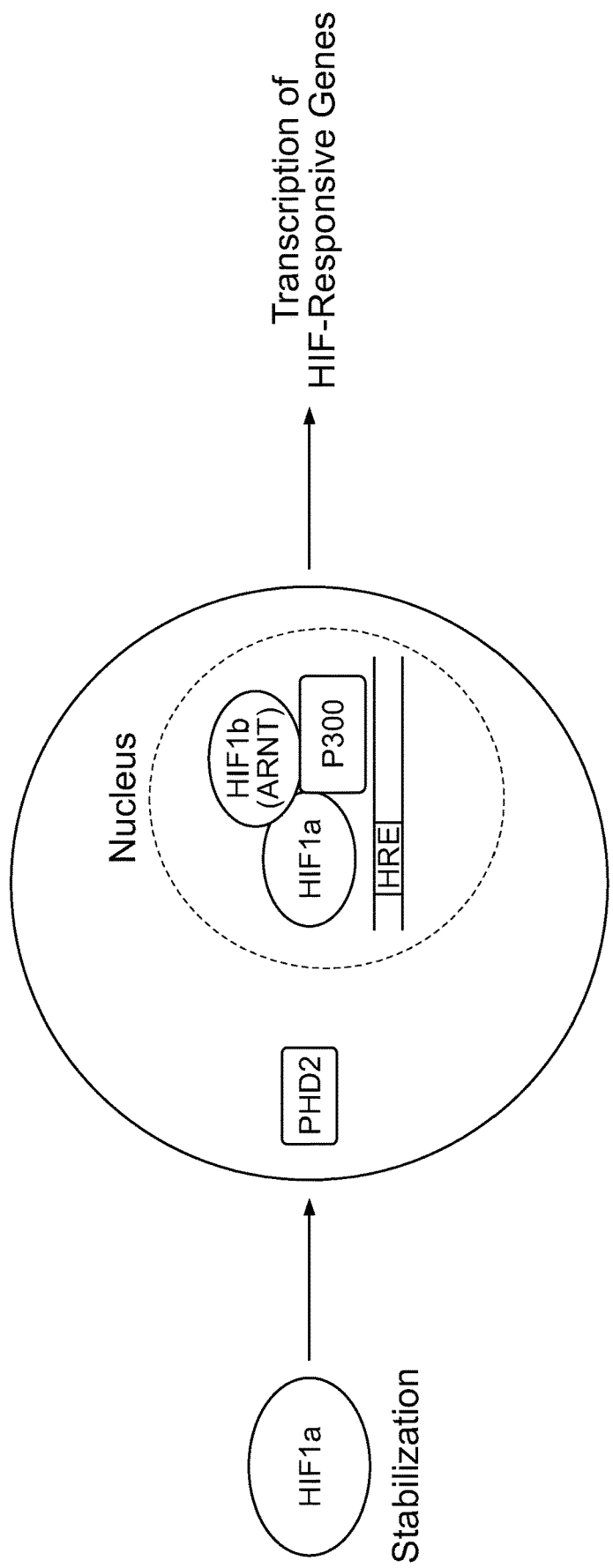
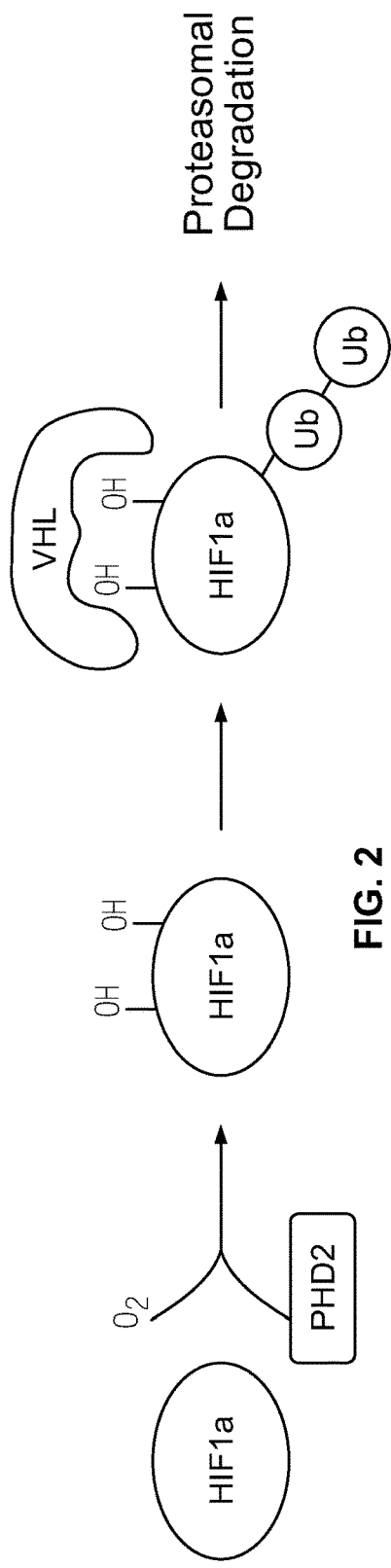
FIG. 1
FIG. 2

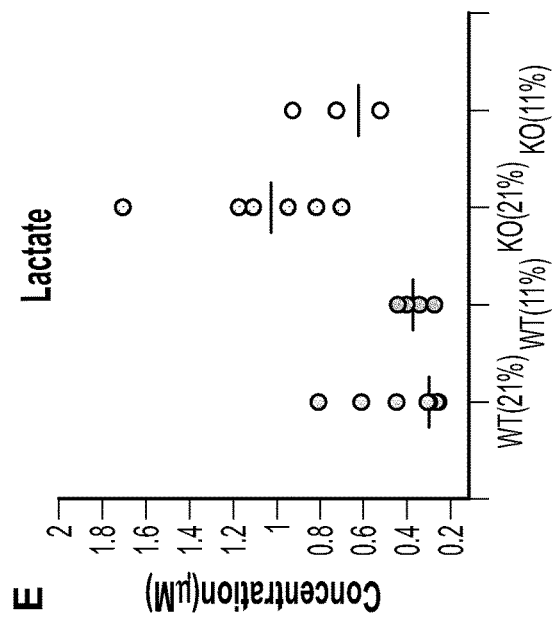
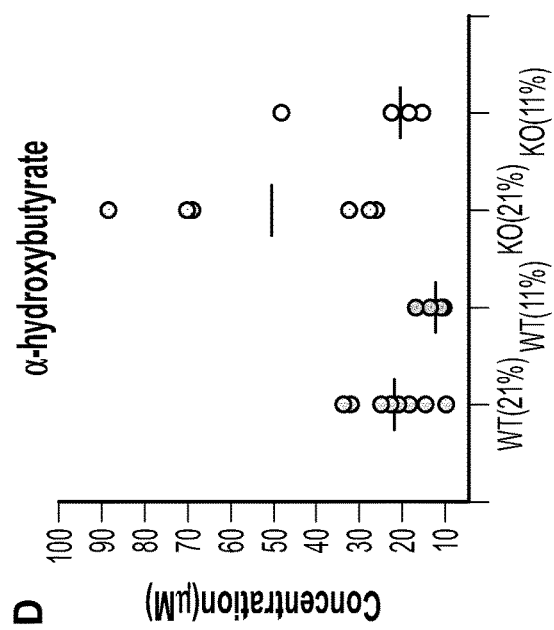
FIG. 19-2
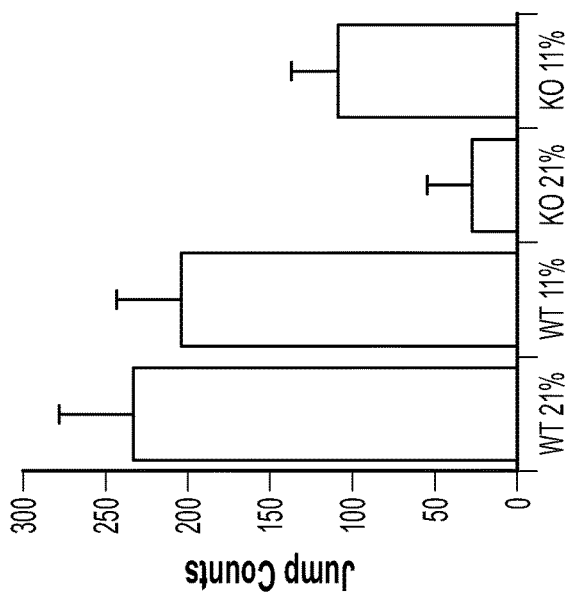
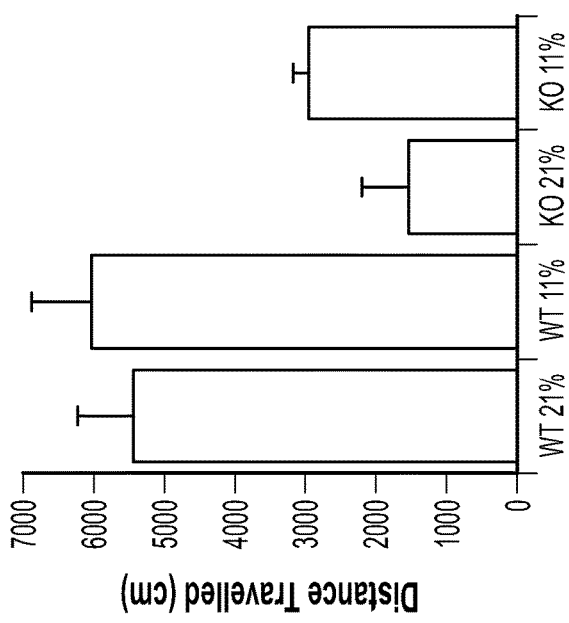
FIG. 20

A

B

SEQUENCE LISTING

```
<160> NUMBER OF SEQ ID NOS: 5

<210> SEQ ID NO 1
<211> LENGTH: 20
<212> TYPE: DNA
<213> ORGANISM: Homo sapiens

<400> SEQUENCE: 1
agtacctggc agtgtgatat                                        20

<210> SEQ ID NO 2
<211> LENGTH: 20
<212> TYPE: DNA
<213> ORGANISM: Homo sapiens

<400> SEQUENCE: 2
caggtcgctc tacgaagatc                                        20

<210> SEQ ID NO 3
<211> LENGTH: 20
<212> TYPE: DNA
<213> ORGANISM: Homo sapiens

<400> SEQUENCE: 3
cgcgcgtcgt gctgcccgta                                        20

<210> SEQ ID NO 4
<211> LENGTH: 20
<212> TYPE: DNA
<213> ORGANISM: Homo sapiens

<400> SEQUENCE: 4
gtgccatctc tcaatgttga                                        20
```

```
<210> SEQ ID NO 5
<211> LENGTH: 20
<212> TYPE: DNA
<213> ORGANISM: Homo sapiens

<400> SEQUENCE: 5
tgtccgtcaa cattgagaga                                              20
```

COMPOSITIONS AND METHODS THAT PROMOTE HYPOXIA OR THE HYPOXIA RESPONSE FOR TREATMENT AND PREVENTION OF MITOCHONDRIAL DYSFUNCTION AND OXIDATIVE STRESS DISORDERS

CROSS REFERENCE TO RELATED APPLICATIONS

This application claims the benefit of U.S. Provisional Application No. 62/204,285 filed Aug. 12, 2015 and U.S. Provisional Application No. 62/268,213 filed Dec. 16, 2015, the contents of both of which are incorporated herein by reference in their entireties.

STATEMENT REGARDING FEDERALLY SPONSORED RESEARCH

This invention was made with Government support under Grant No. DE-FG02-97ER25308 awarded by the Department of Energy. The Government has certain rights in this invention.

TECHNICAL FIELD

The present invention relates generally to compositions and methods that promote hypoxia or the hypoxia response for treating or preventing mitochondrial dysfunction and oxidative stress disorders.

BACKGROUND

There is growing evidence that mitochondrial dysfunction is associated with a broad range of human diseases. Virtually all common, age-associated disorders, including type 2 diabetes, neurodegeneration, and sarcopenia, are accompanied with a quantitative decline in the activity of the mitochondrial respiratory chain (Vafai et al., Nature, 491:374-83 (2012); Parikh et al., Curr Treat Options Neurol. 11:414-30 (2009). Monogenic disorders of the mitochondrial respiratory chain represent the largest class of inborn errors of metabolism. To date, lesions in over 150 genes, encoded by the nuclear or mitochondrial (mtDNA) genome, have been identified as disease-causing. Mutations in these genes lead to a biochemical deficiency of one or more of the respiratory chain complexes, leading to either tissue-specific or multi-systemic disease. Management of these disorders remains incredibly challenging, owing to the remarkable genetic heterogeneity and pleiotropy. Current treatments are limited to ad hoc administration of vitamins and co-factors, none of which have proven efficacy. A more general and effective therapeutic is needed for the treatment of mitochondrial dysfunction.

A major challenge in targeting mitochondrial disease lies in the fact that the organelle plays diverse roles in cellular metabolism. Classically, mitochondrial disease pathology is thought to arise from an energy supply-demand imbalance. However, redox state, nucleotide biosynthesis, ROS homeostasis, regulation of apoptosis, calcium signaling and fatty acid oxidation may be impaired in disease states. It is notable that mitochondrial disorders can be highly tissue-specific, and episodic (Haas et al., Pediatrics. 120, 1326-33 (2007)). Individuals with identical genetic lesions can follow completely distinct clinical trajectories. Such observations suggest that existing cellular pathways may buffer against lesions in unaffected tissues.

SUMMARY

A genome-wide clustered regularly interspaced short palindrome repeats (CRISPR) screen was performed to spotlight endogenous pathways that buffer against mitochondrial respiratory chain dysfunction. The screen identified Von Hippel Landau (VHL)-inhibition and thus the hypoxia response, as a suppressor of mitochondrial disease. It was shown that genetic or small molecule activation of the hypoxia inducible transcription factors (HIF) rescued cellular growth defects caused by respiratory chain deficiency. The small molecule FG-4592 rescued the disease state in a variety of cell types and at multiple steps (complexes I, III, V) of the electron transport chain, demonstrating the broad applicability of this therapeutic approach as described herein. FG-4592 treatment rewired energy metabolism, including an increase in the glycolytic capacity of cells, as well as a suppression of basal respiration. FG-4592 treatment in vivo alleviated the sensitivity of zebrafish embryos to mitochondrial dysfunction. These findings demonstrated that bypassing cellular oxygen sensing to trigger the HIF response was protective during states of respiratory chain inhibition. In an in vivo mouse model of mitochondrial disease, hypoxic breathing (11% $O_2$) was surprisingly found to be protective in diseased animals whereas mild hyperoxia (55% $O_2$ breathing) was toxic. The mouse model of mitochondrial disease evaluated herein is characterized by excess oxidative stress, indicating that reducing oxygen availability (and thus the availability of oxygen needed to produce reactive oxygen species) is an effective means to treat disorders characterized by excess oxidative stress. These findings indicate that promoting hypoxia or the hypoxia response can be used to treat or prevent mitochondrial dysfunction and oxidative stress disorders. In addition, hypoxia was found to protect against inflammation-induced death in the mouse model of mitochondrial disease, indicating that promoting hypoxia or the hypoxia response can be used to treat or prevent inflammatory disorders.

In one aspect, the disclosure provides a method of treating or preventing mitochondrial dysfunction, an oxidative stress disorder, or an inflammatory disorder in a subject in need thereof comprising increasing the activity of a hypoxia response in the subject. Increasing the activity of a hypoxia response can be achieved by, for example, exposing the subject to hypoxia. In some embodiments, the hypoxia response may include, but is not limited to, one or more of the following: a physiological response or a trigger of a hypoxia response.

In another aspect, the disclosure provides a method of treating or preventing mitochondrial dysfunction, an oxidative stress disorder, or an inflammatory disorder in a subject in need thereof, the method comprising administering to the subject by inhalation a therapeutically effective amount of a therapeutic gas at normobaria comprising between 5 to 20% $O_2$. In some embodiments, the therapeutic gas comprises between 10 to 15% $O_2$, between 10 to 12% $O_2$, or about 11% $O_2$.

In another aspect, the disclosure provides a method of treating or preventing mitochondrial dysfunction, an oxidative stress disorder, or an inflammatory disorder in a subject in need thereof, the method comprising causing the subject to breathe a therapeutically effective amount of air in a hypobaric chamber. In some embodiments, the hypobaric chamber has an atmospheric pressure equal to the atmospheric pressure at an elevation between 1,500 to 10,000 meters above sea level (e.g., an atmospheric pressure equal to the atmospheric pressure at an elevation between 1,500 to 8,000 meters or between 2,000 to 4,500 meters above sea level).

In another aspect, the disclosure provides a method of increasing the activity of a hypoxia response in a subject in need thereof comprising increasing the stability or the activation of HIF proteins in the subject.

In another aspect, the disclosure provides a treating or preventing mitochondrial dysfunction, an oxidative stress disorder, or an inflammatory disorder in a subject in need thereof comprising increasing cellular glycolysis in the subject.

In another aspect, the disclosure provides a method of treating or preventing mitochondrial dysfunction, an oxidative stress disorder, or an inflammatory disorder in a subject in need thereof comprising suppressing cellular basal respiration in the subject.

In some embodiments, nitric oxide is administered in combination with a method described herein. In some embodiments, the therapeutic gas comprises nitric oxide (e.g., wherein the concentration of nitric oxide in the therapeutic gas is at least 5 ppm, at least 10 ppm, at least 20 ppm, or is in the range of 0.5 ppm to 80 ppm).

In some embodiments, xenon is administered in combination with a method described herein. In some embodiments, the therapeutic gas comprises xenon (e.g., wherein the therapeutic gas comprises between 20-70% xenon).

In some embodiments, an agent that reduces pulmonary hypertension or raises the cGMP level in other cells (e.g., a phosphodiesterase inhibitor or a soluble guanylate cyclase sensitizer) is administered either systemically or by inhalation to the lung in combination with a method described herein.

Examples of phosphodiesterase inhibitors include: Zaprinast® (M&B 22948; 2-o-propoxyphenyl-8-azapurine-6-one; Rhone-Poulenc Rorer, Dagenham Essex, UK); WIN 58237 (1-cyclopentyl-3-methyl-6-(4-pyridyl)pyrazolo[3,4-d]pyrimidin-4-(5H)-one; Silver et al. (1994) J. Pharmacol. Exp. Ther. 271:1143); SCH 48936 ((+)-6a,7,8,9,9a,10,11,11a-octahydro-2,5-dimethyl-3H-pentalen(6a,1,4,5)imidazo[2,1-b]purin-4(5H)-one; Chatterjee et al. (1994) Circulation 90:1627, abstract no. 3375); KT2-734 (2-phenyl-8-ethoxy-cycloheptimidazole; Satake et al. (1994) Eur. J. Pharmacol. 251:1); E4021 (sodium 1-[6-chloro-4-(3,4-methylenedioxy-benzyl)-aminoquinazolin-2-y]piperidine-4-carboxylate sesquihydrate; Saeki et al. (1995) J. Pharmacol. Exp. Ther. 272:825); sildenafil (Viagra®); tadalafil (Cialis®); and vardenafil (Levitra®).

Examples of compounds that sensitize soluble guanylate cyclase include: 3-(5'-hydroxymethyl-2'-furyl)-1-benzylindazole ("YC-1"; Russwurm (2002) J. Biol. Chem. 277: 24883; Schmidt et al. (2001) Mol. Pharmacol. 59:220; and Friebe et al. (1998) Mol. Pharmacol. 54:962); compounds loosely based on YC-1 such as the pyrazolopyridine BAY 41-2272 (Stasch et al. (2001) Nature 410:212), the BAY 41-2272 derivatives ortho-(BAY 50-6038), meta-(BAY 51-9491) and para-PAL-(BAY 50-8364) (Becker et al. (2001) BMC Pharmacol. 1:13), and BAY 41-8543 (Stasch et al. (2002) Brit. J. Pharmacol. 135:333); 2-[1-(2-fluorobenzyl)-1H-pyrazolo[3,4-b]pyridin-3-yl]-5-(4-morpholinyl)-4,6-pyrimidine-diamine; 2-[1-(2-fluorobenzyl)-1H-pyrazolo[3,4-b]pyridin-3-yl]-5-(4-pyridinyl)-4-pyrimidmamine; methyl-4,6-diamino-2-[1-(2-fluorobenzyl)-1H-pyrazolo[3,4-b]pyridin-3-yl]-5-pyrimidinyl-(methyl)carbamate; methyl-4,6-diamino-2-[1-(2-fluorobenzyl)-1H-pyrazolo[3,4-b]pyridin-3-yl]-5-pyrimidinyl-carbamate; and 4-[((4-carboxybutyl)-{2-[(4-phenethylbenzyl)oxy]phenethyl}amino)methyl]benzoic acid.

In some embodiments, the therapeutic gas is administered to the subject continuously (e.g., for at least three minutes, at least 15 minutes, at least one hour, at least eight hours, or at least 24 hours). In some embodiments, the therapeutic gas is administered to the subject intermittently.

In some embodiments, the therapeutic gas is humidified and administered to the subject by nasal prongs, a face mask, an enclosed tent or chamber, an intra-tracheal catheter, an endotracheal tube, or a tracheostomy tube. For example, the therapeutic gas can be administered to the subject by a tent that is positioned over a bed or a crib on which the subject is placed.

In some embodiments, arterial oxygen saturation ($SpO_2$) is measured in the subject one or more times after administration of the therapeutic gas to the subject (e.g., continuously during administration of the therapeutic gas to the subject); and/or arterial partial oxygen pressure ($PaO_2$) is measured in the subject one or more times after administration of the therapeutic gas to the subject (e.g., continuously during administration of the therapeutic gas to the subject). In some embodiments, the measured $SpO_2$ value is used to feedback and automatically determine the concentration of inspired oxygen so as to maintain $SpO_2$ in the subject in the range of 50-90%; and/or the measured $PaO_2$ value is used to feedback and automatically determine the concentration of inspired oxygen so as to maintain $PaO_2$ in the subject in the range of 25 mm Hg to 70 mm Hg.

In any of the methods described herein, the subject optionally has a mitochondrial disorder. The mitochondrial disorder is in some examples a monogenic mitochondrial disorder.

In some examples, the mitochondrial disorder is characterized by a mutation in a gene selected from the group consisting of AARS2, AASS, ABAT, ABCB6, ABCB7, ABCD1, ACACA, ACAD8, ACAD9, ACADM, ACADS, ACADSB, ACADVL, ACAT1, ACO2, ACSF3, ACSL4, ADCK3, ADCK4, AFG3L2, AGK, AGXT, AIFM1, AK2, ALAS2, ALDH18A1, ALDH2, ALDH3A2, ALDH4A1, ALDH5A1, ALDH6A1, ALDH7A1, AMACR, AMT, APOPT1, ATIC, ATP5A1, ATP5E, ATP6, ATP8, ATPAF2, ATXN2, AUH, BAX, BCKDHA, BCKDHB, BCKDK, BCS1L, BOLA3, C10orf2, C12orf65, CA5A, CARS2, CASP8, CAT, CEP89, CHCHD10, CISD2, CLPB, CLPP, COA5, COA6, COASY, COQ2, COQ4, COQ6, COQ9, COX1, COX10, COX14, COX15, COX2, COX20, COX3, COX4I2, COX6A1, COX6B1, COX7B, CPDX, CPS1, CPT1A, CPT2, CYB5A, CYB5R3, CYC1, CYCS, CYP11A1, CYP11B2, CYP24A1, CYP27A1, CYP27B1, CYTB, D2HGDH, DARS2, DBT, DGUOK, DHCR24, DHODH, DHTKD1, DIABLO, DLAT, DLD, DMGDH, DMPK, DNA2, DNAJC19, DNM1L, EARS2, ECHS1, ELAC2, ETFA, ETFB, ETFDH, ETHE1, FARS2, FASTKD2, FBXL4, FECH, FH, FKBP10, FOXRED1, FXN, GARS, GATM, GCDH, GCSH, GDAP1, GFER, GFM1, GK, GLDC, GLRX5, GLUD1, GLYCTK, GPI, GPX1, GRHPR, GTPBP3, HADH, HADHA, HADHB, HARS2, HCCS, HIBCH, HK1, HMBS, HMGCL, HMGCS2, HOGA1, HSD17B10, HSD17B4, HSPD1, HTRA2, IDH2, IDH3B, ISCA2, ISCU, IVD, KARS, KIF1B, KRT5, L2HGDH, LARS2, LIAS, LONP1, LRP-PRC, LYRM4, LYRM7, MAOA, MARS2, MCCC1, MCCC2, MCEE, MFN2, MGME1, MICU1, MLH1, MLYCD, MMAB, MMACHC, MMADHC, MOCS1, MPC1, MPV17, MRPL12, MRPL3, MRPL44, MRPS16, MRPS22, mt-12S rRNA, mt-tRNATyr, mt-tRNATrp, mt-tRNAVal, mt-tRNAThr, mt-tRNASer1, mt-tRNASer2, mt-tRNAArg, mt-tRNAGln, mt-tRNAPro, mt-tRNAAsn, mt-tRNAMet, mt-tRNALeu1, mt-tRNALeu2, mt-tRNALys, mt-tRNAIle, mt-tRNAHis, mt-tRNAGly, mt-tRNAPhe, mt-tRNAGlu, mt-tRNAAsp, mt-tRNACys, mt-tRNAAla, MTFMT, MTO1, MTPAP, MUT, MUTYH, NAGS, NARS2, NCOA4, ND1, ND2, ND3, ND4, ND4L, ND5, ND6, NDUFA1, NDUFA10, NDUFA11, NDUFA12, NDUFA2, NDUFA4, NDUFA9, NDUFAF1, NDUFAF2, NDUFAF3, NDUFAF4, NDUFAF5, NDUFAF6, NDUFB11, NDUFB3, NDUFB9, NDUFS1, NDUFS2, NDUFS3, NDUFS4, NDUFS6, NDUFS7, NDUFS8, NDUFV1, NDUFV2, NFU1, NNT, NUBPL, OAT, OGDH, OGG1, OPA1, OPA3, OTC, OXCT1, PAM16, PANK2, PARK7, PARS2, PC, PCCA, PCCB, PCK2, PDHA1, PDHB, PDHX, PDP1, PDSS1, PDSS2, PET100, PEX11B, PEX6, PHYH, PINK1, PNPO, PNPT1, POLG, POLG2, PPM1K, PPOX, PRODH, PTRH2, PTS, PUS1, PYCR1, QDPR, RARS, RARS2, RMND1, RPL35A, RPS14, RRM2B, SARS2, SCO1, SCO2, SCP2, SDHA, SDHAF1, SDHAF2, SDHB, SDHC, SDHD, SECISBP2, SERAC1, SFXN4, SLC16A1, SLC19A3, SLC25A1, SLC25A12, SLC25A13, SLC25A15, SLC25A19, SLC25A20, SLC25A22, SLC25A3, SLC25A38, SLC25A4, SNAP29, SOD1, SPG7, SPR, SPTLC2, STAR, SUCLA2, SUCLG1, SUOX, SURF1, TACO1, TARS2, TAZ, TCIRG1, TIMM8A, TK2, TMEM126A, TMEM70, TMLHE, TPI1, TRIT1, TRMU, TRNT1, TSFM, TTC19, TUBB3, TUFM, TYMP, UNG, UQCR10, UQCRB, UQCRC2, UQCRQ, VARS2, WDR81, WFS1, XPNPEP3, and YARS2.

In some examples, the mitochondrial disorder is characterized by a point mutation in the mitochondrial DNA (mtDNA), deletion within the mtDNA, duplication within the mtDNA, or depletion of the mtDNA.

In some examples, the mitochondrial disorder is characterized by a biochemical deficiency of respiratory chain Complex I, II, III, IV, V, or a combination thereof.

In some examples, the mitochondrial disorder is Kearns-Sayre syndrome (KSS), Leber's hereditary optic neuropathy (LHON), myoclonic epilepsy ragged red fiber syndrome (MERRF), mitochondrial encephalopathy, lactic acidosis, and stroke (MELAS) syndrome, sensory ataxic neuropathy, dysarthria, and ophthalmoparesis (SANDO) syndrome, maternally inherited Leigh syndrome (MILS), myopathy and external ophthalmoplegia, neuropathy, gastrointestinal encephalopathy (MNGIE) syndrome, Leigh syndrome, maternally inherited diabetes and deafness (MIDD) syndrome, Alpers-Huttenlocher syndrome, Sengers syndrome, mitochondrial myopathy, lactic acidosis and sideroblastic anemia (MLASA), chronic progressive external ophthalmoplegia (CPEO), autosomal dominant progressive external ophthalmoplegia (AdPEO), neuropathy, ataxia, retinitis pigmentosa (NARP) syndrome, GRACILE syndrome, diabetes insipidus, diabetes mellitus, optic atrophy, and deafness (DIDMOAD) syndrome, or Pearson's syndrome.

In some examples, the mitochondrial disorder presents with one or more of gray matter disease, white matter disease, seizures, migraines, ataxia, stroke, stroke-like episodes, deafness, optic neuropathy, peripheral neuropathy, retinopathy, external opthalmoplegia, liver failure, kidney failure, pancreatic exocrine dysfunction, intestinal pseudoobstruction, anemia, skeletal muscle myopathy, cardiomyopathy, cardiac conduction defects, short stature, hypogonadism, immune dysfunction, or metabolic acidosis.

In some examples, the mitochondrial disorder is diagnosed by an algorithm selected from the group consisting of the Bernier criteria (Bernier et al., "Diagnostic criteria for respiratory chain disorders in adults and children," Neurology, 59(9):1406-11, 2002), the Morava criteria (Morava et al., "Mitochondrial disease criteria: diagnostic applications in children," Neurology, 67(10):1823-6, 2006), and Consensus from the Mitochondrial Medicine Society (Parikh et al., "Diagnosis and management of mitochondrial disease: a consensus statement from the Mitochondrial Medicine Society," Genetics in Medicine, 17(9):689-701, 2015).

In some examples, the mitochondrial disorder is a mitochondrial respiratory chain disorder.

In some embodiments, the subject is less than five years of age (e.g., less than one year of age).

In any of the methods described herein, the subject optionally has an age-associated disorder (e.g., type 2 diabetes, insulin resistance, neurodegeneration, peripheral neuropathy, sarcopenia, muscle atrophy, deafness, atherosclerosis, cardiovascular disease, heart failure, chronic kidney disease, cancer, arthritis, cataracts, or osteoporosis).

In any of the methods described herein, including but not limited to a combination treatment with nitric oxide, xenon, or an agent that reduces pulmonary hypertension, the subject can be treated to prevent (completely or partially) the occurrence of mitochondrial dysfunction associated with aging. In these embodiments, the subject can be, for example, at least 20 years of age, at least 30 years of age, at least 40 years of age, or older. In these preventative methods, the subject can benefit from treatment even without having any evident disease. For example, a subject can be administered by inhalation a therapeutically effective amount of a therapeutic gas comprising (i) between 5 to 20% $O_2$, and (ii) nitric oxide (e.g., an amount of nitric oxide disclosed herein). In another example, a subject can breathe a therapeutically effective amount of air in a hypobaric chamber in combination with inhalation of nitric oxide (e.g., an amount of nitric oxide disclosed herein).

In any of the methods described herein, the subject optionally exhibits mitochondrial dysfunction associated with aging (e.g., the subject is at least 65 years of age or is at least 75 years of age).

In any of the methods described herein, the mitochondrial dysfunction occurs in response to an environmental insult (e.g., a drug, an antibiotic, an antiviral drug, or a pesticide that is toxic to mitochondria.

In any of the methods described herein, the subject can be been identified as having a genetic mutation associated with onset of a mitochondrial disorder and treatment is initiated before the onset of symptoms of the disorder. For example, the subject can be identified as having a mutation in a gene selected from the group consisting of AARS2, AASS, ABAT, ABCB6, ABCB7, ABCD1, ACACA, ACAD8, ACAD9, ACADM, ACADS, ACADSB, ACADVL, ACAT1, ACO2, ACSF3, ACSL4, ADCK3, ADCK4, AFG3L2, AGK, AGXT, AIFM1, AK2, ALAS2, ALDH18A1, ALDH2, ALDH3A2, ALDH4A1, ALDH5A1, ALDH6A1, ALDH7A1, AMACR, AMT, APOPT1, ATIC, ATP5A1, ATP5E, ATP6, ATP8, ATPAF2, ATXN2, AUH, BAX, BCK-DHA, BCKDHB, BCKDK, BCS1L, BOLA3, C10orf2, C12orf65, CA5A, CARS2, CASP8, CAT, CEP89, CHCHD10, CISD2, CLPB, CLPP, COA5, COA6, COASY, COQ2, COQ4, COQ6, COQ9, COX1, COX10, COX14, COX15, COX2, COX20, COX3, COX4I2, COX6A1, COX6B1, COX7B, CPDX, CPS1, CPT1A, CPT2, CYB5A, CYB5R3, CYC1, CYCS, CYP11A1, CYP11B2, CYP24A1, CYP27A1, CYP27B1, CYTB, D2HGDH, DARS2, DBT, DGUOK, DHCR24, DHODH, DHTKD1, DIABLO, DLAT, DLD, DMGDH, DMPK, DNA2, DNAJC19, DNM1L, EARS2, ECHS1, ELAC2, ETFA, ETFB, ETFDH, ETHE1, FARS2, FASTKD2, FBXL4, FECH, FH, FKBP10, FOXRED1, FXN, GARS, GATM, GCDH, GCSH, GDAP1, GFER, GFM1, GK, GLDC, GLRX5, GLUD1, GLYCTK, GPI, GPX1, GRHPR, GTPBP3, HADH, HADHA, HADHB, HARS2, HCCS, HIBCH, HK1, HMBS, HMGCL, HMGCS2, HOGA1, HSD17B10, HSD17B4, HSPD1, HTRA2, IDH2, IDH3B, ISCA2, ISCU, IVD, KARS, KIF1B, KRT5, L2HGDH, LARS2, LIAS, LONP1, LRPPRC, LYRM4, LYRM7, MAOA, MARS2, MCCC1, MCCC2, MCEE, MFN2, MGME1, MICU1, MLH1, MLYCD, MMAB, MMACHC, MMADHC, MOCS1, MPC1, MPV17, MRPL12, MRPL3, MRPL44, MRPS16, MRPS22, mt-12S rRNA, mt-tRNATyr, mt-tRNATrp, mt-tRNAVal, mt-tRNAThr, mt-tRNASer1, mt-tRNASer2, mt-tRNAArg, mt-tRNAGln, mt-tRNAPro, mt-tRNAAsn, mt-tRNAMet, mt-tRNALeu1, mt-tRNALeu2, mt-tRNALys, mt-tRNAIle, mt-tRNAHis, mt-tRNAGly, mt-tRNAPhe, mt-tRNAGlu, mt-tRNAAsp, mt-tRNACys, mt-tRNAAla, MTFMT, MTO1, MTPAP, MUT, MUTYH, NAGS, NARS2, NCOA4, ND1, ND2, ND3, ND4, ND4L, ND5, ND6, NDUFA1, NDUFA10, NDUFA11, NDUFA12, NDUFA2, NDUFA4, NDUFA9, NDUFAF1, NDUFAF2, NDUFAF3, NDUFAF4, NDUFAF5, NDUFAF6, NDUFB11, NDUFB3, NDUFB9, NDUFS1, NDUFS2, NDUFS3, NDUFS4, NDUFS6, NDUFS7, NDUFS8, NDUFV1, NDUFV2, NFU1, NNT, NUBPL, OAT, OGDH, OGG1, OPA1, OPA3, OTC, OXCT1, PAM16, PANK2, PARK7, PARS2, PC, PCCA, PCCB, PCK2, PDHA1, PDHB, PDHX, PDP1, PDSS1, PDSS2, PET100, PEX11B, PEX6, PHYH, PINK1, PNPO, PNPT1, POLG, POLG2, PPM1K, PPOX, PRODH, PTRH2, PTS, PUS1, PYCR1, QDPR, RARS, RARS2, RMND1, RPL35A, RPS14, RRM2B, SARS2, SCO1, SCO2, SCP2, SDHA, SDHAF1, SDHAF2, SDHB, SDHC, SDHD, SECISBP2, SERAC1, SFXN4, SLC16A1, SLC19A3, SLC25A1, SLC25A12, SLC25A13, SLC25A15, SLC25A19, SLC25A20, SLC25A22, SLC25A3, SLC25A38, SLC25A4, SNAP29, SOD1, SPG7, SPR, SPTLC2, STAR, SUCLA2, SUCLG1, SUOX, SURF1, TACO1, TARS2, TAZ, TCIRG1, TIMM8A, TK2, TMEM126A, TMEM70, TMLHE, TPI1, TRIT1, TRMU, TRNT1, TSFM, TTC19, TUBB3, TUFM, TYMP, UNG, UQCR10, UQCRB, UQCRC2, UQCRQ, VARS2, WDR81, WFS1, XPNPEP3, and VARS2.

Examples of oxidative stress disorders that can be treated according to the methods described herein include Parkinson's disease, Alzheimer's disease, amyotrophic lateral sclerosis, Huntington's disease, multiple sclerosis, Asperger syndrome, attention deficit hyperactivity disorder, diabetes, cardiovascular disease, cancer, Lafora disease, atherosclerosis, heart failure, myocardial infarction, fragile X syndrome, sickle cell disease, lichen planus, vitiligo, and autism.

Examples of inflammatory disorders that can be treated according to the methods described herein include rheumatoid arthritis, psoriatic arthritis, ankylosing spondylitis, inflammatory bowel disease (e.g., ulcerative colitis and Crohn's disease), psoriasis, inflammatory myositis, Langerhans-cell histiocytosis, adult respiratory distress syndrome, Wegener's granulomatosis, vasculitis, cachexia, stomatitis, idiopathic pulmonary fibrosis, dermatomyositis, polymyositis, non-infectious scleritis, chronic sarcoidosis with pulmonary involvement, myelodysplastic syndrome, moderate to severe chronic obstructive pulmonary disease without significant right to left shunting of blood, and giant cell arteritis.

In another aspect, the disclosure provides a system comprising (i) an enclosed tent or chamber or a breathing apparatus, (ii) a hypoxia induction system that delivers oxygen-depleted air to the enclosed tent or chamber or the breathing apparatus, wherein the oxygen-depleted air comprises between 5 to 20% $O_2$, and (iii) a device (e.g., pulse oximeter) that measures arterial oxygen saturation in a subject breathing air within the enclosed tent or chamber or from the breathing apparatus, wherein the system adjusts the oxygen content of the oxygen-depleted air delivered to the enclosed tent or chamber or the breathing apparatus based upon the oxygen saturation measured by the device such that oxygen saturation in the subject is maintained within the range of 50% to 90% (e.g., within the range of 80% to 90% or at about 85%, or within the range of 55% to 65% or at about 80%). In some embodiments, the hypoxia induction system comprises a first container comprising a first gas comprising nitrogen and a second container comprising a second gas comprising oxygen, and wherein the oxygen-depleted air delivered to the enclosed tent or chamber or the breathing apparatus is prepared by mixing the first gas and the second gas. In some embodiments, the hypoxia induction system intakes ambient air, reduces the oxygen content of the intake air, to produce the oxygen-depleted air that is delivered to the enclosed tent or chamber or the breathing apparatus. In some embodiments, the hypoxia induction system intakes ambient air, adds nitrogen to the intake air, to produce the oxygen-depleted air that is delivered to the enclosed tent or chamber or the breathing apparatus.

In any of the embodiments described herein, the subject can be a human subject.

In a further aspect, the disclosure provides a method of screening for a compound that increases the activity of a hypoxia response comprising
  a) administering a candidate compound to a first set of one or more cells with a compromised function of the mitochondrial respiratory chain;
  b) measuring the growth of the first set of one or more cells; and
  c) comparing the growth of the first set of one or more cells to the growth of a second set of one or more cells, wherein the second set of one or more cells also have compromised function of the mitochondrial respiratory chain, but have not been administered the candidate compound,
  wherein if the growth of the first set of cells is greater than the growth of the second set of cells then the candidate compound increases the activity of a hypoxia response.

In another aspect, the disclosure provides a method of screening for targets for the modulation of mitochondrial respiratory chain function comprising
  a) administering to a first set of one or more cells one or more sgRNAs targeting at least one gene in the human genome;
  b) compromising the function of the mitochondrial respiratory chain in the first set of one or more cells;
  c) measuring the growth of the first set of one or more cells; and
  d) comparing the growth of the first set of one or more cells to the growth of a second set of one or more cells, wherein the second set of one or more cells have been administered the same one or more sgRNAs, but have less compromised function of the mitochondrial respiratory chain,
  wherein if the relative enrichment of a sgRNA in the first set of cells is greater than the corresponding enrichment in the second set of cells then the gene is a target for the modulation of cellular or whole body response to mitochondrial respiratory chain (dys)function.

BRIEF DESCRIPTION OF THE DRAWINGS

FIG. 1 shows a schematic representation of hypoxia.

FIG. 2 shows a schematic representation of normoxia.

FIGS. 18-1A-18-3F show that chronic hypoxic breathing (11% $O_2$) prevents neurological disease symptoms and pathology in a mouse model of Leigh syndrome, whereas a few days of breathing mild hyperoxia (55% $O_2$) is lethal and produces fatal pulmonary edema. (18-1A) Ndufs4 KO mice of both genders were chronically exposed to hypoxic breathing at normobaria (11% $O_2$; top line), normoxia (21% $O_2$; middle line), or hyperoxia (55% $O_2$; bottom line) at 30 days of age and survival was recorded (n=12, n=12, n=9 mice, respectively). (18-1B) Body weights were measured in WT and KO mice exposed to normoxia or hypoxia, three times a week upon enrollment in the study. Weights are shown as mean±S.E. (18-1C) Representative images of 50 day-old KO mice exposed to normoxia or hypoxia. (18-2D) Body temperature was measured in KO mice exposed to normoxia or hypoxia at approximately age 30 days, 40 days, and 50 days. Temperatures are shown as mean±S.E. (18-2E) Latency to fall on an accelerating rod was measured as median values of triplicate trials per mouse for WT and KO mice, exposed to normoxia or hypoxia at different ages. (18-3F) Representative 1 hour locomotor activity traces of sick, normoxia-treated KO mice, and age-matched hypoxia-treated KO mice, as well as controls. *denotes t-test p-value <0.05.

FIGS. 19-1A-19-2E show that therapeutic hypoxic breathing (11% $O_2$) by Ndufs4 KO mice prevents the appearance of metabolic disease markers, as well as neuropathology, without rescuing Complex I activity. (19-1A) Hematocrit values for WT and KO mice treated with normoxia or hypoxia at normobaria for approximately 3 weeks (n=3-4 per group). (19-1B) Complex I activity in KO mice relative to WT mice, in both normoxic and hypoxic conditions (n=3-4 per group). (19-1C) Representative images for immunostaining against the inflammatory marker, Iba-1, in the olfactory bulb and cerebellum of Ndufs4 KO mice treated with hypoxia or normoxia and WT mice exposed to normoxic breathing. (19-2D) Plasma α-hydroxybutyrate levels in WT and KO mice, exposed to hypoxia or normoxia (n=4-8 per group). Median shown as horizontal bar. (19-2E) Plasma lactate in WT and KO mice, exposed to hypoxia or normoxia (n=4-8 per group). Median shown as horizontal bar.

FIG. 20 shows spontaneous activity measured in WT and Ndufs4 KO mice exposed to normoxia or hypoxia. Distance traveled and jump counts within 1 hour are shown (Mean±S.E.). n=7, 5, 9, 9 for WT (21% $O_2$), WT (11% $O_2$), KO (21% $O_2$), KO (11% $O_2$) respectively.

FIGS. 25-1A-25-2F show that intermittent hypoxic (11%) breathing (10 h/day) did not alleviate mitochondrial disease. (25-1A) Survival rates for Ndufs4 KO mice breathing different oxygen levels and intermittent hypoxic breathing for 10 h/day (IH). IH versus normoxia, log rank p=0.77, HR 1.13 (0.48-2.79). (25-1B) Body weights after breathing different oxygen levels and during intermittent hypoxic breathing starting at 30 d of age. (25-2C) Body temperature and (25-2D) latency to fall from an accelerating, rotating rod for Ndufs4 KO mice breathing various oxygen levels or receiving intermittent hypoxia starting at 30 days of age. (25-2E) Hematocrit levels for WT and Ndufs4 KO mice following three weeks of exposure to normoxia, hypoxia or intermittent hypoxic breathing. (25-2F) Representative MRI of a 65d Ndufs4 KO mouse exposed to intermittent hypoxic breathing. Arrows denote lesions in vestibular nuclei. Data mean±SE; *p<0.05 vs KO 11% $O_2$; # p<0.05 vs KO 21% $O_2$.

FIGS. 26-1A-26-2D shows that breathing moderate hypoxia (17% $O_2$) does not alleviate murine mitochondrial disease. (26-1A) Survival rates for Ndufs4 KO mice breathing at different oxygen levels starting at 30 days of age. (26-1B) Time course of body weight (n=6, each group) and (26-2C) body temperature for 17% oxygen exposure, compared to 21% or 11% oxygen exposure for 30, 40 and 50 days. (26-2D) Venous hematocrit after three weeks of exposure to different oxygen levels. Data mean±SE; *p<0.05 differs vs 11% oxygen, # p<0.05 differs vs 17% oxygen.

DETAILED DESCRIPTION

The disclosure provides a method of treating or preventing mitochondrial dysfunction, an oxidative stress disorder, or an inflammatory disorder in a subject in need thereof comprising increasing the activity of the hypoxia response pathway in the subject. In some embodiments, the method comprises suppression of mitochondrial disease. In certain embodiments, the suppression of mitochondrial disease occurs via mediation of the hypoxia response.

The disclosure also provides methods of screening for compounds that treat or prevent mitochondrial dysfunction, an oxidative stress disorder, or an inflammatory disorder. In some embodiments, methods of screening for a compound that increases the activity of a hypoxia response is provided. In other embodiments, methods of screening for targets for the modulation of response to mitochondrial respiratory chain dysfunction are provided.

A. Terms, Definitions and Abbreviations

Figures 1, 18:
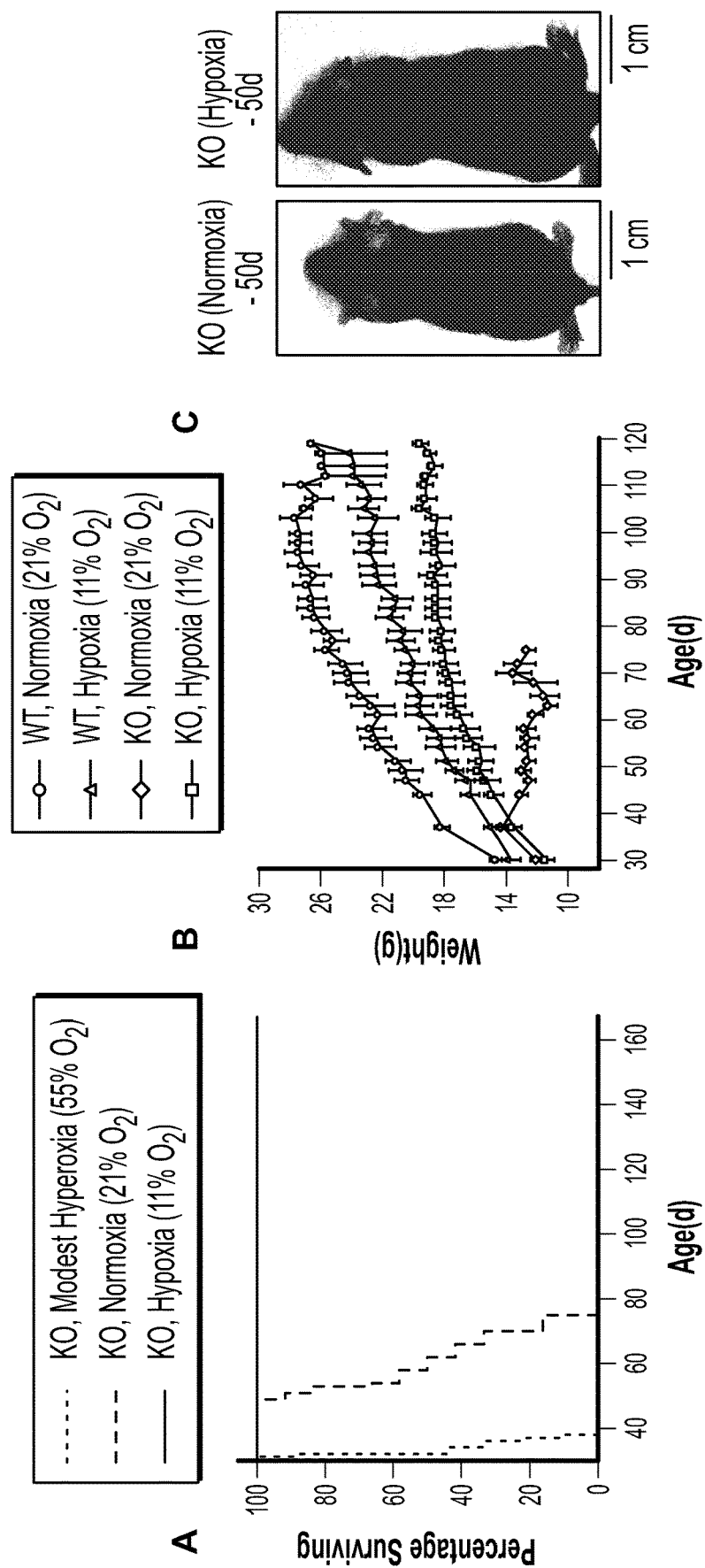

As used herein "hypoxia" refers to a deficiency of oxygen. A low oxygen condition is also referred to as a "hypoxic condition." See FIG. 1 for a schematic representation of hypoxia. HIF1α is stabilized during hypoxia.

As used herein a "hypoxia inducible transcription factor" (HIF) is an oxygen-sensitive transcription factor that responds to low oxygen. Non-limiting examples of hypoxia inducible transcription factors include alpha subunits of hypoxia inducible transcription factors (e.g., HIF1α, HIF2 α and HIF3α), and beta subunits (HIF1β, HIF2β, and HIF3β). HIFs are also referred to herein as HIF proteins. For example, in a transcriptional complex HIF is a heterodimer comprising an alpha and a beta subunit, which induces transcription of HIF-responsive genes during hypoxia or under hypoxic conditions.

HIF-responsive genes include but are not limited to genes involved in glucose metabolism, for example, transport (e.g., glucose transporter 1 (GLUT1) and glucose transporter 3 (GLUT3)), tricarboxylic acid (TCA) cycle (also known as the Krebs cycle or the citric acid cycle, e.g., PDK1), glycolysis (e.g., hexokinase 1 (HK1); hexokinase 2 (HK2); glyceraldehyde 3-phosphate dehydrogenase (GAPDH); 6-phosphofructo-2-kinase/fructose-2,6-bisphosphatase-3 (PFKBF3); 6-phosphofructo-2-kinase, liver type (PFKL); phosphoglycerate kinase 1 (PGK1); and pyruvate kinase, muscle (PKM)); redox modulation (e.g., lactate dehydrogenase A (LDHA) and monocarboxylate transporter 4 (MCT4)); feedback regulation (e.g., Egl-9 family hypoxia-inducible factor 1 (EGLN1) and Egl-9 family hypoxia-inducible factor 3 (EGLN3)); angiogenesis (e.g., vascular endothelial growth factor (VEGF); vascular endothelial growth factor receptor (VEGFR); endoglin (ENG); transforming growth factor, beta 3 (TGF-B3); adrenomedullin (ADM); nitric oxide synthase 2, inducible (NOS2); heme oxygenase 1 (HMOX1)); and promoting red blood cell maturation and oxygen transport, for example, erythropoiesis (e.g., erythropoietin (EPO)) and iron metabolism (e.g., transferrin (TF) and transferrin receptor (TFRC)). Other examples of HIF-responsive genes include the genes disclosed in *J. Med. Chem.* 56, 9369-9402 (2013), incorporated herein by reference in its entirety.

A "hypoxia response" is a response by a cell and/or an organism to hypoxia. Hypoxia is one non-limiting way to induce a hypoxia response. A hypoxia response includes, but is not limited to, a physiological response (e.g., a systemic or pulmonary hemodynamic response, a change in the regulation of cellular metabolism, and up-regulation of genes (e.g., HIF responsive genes)) and a pathological response (e.g., pulmonary hypertension, cerebral ischemia, myocardial ischemia, and tumor angiogenesis). Non-limiting examples of systemic responses include pulmonary vasoconstriction, systemic vasodilation, increased cytosolic calcium concentration, and neurotransmitter release, for example, catecholamines, acetylcholine, and serotonin. Non-limiting examples of a response affecting the regulation of cellular metabolism include uncontrolled cell swelling, cell necrosis, impaired mitochondrial respiratory chain function, increased cellular glycolysis, decreased cellular energy consumption, and decreased cellular oxygen consumption. Other examples of a hypoxia response include increased ventilation, increased cardiac output, a switch from aerobic to anaerobic metabolism, promotion of improved vascularization, an increase of erythropoietin with augmented erythropoiesis, enhancement of the oxygen carrying capacity of the blood, reduced oxygen toxicity, increased or reduced reactive oxygen species, and increased or reduced oxidative stress. A hypoxia response may involve oxygen-responsive pathways to sense and to respond to changes in oxygen availability. For example, HIFs may respond to a low oxygen environment and activate one or more HIF-responsive genes.

Figures 2, 18:
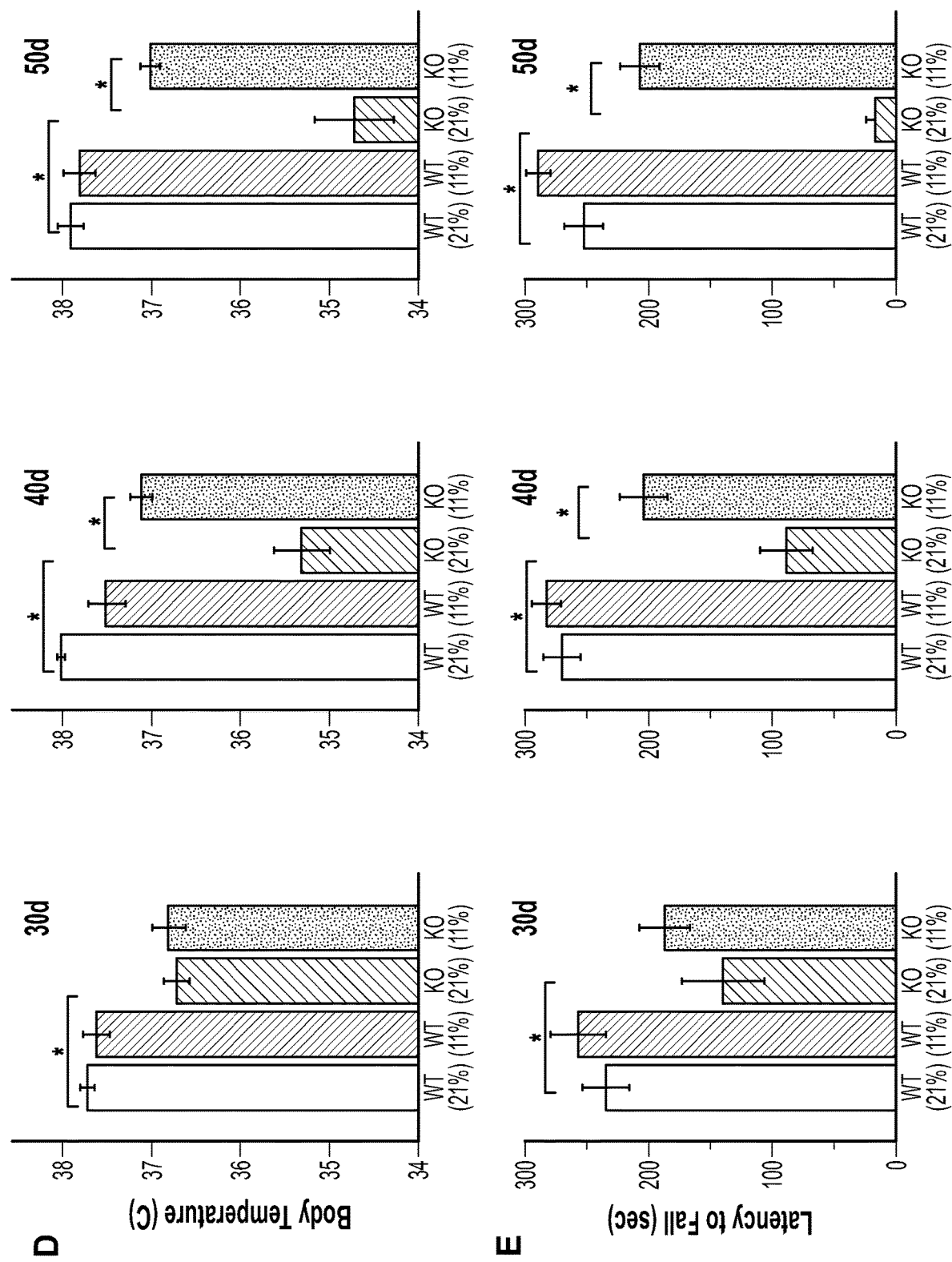
Figures 3, 18:
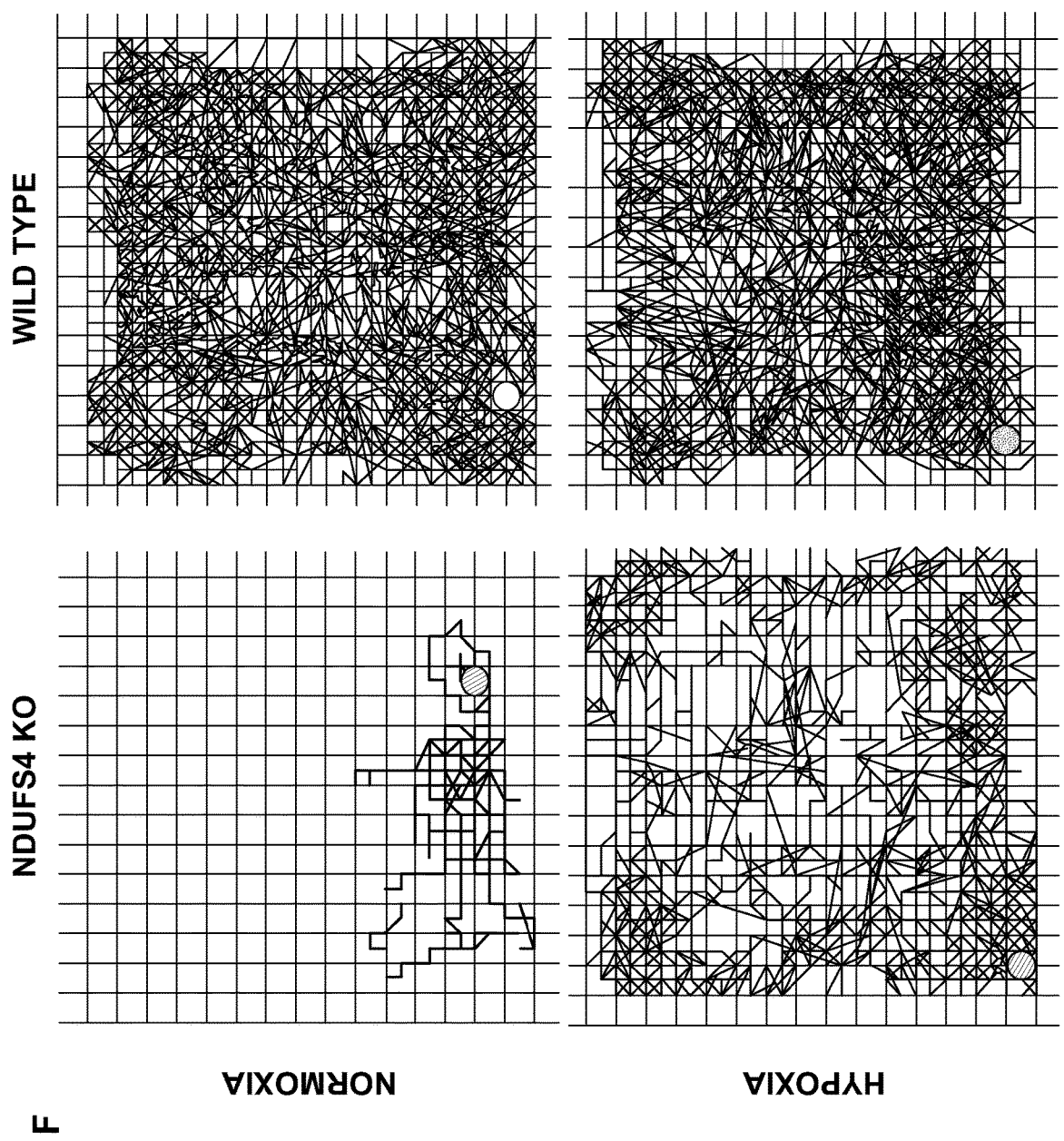

Normoxia or a "normoxic condition" refers to a normal level of oxygen condition. See FIG. 2 for a schematic representation of normoxia. HIF1α is degraded under normoxic conditions.

The "prolyl-hydroxylase" (PHD) enzymes hydroxylate alpha subunits of HIF at conserved proline residues. Hydroxylation and degradation occurs under normoxic conditions. PHD enzyme activity is inhibited under hypoxic conditions. Non-limiting examples of PHD inhibitors include 2-oxoglutarate analogs (also known as α-ketoglutarate, e.g., roxadustat, 2,4-diethylpyridine dicarboxylate, dimethyloxallyl glycine, IOX2, and N-oxalylglycine), β-oxocarboxylic acids (e.g., 1,4-dihydrophenonthrolin-4-one-3-carboxylic acid), and BAY-85-3934 (also known as 2-(6-morpholinopyrimidin-4-yl)-4-(1H-1,2,3-triazol-1-yl)-1,2-dihydro-3H-pyrazol-3-one). Roxadustat is also known as FG-4592 and N-[(4-hydroxy-1-methyl-7-phenoxy-3-isoquinolinyl)carbonyl]glycine. IOX2 is also known as (1-benzyl-4-hydroxy-2-oxo-1,2-dihydroquinoline-3-carbonyl)glycine. Additional examples of 2-oxoglutarate analogs as PHD inhibitors include 4-hydroxyisoquinoline-2-carbonylglycine derivatives, 4-hydroxy-2-quinoline, pyrrolopyridines, thiazolopyridines, isothiazolopyridines, 4-hydroxycoumarins, and 4-hydroxythiocoumarins (11). For example, FG-2216 ((1-chloro-4-hydroxyisoquinoline-3-carbonyl)glycine) and FG-4497 ((1-hydroxy-6-(phenylthio)isoquinoline-3-carbonyl)glycine). Any known prolyl-hydroxylase inhibitor may be used in methods of the invention. Some additional examples of PHD inhibitors are disclosed in M. Rabinowitz, Inhibition of hypoxia-inducible factor prolyl hydroxylase domain oxygen sensors: tricking the body into mounting orchestrated survival and repair responses. *J. Med. Chem.* 56, 9369-9402 (2013), incorporated herein by reference in its entirety.

The "Von Hippel Lindau" gene encodes the Von Hippel Lindau (VHL) tumor suppressor protein. The hydroxylated form of HIF is recognized by the ubiquitin ligase, VHL, and targeted for degradation by the proteasome under normoxic conditions.

As used herein, "endogenous cellular oxygen sensing" involves a mechanism or process used by the body or cells to determine or to measure the levels of oxygen available to the cells. For example, oxygen sensing may occur using a hypoxia response.

As used herein, a "mitochondrial respiratory chain disorder" is a heterogeneous group of genetic disorders that share involvement of the cellular bioenergetics machinery due to molecular defects affecting the mitochondrial oxidative phosphorylation system. Over 150 different genetic causes of mitochondrial respiratory chain disorder impact one or more of the five respiratory chain complexes. The respiratory chain complexes include Complex I (NADH-coenzyme Q reductase or NADH dehydrogenase), Complex II (succinate-coenzyme Q reductase or succinate dehydrogenase), Complex III (cytochrome bci complex or coenzyme Q-cytochrome C oxidoreductase), Complex IV (cytochrome C oxidase), and Complex V (ATP synthase, adenosine triphosphate synthase). A mitochondrial lesion is damage to a gene encoded by mitochondrial DNA or nuclear-encoded mitochondrial protein. The mitochondrial lesion may be introduced by oxidative stress. Mitochondrial diseases include a mitochondrial respiratory chain disorder.

A "Complex I inhibitor" inhibits the functioning of the NADH-coenzyme Q reductase in the mitochondrial electron transport chain and prevents electron transfer from NADH to coenzyme Q10. Non-limiting examples of a Complex I inhibitor include acetogenins (e.g., annonacin, bullatacin or rolliniastatin-2, and uvaricin), reduced nicotinamide adenine dinucleotide (NADH) analogs (e.g., adenosine diphosphate ribose), ubiquinone analogs (e.g., piericidin (also referred to as piericidin A) and rotenone), and metformin.

A "Complex III inhibitor" inhibits the functioning of the coenzyme Q-cytochrome C oxidoreductase in the mitochondrial electron transport chain and prevents the biochemical generation of ATP. Non-limiting examples of a Complex III inhibitor include $Q_i$ site inhibitors (e.g., antimycin) and $Q_o$ site inhibitors (quinone outside inhibitors, e.g., myxothiazol, stigmatellin, and strobilurin derivatives).

A "Complex V inhibitor" inhibits the functioning of ATP synthase in the mitochondrial electron transport chain and prevents the biochemical generation of ATP. Non-limiting examples of a Complex V inhibitor include α-helical basic peptide inhibitors (e.g., melittin), catechins (e.g., epicatechin, epicatechin gallate, and epigallocatechin gallate), catecholestrogens (e.g., 4-hydroxyestradiol and 2-hydroxyestradiol), flavones (e.g., quercetin, morin, kaempferol, and genistein), oligomycins (e.g., oligomycin A and oligomycin), polyketide inhibitors (e.g., peliomycin, venturicidin A, B, and X, and ossamycin), stilbenes (e.g., resveratrol, piceatannol, and diethylstilbestrol), tentoxin and derivatives (e.g., tentoxin), and nucleotide analogs (e.g., GTP, FTP, and TNP-ATP). A Complex V inhibitor is also referred to as an ATP synthase inhibitor.

A "compromised function of the mitochondrial respiratory chain" refers to one or more cells with abnormal functioning of the cellular bioenergetics machinery affecting the mitochondrial oxidative phosphorylation system. For example, this may be a result of genetic defects in one or more respiratory chain complexes, a mitochondrial lesion, an inhibitor of one or more respiratory chain complexes or any physiological situation which impairs mitochondrial respiratory chain function.

As used herein, "basal respiration" refers to routine respiration in an intact and healthy cell. The proton current generated by basal respiration supplies ATP synthesis and the proton leak.

As used herein, "cellular stress" may be caused by environmental stressors including temperature extremes, toxin exposure, mechanical damage, and hypoxic conditions. For example, viral prodromes, dehydration, and low oxygen cause cellular stress. When a cell is exposed to unfavorable environmental conditions of cellular stress, the cell can mount a response to protect the cell against the environmental stressors.

A "high energy demand" requires the cell to produce a large amount of energy to perform required functions. For example, mitochondria are organelles that carry out the process of aerobic respiration to breakdown molecules like glucose in the presence of oxygen. The cellular bioenergetics machinery uses respiratory chain complexes to produce energy for a cell. In certain embodiments, high energy demand occurs in cells when an organism comprising those cells exerts itself beyond a sedentary condition. In other embodiments, high energy demand occurs when an organism comprising the cells is injured in a location near the cells. In other embodiments, high energy demand occurs when an organism comprising the cells is suffering from an infectious disease that affects the cells.

An "age-associated disorder" is a disease or a disorder seen with increasing frequency as individuals age. These disorders are associated with gradual deterioration of function (e.g., quantitative decline in the activity of the mitochondrial respiratory chain). Non-limiting examples of an age-associated disorder include type 2 diabetes, neurodegeneration (e.g., Alzheimer's disease), sarcopenia (muscle loss), atherosclerosis, cardiovascular disease, cancer, arthritis, cataracts, and osteoporosis.

"CRISPR" is a clustered regularly interspaced short palindrome repeat guided by RNA to introduce a targeted loss-of function mutation at one or more specific sites in the genome. The system includes a sgRNA and an endonuclease such as the CRISPR associated protein 9 (Cas9) nuclease. Various compositions and methods of use related to the delivery, engineering, optimization and therapeutic applications of systems, methods, and compositions used for the control of gene expression involving sequence targeting, such as genome perturbation or gene-editing, may be utilized in the invention. In one aspect, the genome perturbation or gene-editing relates to Clustered Regularly Interspaced Short Palindromic Repeats (CRISPR) and components thereof. The CRISPR-Cas system does not require the generation of customized proteins to target specific sequences but rather a single Cas enzyme can be programmed by a short RNA molecule to recognize a specific DNA target. Examples of useful CRISPR-Cas systems and components include, but are not limited to, the components, or any corresponding orthologs thereof, and delivery of such components, including methods, materials, delivery vehicles, vectors, particles, AAV, and making and using thereof, as described in, e.g., US Pat. No. 8 U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and PCT Patent Publications WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, and applications related thereto.

As used herein, "RNAi Gene Enrichment Ranking" (RIGER) analysis uses an algorithm to rank screening hits by the consistent enrichment among multiple sgRNAs targeting the same gene. The highest ranking (e.g., lowest number, rank 1) gene represents a gene target. Additional details about the algorithm can be found in B. Luo et al., Highly parallel identification of essential genes in cancer cells. *Proc. Natl. Acad. Sci. U.S.A.* 105, 20380-20385 (2008), incorporated herein by reference in its entirety.

A "sgRNA" is an RNA that guides the insertion or deletion of nucleotides into target locations in concert with the Cas9 nuclease.

B. Embodiments

In one aspect, the current disclosure provides a method of treating or preventing mitochondrial dysfunction, an oxidative stress disorder, or an inflammatory disorder in a subject in need thereof comprising increasing the activity of a hypoxia response in the subject. Increasing the activity of a hypoxia response can be achieved by, for example, exposing the subject to hypoxia. In some embodiments, the hypoxia response may include, but is not limited to, one or more of the following: a physiological response (e.g., a systemic response, a change in the regulation of cellular metabolism, and up-regulation of genes (e.g., HIF responsive genes)) or a trigger of a hypoxia response (e.g., cerebral ischemia, myocardial ischemia, and tumor angiogenesis). In another embodiment, the hypoxia response is a systemic or pulmonary response selected from the group consisting of pulmonary vasoconstriction, systemic vasodilation, increased cytosolic calcium concentration, neurotransmitter release. In still another embodiment, the hypoxia response is a response affecting the regulation of cellular metabolism selected from the group consisting of uncontrolled cell swelling, cell necrosis, impaired mitochondrial respiratory chain function, increased cellular glycolysis, and decreased cellular energy consumption. In yet another embodiment, a hypoxia response is selected from the group consisting of increased ventilation, increased cardiac output, a switch from aerobic to anaerobic metabolism, promotion of improved vascularization, and augmented erythropoietin levels with enhancement of erythropoiesis, enhancement of the oxygen carrying capacity of the blood, reduced oxygen toxicity, increased or reduced reactive oxygen species, and increased or reduced oxidative stress.

In some embodiments, increasing the activity of a hypoxia response includes increasing the activation of a hypoxia inducible transcription factor (HIF). In other embodiments, the HIF is selected from the group consisting of alpha or beta subunits of hypoxia inducible transcription factors. In certain embodiments, the HIF is selected from the group consisting of HIF1α, HIF3α, HIF1β, HIF2β, HIF3β, and HIF2α.

In another embodiment, increasing the activity of a hypoxia response includes inducing transcription of HIF-responsive genes. In other embodiments, the transcribed gene is involved in one of the following glucose metabolism, glucose transport, glycolysis, redox modulation, feedback regulation, angiogenesis, promoting red blood cell maturation and oxygen transport, erythropoiesis, and iron metabolism. In some embodiments, the HIF-responsive gene is selected from the group consisting of glucose transporter 1 (GLUT1); glucose transporter 3 (GLUT3); pyruvate dehydrogenase kinase, isozyme 1 (PDK1); hexokinase 1 (HK1); hexokinase 2 (HK2); glyceraldehyde 3-phosphate dehydrogenase (GAPDH); 6-phosphofructo-2-kinase/fructose-2,6-bisphosphatase-3 (PFKBF3); 6-phosphofructo-2-kinase, liver type (PFKL); phosphoglycerate kinase 1 (PGK1); pyruvate kinase, muscle (PKM); lactate dehydrogenase A (LDHA); monocarboxylate transporter 4 (MCT4); Egl-9 family hypoxia-inducible factor 1 (EGLN1); Egl-9 family hypoxia-inducible factor 3 (EGLN3); vascular endothelial growth factor (VEGF); vascular endothelial growth factor receptor (VEGFR); endoglin (ENG); transforming growth factor, beta 3 (TGF-B3); adrenomedullin (ADM); nitric oxide synthase 2, inducible (NOS2); heme oxygenase 1 (HMOX1); erythropoietin (EPO); transferrin (TF); and transferrin receptor (TFRC).

In yet another embodiment, increasing the activity of a hypoxia response is done during normoxic conditions. In some embodiments, increasing the activity of a hypoxia response is not through stabilization or activation of HIF1α. In still another embodiment, increasing the activity of a hypoxia response comprises bypassing endogenous cellular oxygen sensing.

In some embodiments, the subject comprises mitochondria comprising one or more mitochondrial lesions or other lesions which impact mitochondrial respiratory chain function. In another embodiment, the one or more mitochondrial lesions may be introduced by oxidative stress. In other embodiments, the one or more mitochondrial lesions occur in a respiratory chain complex. In certain embodiments, the one or more mitochondrial lesions occur in a protein complex, wherein the protein complex is selected from the group consisting of: Complex I, Complex II, Complex III, Complex IV, Complex V, and ATP (adenosine triphosphate) Synthase.

In other embodiments, the method comprises inhibition of one or more proteins involved in the hypoxia response. In certain embodiments, inhibition of one or more proteins involved in a hypoxia response increases the activity of the hypoxia response. In some embodiments, the method comprises inhibition of PHD or VHL protein. In another embodiment, the PHD inhibitor is selected from the group consisting of 2-oxoglutarate analogs (also known as α-ketoglutarate), β-oxocarboxylic acids, and BAY-85-3934. In some embodiments, the PHD inhibitor is FG-4592 or roxadustat. One of skill in the art may use any PHD inhibitor or VHL inhibitor known in the art for use in methods disclosed herein. In yet another embodiment, the method comprises increasing the stability or the activation of hypoxia inducible transcription factor (HIF). In another embodiment, increasing the activity of the hypoxia response comprises increasing the stability or the activation of HIF proteins. In some embodiments, increasing the stability of HIF proteins is done during normoxic conditions.

In yet another embodiment, the mitochondrial disorder is a genetic disorder that affects the mitochondrial oxidative phosphorylation system. In some embodiments, the mitochondrial disorder affects one or more of the five respiratory chain complexes. In certain embodiments, the respiratory chain complexes is selected from the group consisting of Complex I (NADH-coenzyme Q reductase or NADH dehydrogenase), Complex II (succinate-coenzyme Q reductase or succinate dehydrogenase), Complex III (cytochrome bci complex or ubiquinone-cytochrome C oxidoreductase), Complex IV (cytochrome C oxidase), and Complex V (ATP synthase).

In still another embodiment, the subject has an age-associated disorder. In some embodiments, the age-associated disorder is selected from the group consisting of type 2 diabetes, neurodegeneration (e.g., Alzheimer's disease), sarcopenia (muscle loss), insulin resistance, peripheral neuropathy, muscle atrophy, deafness, atherosclerosis, cardiovascular disease, heart failure, chronic kidney disease, cancer, arthritis, cataracts, and osteoporosis. In other embodiments, the age-associated disorder is selected from the group consisting of type 2 diabetes, neurodegeneration and sarcopenia.

In another aspect, the current disclosure provides a method of increasing the activity of a hypoxia response in a subject in need thereof comprising increasing the stability or the activation of HIF proteins in the subject.

In yet another aspect, the current disclosure provides a method of treating or preventing mitochondrial dysfunction, an oxidative stress disorder, or an inflammatory disorder in a subject in need thereof comprising increasing cellular glycolysis in the subject. In some embodiments, increasing cellular glycolysis comprises activation of a gene involved in glycolysis. In certain embodiments, the gene involved in glycolysis is selected from the group consisting of hexokinase 1 (HK1); hexokinase 2 (HK2); glyceraldehyde 3-phosphate dehydrogenase (GAPDH); 6-phosphofructo-2-kinase/fructose-2,6-bisphosphatase-3 (PFKBF3); 6-phosphofructo-2-kinase, liver type (PFKL); phosphoglycerate kinase 1 (PGK1); and pyruvate kinase, muscle (PKM). In other embodiments, increasing cellular glycolysis is done during normoxic conditions. In still other embodiments, increasing cellular glycolysis comprises bypassing endogenous cellular oxygen sensing.

In still another aspect, the current disclosure provides a method of treating or preventing mitochondrial dysfunction, an oxidative stress disorder, or an inflammatory disorder in a subject in need thereof comprising suppressing cellular basal respiration in the subject. In some embodiments, the suppressing cellular basal respiration is done during normoxic conditions. In other embodiments, suppressing cellular basal respiration comprises bypassing endogenous cellular oxygen sensing.

In other embodiments, the treatment using one of the methods disclosed herein is during a period of cellular stress. In certain embodiments, the period of cellular stress corresponds to hypoxic conditions. In another embodiment, the treatment using one of the methods disclosed herein is during a period of high energy demand. In some embodiments, the period of high energy demand uses respiratory chain complexes to produce energy for a cell.

In some embodiments, the method of treatment or prevention of mitochondrial dysfunction, an oxidative stress disorder, or an inflammatory disorder in a subject in need thereof is applied over a period of time that can range, e.g., from 8 hrs/day (sleep period) to about 1 day to about 50 years, and more usually 1 week to about 25 years (e.g., 3 months, 6 months, 1 year, 5 years, and 10 years). In other embodiments, the treatment using one of the methods disclosed herein occurs over time and is a chronic treatment.

In some embodiments, the method of treatment, reduces or treats one or more symptoms of the mitochondrial disease. For example, symptoms mays include loss of motor control (e.g., ataxia (abnormal muscle coordination), dystrophic posturing, involuntary movements, and myoclonus), muscle weakness and pain (e.g., dystonia, hypotonia, lethargy, and myopathy), gastro-intestinal disorders and swallowing difficulties, poor growth, cardiac disease, liver disease, diabetes, respiratory complications (e.g., respiratory failure), seizures, dementia, coma, visual problems (e.g., eye muscle paralysis, nystagmus, ophthalmoplegia, optic atrophy, and pigmentary retinopathy (retinal color changes with loss of vision)), hearing problems (e.g., hearing loss), sensory neuropathy (nerve damage involving the sense organs), lactic acidosis, developmental delays and susceptibility to infection.

In other embodiments, mitochondrial disease causes cell injury or cell death of cells in the brain, heart, liver, skeletal muscles, kidneys, endocrine system, and respiratory system.

In some embodiments, a mitochondrial disorder involves a deficiency in one or more respiratory chain complexes including Complex I (NADH-coenzyme Q reductase or NADH dehydrogenase), Complex II (succinate-coenzyme Q reductase or succinate dehydrogenase), Complex III (cytochrome bci complex or ubiquinone-cytochrome C oxidoreductase), Complex IV (cytochrome C oxidase), and Complex V (ATP synthase). In other embodiments, a mitochondrial disorder involves one or more of the following diseases myopathy (muscle disease), mitochondrial encephalomyopathy (brain and muscle disease), fatal infantile multisystem disorder.

In some embodiments, a mitochondrial disorder is characterized by a mutation in a gene selected from the group consisting of AARS2, AASS, ABAT, ABCB6, ABCB7, ABCD1, ACACA, ACAD8, ACAD9, ACADM, ACADS, ACADSB, ACADVL, ACAT1, ACO2, ACSF3, ACSL4, ADCK3, ADCK4, AFG3L2, AGK, AGXT, AIFM1, AK2, ALAS2, ALDH18A1, ALDH2, ALDH3A2, ALDH4A1, ALDH5A1, ALDH6A1, ALDH7A1, AMACR, AMT, APOPT1, ATIC, ATP5A1, ATP5E, ATP6, ATP8, ATPAF2, ATXN2, AUH, BAX, BCKDHA, BCKDHB, BCKDK, BCS1L, BOLA3, C10orf2, C12orf65, CA5A, CARS2, CASP8, CAT, CEP89, CHCHD10, CISD2, CLPB, CLPP, COA5, COA6, COASY, COQ2, COQ4, COQ6, COQ9, COX1, COX10, COX14, COX15, COX2, COX20, COX3, COX412, COX6A1, COX6B1, COX7B, CPDX, CPS1, CPT1A, CPT2, CYB5A, CYB5R3, CYC1, CYCS, CYP11A1, CYP11B2, CYP24A1, CYP27A1, CYP27B1, CYTB, D2HGDH, DARS2, DBT, DGUOK, DHCR24, DHODH, DHTKD1, DIABLO, DLAT, DLD, DMGDH, DMPK, DNA2, DNAJC19, DNM1L, EARS2, ECHS1, ELAC2, ETFA, ETFB, ETFDH, ETHE1, FARS2, FASTKD2, FBXL4, FECH, FH, FKBP10, FOXRED1, FXN, GARS, GATM, GCDH, GCSH, GDAP1, GFER, GFM1, GK, GLDC, GLRX5, GLUD1, GLYCTK, GPI, GPX1, GRHPR, GTPBP3, HADH, HADHA, HADHB, HARS2, HCCS, HIBCH, HK1, HMBS, HMGCL, HMGCS2, HOGA1, HSD17B10, HSD17B4, HSPD1, HTRA2, IDH2, IDH3B, ISCA2, ISCU, IVD, KARS, KIF1B, KRT5, L2HGDH, LARS2, LIAS, LONP1, LRPPRC, LYRM4, LYRM7, MAOA, MARS2, MCCC1, MCCC2, MCEE, MFN2, MGME1, MICU1, MLH1, MLYCD, MMAB, MMACHC, MMADHC, MOCS1, MPC1, MPV17, MRPL12, MRPL3, MRPL44, MRPS16, MRPS22, mt-12S rRNA, mt-tRNATyr, mt-tRNATrp, mt-tRNAVal, mt-tRNAThr, mt-tRNASer1, mt-tRNASer2, mt-tRNAArg, mt-tRNAGln, mt-tRNAPro, mt-tRNAAsn, mt-tRNAMet, mt-tRNALeu1, mt-tRNALeu2, mt-tRNALys, mt-tRNAIle, mt-tRNAHis, mt-tRNAGly, mt-tRNAPhe, mt-tRNAGlu, mt-tRNAAsp, mt-tRNACys, mt-tRNAAla, MTFMT, MTO1, MTPAP, MUT, MUTYH, NAGS, NARS2, NCOA4, ND1, ND2, ND3, ND4, ND4L, ND5, ND6, NDUFA1, NDUFA10, NDUFA11, NDUFA12, NDUFA2, NDUFA4, NDUFA9, NDUFAF1, NDUFAF2, NDUFAF3, NDUFAF4, NDUFAF5, NDUFAF6, NDUFB11, NDUFB3, NDUFB9, NDUFS1, NDUFS2, NDUFS3, NDUFS4, NDUFS6, NDUFS7, NDUFS8, NDUFV1, NDUFV2, NFU1, NNT, NUBPL, OAT, OGDH, OGG1, OPA1, OPA3, OTC, OXCT1, PAM16, PANK2, PARK7, PARS2, PC, PCCA, PCCB, PCK2, PDHA1, PDHB, PDHX, PDP1, PDSS1, PDSS2, PET100, PEX11B, PEX6, PHYH, PINK1, PNPO, PNPT1, POLG, POLG2, PPM1K, PPOX, PRODH, PTRH2, PTS, PUS1, PYCR1, QDPR, RARS, RARS2, RMND1, RPL35A, RPS14, RRM2B, SARS2, SCO1, SCO2, SCP2, SDHA, SDHAF1, SDHAF2, SDHB, SDHC, SDHD, SECISBP2, SERAC1, SFXN4, SLC16A1, SLC19A3, SLC25A1, SLC25A12, SLC25A13, SLC25A15, SLC25A19, SLC25A20, SLC25A22, SLC25A3, SLC25A38, SLC25A4, SNAP29, SOD1, SPG7, SPR, SPTLC2, STAR, SUCLA2, SUCLG1, SUOX, SURF1, TACO1, TARS2, TAZ, TCIRG1, TIMM8A, TK2, TMEM126A, TMEM70, TMLHE, TPI1, TRIT1, TRMU, TRNT1, TSFM, TTC19, TUBB3, TUFM, TYMP, UNG, UQCR10, UQCRB, UQCRC2, UQCRQ, VARS2, WDR81, WFS1, XPNPEP3, and YARS2. In some embodiments, a subject has been identified as having a genetic mutation associated with onset of a mitochondrial disorder (e.g., a mutation in one of the genes identified above) and treatment is initiated before the onset of symptoms of the disorder.

In some embodiments, a mitochondrial disorder is characterized by a point mutation in the mitochondrial DNA (mtDNA), deletion within the mtDNA, duplication within the mtDNA, or depletion of the mtDNA.

In some embodiments, a mitochondrial disorder is Kearns-Sayre syndrome (KSS), Leber's hereditary optic neuropathy (LHON), myoclonic epilepsy ragged red fiber syndrome (MERRF), mitochondrial encephalopathy, lactic acidosis, and stroke (MELAS) syndrome, sensory ataxic neuropathy, dysarthria, and ophthalmoparesis (SANDO) syndrome, maternally inherited Leigh syndrome (MILS), myopathy and external ophthalmoplegia, neuropathy, gastrointestinal encephalopathy (MNGIE) syndrome, Leigh syndrome, maternally inherited diabetes and deafness (MIDD) syndrome, Alpers-Huttenlocher syndrome, Sengers syndrome, mitochondrial myopathy, lactic acidosis and sideroblastic anemia (MLASA), chronic progressive external ophthalmoplegia (CPEO), autosomal dominant progressive external ophthalmoplegia (AdPEO), neuropathy, ataxia, retinitis pigmentosa (NARP) syndrome, GRACILE syndrome, diabetes insipidus, diabetes mellitus, optic atrophy, and deafness (DIDMOAD) syndrome, or Pearson's syndrome.

In some embodiments, a mitochondrial disorder presents with one or more of gray matter disease, white matter disease, seizures, migraines, ataxia, stroke, stroke-like episodes, deafness, optic neuropathy, peripheral neuropathy, retinopathy, external opthalmoplegia, liver failure, kidney failure, pancreatic exocrine dysfunction, intestinal pseudoobstruction, anemia, skeletal muscle myopathy, cardiomyopathy, cardiac conduction defects, short stature, hypogonadism, immune dysfunction, or metabolic acidosis.

In some embodiments, the mitochondrial disorder is diagnosed by an algorithm selected from the group consisting of the Bernier criteria (Bernier et al., "Diagnostic criteria for respiratory chain disorders in adults and children," Neurology, 59(9):1406-11, 2002), the Morava criteria (Morava et al., "Mitochondrial disease criteria: diagnostic applications in children," Neurology, 67(10):1823-6, 2006), and Consensus from the Mitochondrial Medicine Society (Parikh et al., "Diagnosis and management of mitochondrial disease: a consensus statement from the Mitochondrial Medicine Society," Genetics in Medicine, 17(9):689-701, 2015).

In some embodiments, a subject exhibits mitochondrial dysfunction associated with aging. The subject can be, e.g., at least 65 years of age, at least 70 years of age, at least 75 years of age, or at least 80 years of age.

In some embodiments, the subject is treated to prevent (completely or partially) the occurrence of mitochondrial dysfunction associated with aging. The subject can be, e.g., at least 15 years of age, at least 20 years of age, at least 25 years of age, at least 30 years of age, at least 35 years of age, or at least 40 years of age. The subject in these embodiments need not exhibit mitochondrial dysfunction or other form of evident disease.

In some embodiments, a subject exhibits mitochondrial dysfunction that occurs in response to an environmental insult such as ingestion of antibiotics (e.g., tetracycline, chloramphenicol, or aminoglycosides), antivirals (e.g., stavudine), pesticides (e.g., rotenone), or licit drugs (e.g., MPTP) that are toxic to mitochondria.

In some embodiments, a subject has an oxidative stress disorder. Examples of oxidative stress disorders include Parkinson's disease, Alzheimer's disease, amyotrophic lateral sclerosis, Huntington's disease, multiple sclerosis, Asperger syndrome, attention deficit hyperactivity disorder, diabetes, cardiovascular disease, cancer, Lafora disease, atherosclerosis, heart failure, myocardial infarction, fragile X syndrome, sickle cell disease, lichen planus, vitiligo, and autism.

In some embodiments, a subject has an inflammatory disorder. Examples of inflammatory disorders include rheumatoid arthritis, psoriatic arthritis, ankylosing spondylitis, inflammatory bowel disease (e.g., ulcerative colitis and Crohn's disease), psoriasis, inflammatory myositis, Langerhans-cell histiocytosis, adult respiratory distress syndrome, Wegener's granulomatosis, vasculitis, cachexia, stomatitis, idiopathic pulmonary fibrosis, dermatomyositis, polymyositis, non-infectious scleritis, chronic sarcoidosis with pulmonary involvement, myelodysplastic syndrome, moderate to severe chronic obstructive pulmonary disease, and giant cell arteritis.

In a further aspect, the current disclosure provides a method of screening for a compound that increases the activity of a hypoxia response comprising a) administering a candidate compound to a first set of one or more cells with a compromised function of the mitochondrial respiratory chain;

b) measuring the growth of the first set of one or more cells; and c) comparing the growth of the first set of one or more cells to the growth of a second set of one or more cells, wherein the second set of one or more cells also have compromised function of the mitochondrial respiratory chain, but have not been administered the candidate compound, wherein if the growth of the first set of cells is greater than the growth of the second set of cells then the candidate compound increases the activity of a hypoxia response.

In some embodiments, cell growth is stunted or arrested when respiratory chain complexes are inhibited for most cell lines. In other embodiments, inhibition of one of the following respiratory chain complexes: Complex I, Complex III, or Complex V stunts cell growth in most cell lines. In certain embodiments, inhibition of Complex I, Complex III, or Complex V stops cell growth in a cell line. In still other embodiments, the methods of screening disclosed herein use one or more cells that are HT-29 cells, HEK 293 cells, or K562 cells.

In another embodiment, a compromised function of the mitochondrial respiratory chain comprises the presence of genetic defects in one or more respiratory chain complexes, triggering a mitochondrial lesion, or administering an inhibitor of one or more respiratory chain complexes. In other embodiments, the compromised function of the mitochondrial respiratory chain comprises an inhibitor of one or more respiratory chain complexes. In still another embodiment, the compromised function of the mitochondrial respiratory chain comprises administration of antimycin to the one or more cells in the presence of pyruvate. In yet another embodiment, the compromised function of the mitochondrial respiratory chain further comprises the reduction of or removal of pyruvate.

In other embodiments, cell growth is reduced by administering a Complex I inhibitor, a Complex III inhibitor, or a Complex V inhibitor. In another embodiment, the compromised function of the mitochondrial respiratory chain comprises an inhibition selected from the group consisting of: Complex III Inhibition, Complex I Inhibition, Complex V Inhibition, and ATP (adenosine triphosphate) Synthase Inhibition. In still other embodiments, the compromised function of the mitochondrial respiratory chain comprises administering a Complex I inhibitor, a Complex III inhibitor, or a Complex V inhibitor. In another embodiment, the Complex I inhibitor is selected from the group consisting of acetogenins, reduced nicotinamide adenine dinucleotide (NADH) analogs, and metformin. In yet another embodiment, the Complex I inhibitor is selected from the group consisting of annonacin, bullatacin, rolliniastatin-2, uvaricin, adenosine diphosphate ribose, piericidin, rotenone, and metformin. In still another embodiment, the Complex III inhibitor is selected from the group consisting of $Q_i$ site inhibitors and $Q_o$ site inhibitors. In a further embodiment, the Complex III inhibitor is selected from the group consisting of Antimycin, myxothiazol, stigmatellin, and strobilurin derivatives. In some embodiments, the ATP synthase inhibitor is selected from the group consisting of oligomycins, α-helical basic peptide inhibitors, catechins, catecholestrogens, flavones, polyketide inhibitors, stilbenes, tentoxin and derivatives, and nucleotide analogs. In some embodiments, the ATP synthase inhibitor is selected from the group consisting of oligomycin, melittin, epicatechin, epicatechin gallate, epigallocatechin gallate, 4-hydroxyestradiol, 2-hydroxyestradiol, quercetin, morin, kaempferol, genistein, peliomycin, venturicidin A, venturicidin B, venturicidin X, ossamycin, resveratrol, piceatannol, diethylstilbestrol, tentoxin, GTP, FTP, and TNP-ATP.

In another aspect, the current disclosure provides a method of screening for targets for the modulation of mitochondrial respiratory chain function by genetic engineering techniques. In one aspect, the genetic engineering technology comprises a recombinant CRISPR-Cas expression system. In one embodiment, the Cas protein is complexed with a sgRNA as provided herein and in the art. In one embodiment, the method of screening for targets for modulation of mitochondrial respiratory chain function comprising a) administering to a first set of one or more cells one or more sgRNAs targeting at least one gene in the human genome;

b) compromising the function of the mitochondrial respiratory chain in the first set of one or more cells;

c) measuring the relative enrichment of sgRNAs in the first set of one or more cells; and d) comparing the corresponding enrichment of sgRNAs of the first set of one or more cells to the enrichment in a second set of one or more cells, wherein the second set of one or more cells have been administered the same one or more sgRNAs, but have less compromised function of the mitochondrial respiratory chain, wherein if the relative enrichment of a sgRNA in the first set of cells is greater than the corresponding enrichment in the second set of cells then the gene is a target for the modulation of cellular or whole body response to mitochondrial respiratory chain (dys)function.

In another embodiment, compromising the function of the mitochondrial respiratory chain comprises introducing genetic defects in one or more respiratory chain complexes, triggering a mitochondrial lesion, or administering an inhibitor of one or more respiratory chain complexes. In other embodiments, the compromise of function of the mitochondrial respiratory chain comprises administration of an inhibitor of one or more respiratory chain complexes. In still another embodiment, the compromise of function of the mitochondrial respiratory chain comprises administration of antimycin to the one or more cells in the presence of pyruvate. In yet another embodiment, the compromise of function of the mitochondrial respiratory chain further comprises the reduction of or removal of pyruvate.

In yet another aspect, the current disclosure provides a composition comprising a nucleic acid molecule comprising a sequence selected from the group consisting of:

AGTACCTGGCAGTGTGATAT (SEQ ID NO: 1)

CAGGTCGCTCTACGAAGATC (SEQ ID NO: 2)

CGCGCGTCGTGCTGCCCGTA (SEQ ID NO: 3)

GTGCCATCTCTCAATGTTGA (SEQ ID NO: 4)

TGTCCGTCAACATTGAGAGA (SEQ ID NO: 5)

wherein the nucleic acid molecule is functionally integrated with a viral vector.

A physician or veterinarian having ordinary skill in the art can readily determine and prescribe the effective amount required by the methods of treatment. For example, the physician or veterinarian could start doses of the inhibitors or sequences of the invention employed in the methods at levels lower than that required in order to achieve the desired therapeutic effect and gradually increase the dosage until the desired effect is achieved.

It will be understood by those having ordinary skill in the art that the specific dose level and frequency of dosage for any particular patient or subject may be varied and will depend upon a variety of factors including the efficacy of the specific method employed, the metabolic stability and length of action of that method, the age, body weight, general health, gender, diet, and the severity of the particular mitochondrial disorder being treated. In addition specific dose level and frequency of dosage for any particular patient also may depend on factors including, but not limited to, other medications, allergies, and prior experiences with treatments. For example, some patients may be treated using methods of this disclosure over a period of years if the mitochondrial disorder is a chronic condition.

In additional embodiments, assay screening kits are provided. The kit includes a container for the screening assay. An instruction for the use of the assay and the information about the screening method are to be included in the kit. In some embodiments, the kit may also contain a Complex I inhibitor, a Complex III inhibitor, or a Complex V inhibitor to mimic a mitochondrial respiratory chain disorder. In other embodiments, the kit may also contain sgRNAs having a nucleic acid sequence comprising one or more sequences targeting at least one gene in the human genome.

C. Hypoxia Therapy

Mitochondrial dysfunction, an oxidative stress disorder, or an inflammatory disorder can be treated or prevented by administering to a subject by inhalation a therapeutically effective amount of a therapeutic gas comprising between 5 to 20% $O_2$. A hypoxia induction system can be used to prepare the therapeutic gas that is administered to the subject.

In a first example, a hypoxia induction system contains a first container containing a first gas comprising nitrogen and a second container containing a second gas comprising oxygen, and the oxygen-depleted air delivered to the subject is prepared by mixing the first gas and the second gas.

In a second example, a hypoxia induction system intakes ambient air, reduces the oxygen content of the intake air, to produce the oxygen-depleted air that is delivered to the subject. Colorado Altitude Training (CAT) provides a portable enclosure system that produces hypoxic air by this mechanism. CAT uses a high-flow hypoxic air delivery unit and a semi-sealed enclosure. The air unit draws in ambient room air and separates the oxygen molecules from the nitrogen molecules, creating the hypoxic or oxygen reduced air. Simulated altitudes of up to 14,500 feet can be achieved, and can be controlled to within 100 feet accuracy using CAT's digital control system. Hypoxico Altitude Training Systems devices generate hypoxic air in a manner similar to the CAT system. Simulated altitudes of about 21,500 feet can be achieved with the Hypoxico Altitude Training Systems.

In a third example, a hypoxia induction system intakes ambient air, adds nitrogen to the intake air, to produce the oxygen-depleted air that is delivered to the subject. The nitrogen can provided from, e.g., liquid nitrogen, cylinders of highly purified nitrogen (e.g., 100% nitrogen), or cylinders containing nitrogen (e.g., 80-95%) and oxygen (e.g., 5-20%). Nitrogen used to produce oxygen-depleted air can optionally be produced by pressure swing adsorption (PSA). Under high pressure, gases tend to be adsorbed to solid surfaces. When the pressure is reduced, the gas is desorbed. If air is passed under pressure through a vessel containing a carbon molecular sieve, oxygen gas is adsorbed and gas enriched in nitrogen and depleted in oxygen is produced. Dual step PSA can be used to produce a highly pure nitrogen gas: first, compressed air is forced through a carbon molecular sieve to produce nitrogen at a purity of approximately 98%; second, the nitrogen produced in the first step is forced into a second carbon molecular sieve and the nitrogen gas reaches a purity up to 99.999%. This nitrogen gas can be combined with ambient air to produce oxygen-depleted air that is delivered to the subject. Alternatively, if air is passed under pressure through a vessel containing an adsorbent bed of zeolite that attracts nitrogen more strongly than it does oxygen, part or all of the nitrogen will stay in the bed. When the bed reaches the end of its capacity to adsorb nitrogen, the pressure can be reduced to release the adsorbed nitrogen. This released nitrogen can be combined with ambient air to produce oxygen-depleted air that is delivered to the subject.

The therapeutic gas delivered to the subject can contain between 5 to 20% $O_2$. The proportion of oxygen in the therapeutic gas can vary based upon factors including the age of the subject, the condition treated, and the duration of the hypoxic treatment. For example, the therapeutic gas can contain between 5 to 20% $O_2$, between 6 to 18% $O_2$, between 7 to 17% $O_2$, between 8 to 16% $O_2$, between 9 to 15% $O_2$, between 10 to 15% $O_2$, between 10 to 14% $O_2$, between 10 to 13% $O_2$, between 10 to 12% $O_2$, or between 10 to 11% $O_2$. In some embodiments, the therapeutic gas contains about 5% $O_2$, about 6% $O_2$, about 7% $O_2$, about 8% $O_2$, about 9% 02, about 10% $O_2$, about 11% $O_2$, about 12% $O_2$, about 13% $O_2$, about 14% $O_2$, about 15% $O_2$, about 16% $O_2$, about 17% $O_2$, or about 18% $O_2$.

The therapeutic gas can be administered to the subject by devices including but not limited to nasal prongs, a face mask, an enclosed tent or chamber (completely or semi-sealed), an intra-tracheal catheter, an endotracheal tube, or a tracheostomy tube. The use of nasal prongs or a face mask allow for greater mobility of the subject while being treated with the therapeutic gas.

The therapeutic gas can optionally be inhaled by the subject continuously over the course of a variety of time periods (e.g., at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 1 hour, at least 2 hours, at least 4 hours, at least 8 hours, at least 12 hours, at least 24 hours, at least 48 hours, or longer). In some instances, administration of the therapeutic gas is intermittent (e.g., only during inspiration to save gas (sensing inspiration by a variety of methods, temperature, pressure, etc.)) or only for a few hours each day, wherein the therapeutic gas is inhaled (e.g., for a period of time specified above), followed by breathing ambient air, which is then followed by one or more additional periods of breathing the therapeutic gas.

The therapeutic gas can optionally be administered to a subject during sleep. This can be achieved by, for example, positioning a tent over a bed or placing a bed within an enclosed chamber. For children or infants, a tent can be positioned over a crib or a crib can be placed within an enclosed chamber.

A subject treated with the therapeutic gas can be monitored to measure the effects mediated by the treatment. For example, arterial oxygen saturation ($SpO_2$) can be measured in the subject one or more times (continuously or intermittently) after administration of the therapeutic gas to the subject. The measured $SpO_2$ value can be used to feedback and adjust (e.g. automatically adjust) the oxygen content of the administered therapeutic gas so as to maintain $SpO_2$ in the subject in the range of 50-90% (e.g., 60-90%, 70-90%, 75-90%, 80-90%, 85-90%, or about 85%). In addition or alternatively, arterial partial oxygen pressure ($PaO_2$) can be measured in the subject one or more times (continuously or intermittently) after administration of the therapeutic gas to the subject. The measured $PaO_2$ value can be used to feedback and adjust (e.g. automatically adjust) the oxygen content of the administered therapeutic gas so as to maintain $PaO_2$ in the subject in the range of 25 mm Hg to 90 mm Hg (e.g., 25 mm Hg to 70 mm Hg, 25 mm Hg to 60 mm Hg, 25 mm Hg to 55 mm Hg, 25 mm Hg to 45 mm Hg, 25 mm Hg to 40 mm Hg, 25 mm Hg to 35 mm Hg, 35 mm Hg to 70 mm Hg, 35 mm Hg to 60 mm Hg, 45 mm Hg to 60 mm Hg, 50 mm Hg to 60 mm Hg, 55 mm Hg to 60 mm Hg, or about 55 mm Hg). In some embodiments, $SpO_2$ and $PaO_2$ are both measured in the subject one or more times (continuously or intermittently) after administration of the therapeutic gas to the subject. The measured $SpO_2$ and $PaO_2$ values can be used to feedback and adjust (e.g. automatically adjust) the oxygen content of the administered therapeutic gas so as to maintain $SpO_2$ and $PaO_2$ in the subject in the range of 50-90% $SpO_2$ and 25 mm Hg to 70 mm Hg $PaO_2$ (e.g., 80-90% $SpO_2$ and 50 mm Hg to 60 mm Hg $PaO_2$, 85-90% $SpO_2$ and 55 mm Hg to 60 mm Hg $PaO_2$, or about 85% $SpO_2$ and about 55 mm Hg $PaO_2$).

Blood hematocrit and/or circulating hemoglobin levels can be measured in a subject one or more times after administration of the therapeutic gas to the subject, wherein the detection of an increase in blood hematocrit and/or an increase in circulating hemoglobin levels after initiation of the treatment indicates that the treatment is having its desired effect. A decision of whether or how to continue the treatment can be based upon the measured blood hematocrit and/or circulating hemoglobin levels. For example, if the measured blood hematocrit and/or circulating hemoglobin levels exceed a pre-established target level, then the treatment may be terminated or the oxygen content of the administered therapeutic gas may be increased. In another example, if the measured blood hematocrit and/or circulating hemoglobin levels are below a pre-established target level, then the duration of the treatment may be extended and/or the oxygen content of the therapeutic gas may be decreased.

A system for treatment or prevention according to the methods described herein can optionally contain: (i) an enclosed tent or chamber or a breathing apparatus; (ii) a hypoxia induction system that delivers oxygen-depleted air to the enclosed tent or chamber or the breathing apparatus, wherein the oxygen-depleted air comprises between 5 to 20% $O_2$ (or any of the oxygen concentrations described herein); and (iii) a device (such as a pulse oximeter) that measures $SpO_2$ in a subject breathing air within the enclosed tent or chamber or from the breathing apparatus, wherein the system adjusts the oxygen content of the oxygen-depleted air delivered to the enclosed tent or chamber or the breathing apparatus based upon the $SpO_2$ measured by the device such that $SpO_2$ in the subject is maintained within the range of 50% to 90% (or any of the $SpO_2$ target ranges or values described herein).

A system for treatment or prevention according to the methods described herein can optionally contain: (i) an enclosed tent or chamber or a breathing apparatus; (ii) a hypoxia induction system that delivers oxygen-depleted air to the enclosed tent or chamber or the breathing apparatus, wherein the oxygen-depleted air comprises between 5 to 20% $O_2$ (or any of the oxygen concentrations described herein); and (iii) a device that measures $PaO_2$ in a subject breathing air within the enclosed tent or chamber or from the breathing apparatus, wherein the system adjusts the oxygen content of the oxygen-depleted air delivered to the enclosed tent or chamber or the breathing apparatus based upon the $PaO_2$ measured by the device such that $PaO_2$ in the subject is maintained within the range of 25 mm Hg to 90 mm Hg (or any of the $PaO_2$ target ranges or values described herein).

Mitochondrial dysfunction, an oxidative stress disorder, or an inflammatory disorder can also be treated or prevented by causing a subject to breathe a therapeutically effective amount of air in a hypobaric chamber. In some instances, the hypobaric chamber has an atmospheric pressure equivalent to that between 1,500 meters to 10,000 meters above sea level (e.g., equivalent to 1,500 meters to 10,000 meters above sea level, equivalent to 2,000 meters to 8,000 meters above sea level, equivalent to 2,000 meters to 7,000 meters above sea level, equivalent to 2,000 meters to 6,000 meters above sea level, equivalent to 2,000 meters to 5,000 meters above sea level, equivalent to 2,000 meters to 4,000 meters above sea level, equivalent to 2,000 meters to 3,000 meters above sea level, equivalent to 2,000 meters to 2,500 meters above sea level, equivalent to 3,000 meters to 7,000 meters above sea level, equivalent to 3,000 meters to 6,000 meters above sea level, equivalent to 3,000 meters to 5,000 meters above sea level, equivalent to 3,000 meters to 4,000 meters above sea level, equivalent to 4,000 meters to 7,000 meters above sea level, equivalent to 4,000 meters to 6,000 meters above sea level, equivalent to 4,000 meters to 5,000 meters above sea level, equivalent to 5,000 meters to 8,000 meters above sea level, equivalent to 5,000 meters to 7,000 meters above sea level, equivalent to 5,000 meters to 6,000 meters above sea level, equivalent to 6,000 meters to 8,000 meters above sea level, equivalent to 6,000 meters to 7,000 meters above sea level, or equivalent to 7,000 meters to 8,000 meters above sea level).

In some subjects, such as some children or newborns, hypoxic breathing according to a method described herein may have adverse effects, such as causing pulmonary vasoconstriction, pulmonary hypertension, or shunting via the ductus arteriosus or a patent foramen ovale. To assist in dilating the pulmonary circulation and avoiding, or reducing the occurrence of, or alleviating potential adverse effects of hypoxic breathing, gaseous nitric oxide can optionally be administered to a subject in combination with breathing a therapeutic gas or breathing air in a hypobaric chamber to produce systemic hypoxia according to a method of treatment or prevention described herein. See Frostell et al. (1993) Anesthesiology 78:427-35. In embodiments where a subject is administered a therapeutic gas with reduced oxygen content, nitric oxide can optionally be administered within the therapeutic gas having reduced oxygen content. In some embodiments, lower body $SpO_2$ (e.g., toe) is measured in a subject (e.g., a child or infant) and nitric oxide is added to the inhaled therapeutic gas in an amount that causes the lower body $SpO_2$ to increase so as to decrease or eliminate the difference between lower body $SpO_2$ and upper body $SpO_2$ (e.g., as measured in a finger or ear).

Methods for safe and effective administration of nitric oxide are described in, e.g., Zapol, U.S. Pat. No. 5,570,683; Zapol et al., U.S. Pat. No. 5,904,938; Bach et al., U.S. Published Application No. 20030039638; Higenbottam, U.S. Pat. No. 5,839,433; and Frostell et al. (1991) *Circulation* 83:2038. Pharmaceutical grade nitric oxide for inhalation is available commercially (INOmax™, Mallinckrodt Pharmaceuticals).

The concentration of gaseous nitric oxide in the therapeutic gas administered to the subject can be, for example, at least 5 ppm, at least 10 ppm, at least 20 ppm, at least 40 ppm, at least 50 ppm, at least 80 ppm, at least 100 ppm, at least 200 ppm, at least 300 ppm, or at least 500 ppm. In some embodiments, the concentration of gaseous nitric oxide in the therapeutic gas is in the range of 0.5 ppm to 500 ppm (e.g., 0.5 ppm to 200 ppm, 0.5 ppm to 80 ppm, 1 ppm to 200 ppm, 1 ppm to 100 ppm, 1 ppm to 50 ppm, or 5 ppm to 40 ppm).

Gaseous nitric oxide can be administered by inhalation from a source of stored, compressed nitric oxide gas. The source of nitric oxide can be 100% nitric oxide, or diluted with $N_2$ or any other inert gas (e.g., helium). The nitric oxide can be obtained and stored as a mixture free of any contaminating $O_2$ or higher oxides of nitrogen, because such higher oxides of nitrogen (which can form by reaction of $O_2$ with nitric oxide) are potentially harmful to lung tissues. If desired, purity of the nitric oxide may be demonstrated with chemiluminescence analysis, prior to administration to a patient. Chemiluminescence $NO$—$NO_x$ analyzers are commercially available (e.g., Model 14A, Thermo Environmental Instruments, Franklin, Mass.). The $NO$—$N_2$ mixture may be blended with $O_2$ or an $O_2$-containing gas such as air through, for example, calibrated rotameters which have been validated previously with a spirometer. The final concentration of nitric oxide in the breathing mixture may be verified with a chemical or chemiluminescence technique (see, e.g., Fontijin et al., *Anal. Chem.* 42:575 (1970)). Nitric oxide gas may also be mixed with room air, using a standard low-flow blender (e.g., Bird Blender, Palm Springs, Calif.). Nitric oxide may be generated from a mixture of $N_2$ and $O_2$ (i.e., air) by using an electric plasma nitric oxide generator. Such a generator is described in Zapol, U.S. Pat. No. 5,396,882 and US published application number 20160030699.

Xenon upregulates hypoxia inducible factor 1 alpha and can be used to treat mitochondrial dysfunction, an oxidative stress disorder, or an inflammatory disorder according to the methods described herein. In some embodiments xenon can be administered to a subject in combination with breathing a reduced oxygen content therapeutic gas or breathing air in a hypobaric chamber according to a method of treatment or prevention described herein. In embodiments where a subject is administered a therapeutic gas with reduced oxygen content, xenon can optionally be administered within the therapeutic gas. The concentration of xenon (an anesthetic gas with therapeutic properties in ischemia-reperfusion) in the therapeutic gas administered to the subject can be, for example, 20-70% (e.g., 30-60%, 30-50%, 40-50%, 40-50%, about 40%, or about 45%).

D. Pharmaceutical Compositions

As used herein the term "pharmaceutical composition" refers to a preparation of one or more of the components described herein, or physiologically acceptable salts or prodrugs thereof, with other chemical components such as physiologically suitable carriers and excipients. The purpose of a pharmaceutical composition is to facilitate administration of a compound to an organism. The term "prodrug" refers a precursor compound that can hydrolyze, oxidize, or otherwise react under biological conditions (in vitro or in vivo) to provide the active compound.

The term "excipient" refers to an inert or inactive substance added to a pharmaceutical composition to further facilitate administration of a compound. Non-limiting examples of excipients include calcium carbonate, calcium phosphate, various sugars and types of starch, cellulose derivatives, gelatin, vegetable oils and polyethylene glycols.

The pharmaceutical compositions of the present invention PHD inhibitors selected from the group consisting of 2-oxoglutarate analogs (also known as α-ketoglutarate), β-oxocarboxylic acids, and BAY-85-3934. In some embodiments, the PHD inhibitor is FG-4592 or roxadustat. Pharmaceutical compositions can be formulated into a single dosage form. In certain embodiments, this dosage form is an oral dosage form. This oral dosage form can be in the form of tablets, pills, dragees, capsules, liquids (aqueous or non-aqueous solutions), gels, syrups, slurries, gelcaps, lozenges, suspensions, and the like, for oral ingestion by a patient. In certain embodiments, one or more of the pharmaceutical compositions are in a slow release composition or have been formulated to affect release from the oral dosage form. In other embodiments, these dosage forms can be administered by any method known in the art including intravenously and intraperitoneally.

The pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or by lyophilizing processes.

The compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

The term "administration" or any lingual variation thereof as used herein is meant any way of administration. The pharmaceutical composition may be administered in one therapeutic dosage form or in two separate therapeutic dosages such as in separate capsules, tablets or injections. In the case of the two separate therapeutic dosages, the administration may be such that the periods between the administrations vary or are determined by the practitioner. It is however preferred that the second drug is administered within the therapeutic response time of the first drug. The multiple therapeutic dosage forms may be administered either at the same time, or separately, or sequentially, according to the invention, do not represent a mere aggregate of known agents, but a new combination with the valuable property that the effectiveness of the treatment is achieved at a much lower dosage of said at least one additional drug.

The pharmaceutical compositions of the present invention may be administered by any convenient route, for example, by infusion or bolus injection, by absorption through epithelial or mucocutaneous linings (e.g., oral mucosa, rectal and intestinal mucosa, etc.) and may be administered together with any other therapeutic agent. Administration can be systemic or local.

Various delivery systems are known, e.g., encapsulation in liposomes, microparticles, microcapsules or capsules that may be used to administer the compositions of the invention. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the cars, nose, eyes, or skin. The preferred mode of administration is left to the discretion of the practitioner, and will depend in part upon the site of the medical condition (such as the site of cancer) and the severity of thereof.

For example, for injection the composition of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the composition can be formulated readily by combining the active components with any pharmaceutically acceptable carriers known in the art. Such "carriers" may facilitate the manufacture of such as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum, methyl cellulose, hydroxypropylmethyl-cellulose, sodium carbomethylcellulose, and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active components may be dissolved or suspended in suitable liquids, such as fatty oils, liquid paraffin, or liquid polyethylene glycols.

Dyestuffs or pigments may be added to the tablets or dragee coatings for identification or to characterize different dosages or dosage forms. In addition, stabilizers may be added.

Pharmaceutical compositions for parenteral administration include aqueous solutions of the active preparation in a water-soluble form. Additionally, suspensions of the active preparation may be prepared as oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl, cellulose, sorbitol or dextran. Optionally, the suspension may also contain suitable stabilizers or agents, which increase the solubility of the compounds, to allow for the preparation of highly concentrated solutions.

Alternatively, the composition may be in a powder form for constitution before use with a suitable vehicle, e.g., sterile, pyrogen-free water. The exact formulation, route of administration and dosage may be chosen by the physician familiar with the patient's condition. (See for example Fingl, et al., 1975, in "The Pharmacological Basis of Therapeutics", Chapter I, p. 1). Depending on the severity and responsiveness of the condition treated, dosing can also be a single administration of a slow release composition, with course of treatment lasting from several days to several weeks or until cure is effected or diminution of the disease state is achieved.

The following examples are provided to further elucidate the advantages and features of the present application, but are not intended to limit the scope of the application. The examples are for the illustrative purposes only.

EXAMPLES

Example 1: Mitochondrial Disease Model

Figure 3:
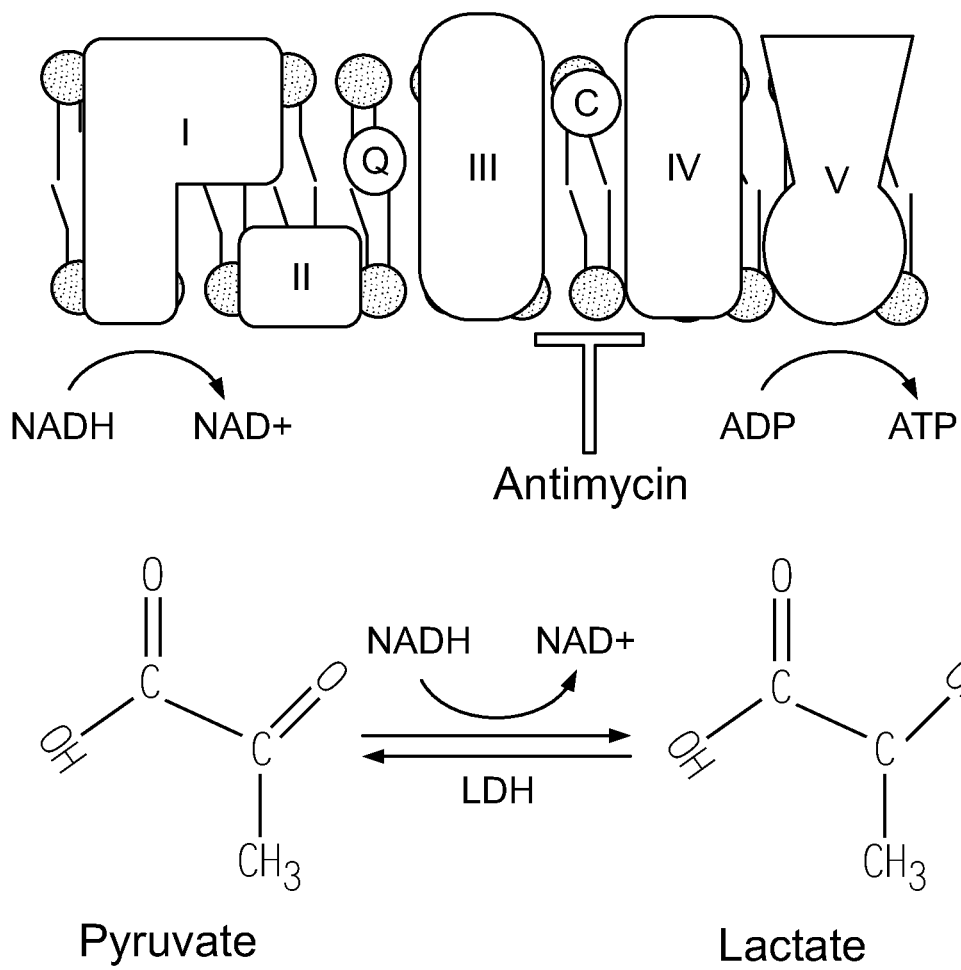
FIG. 3 shows a schematic representation of the effect of Antimycin on the mitochondrial respiratory chain.
Figure 4:
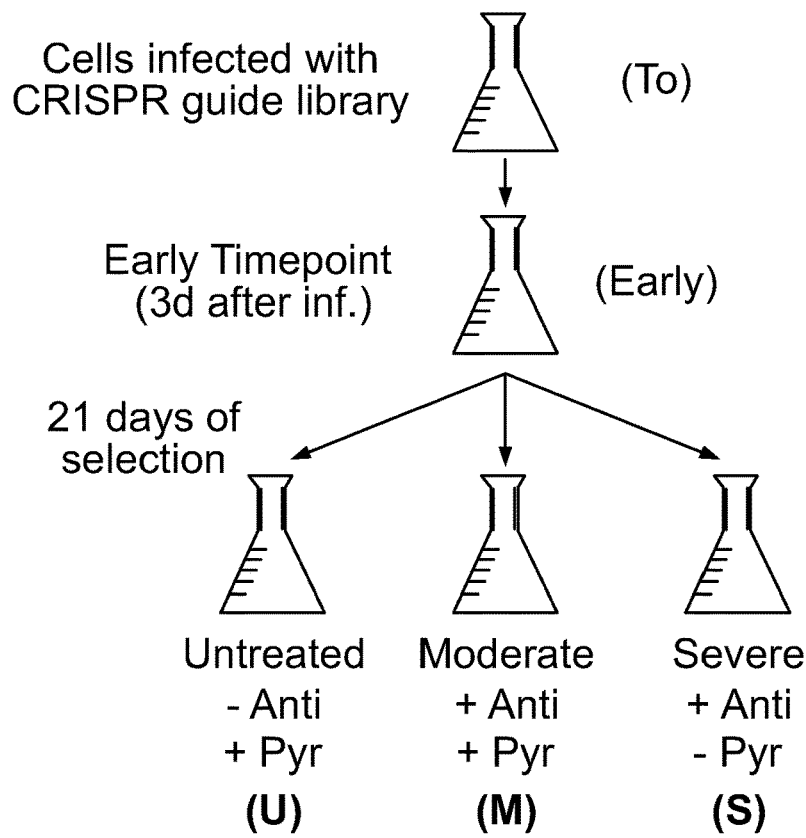
FIG. 4 shows a schematic representation of the CRISPR screen, wherein cells were divided into groups of untreated (U), moderate (M), and severe (S).
Figure 5:
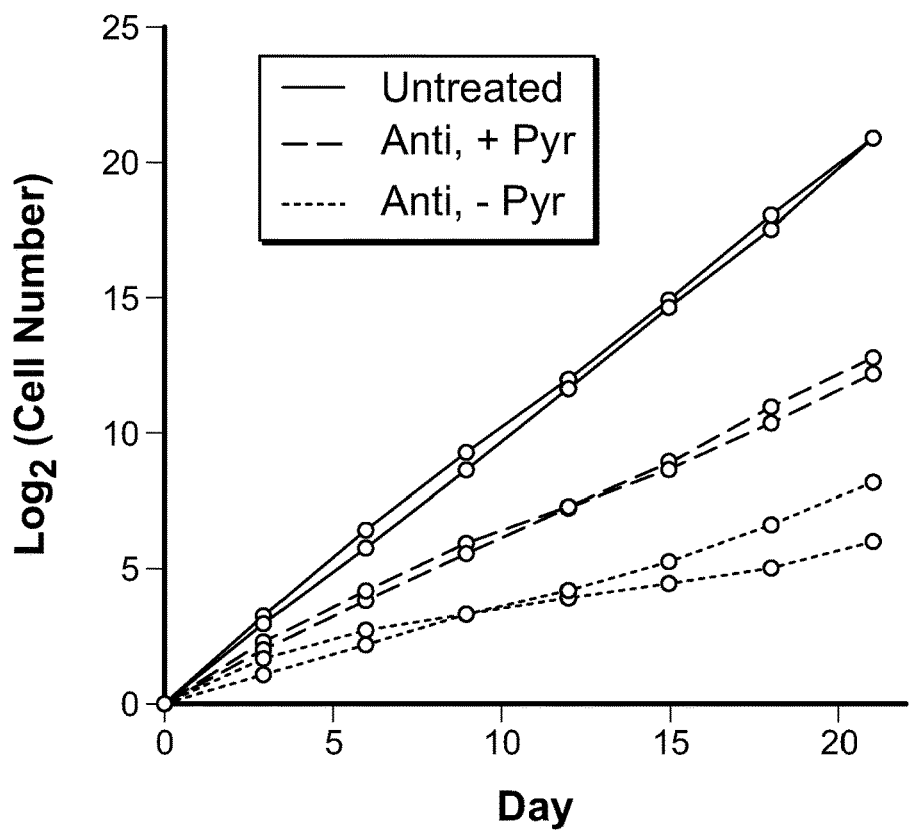
FIG. 5 shows the relative growth of cells in a mitochondrial respiratory chain disorder model.
Figure 6:
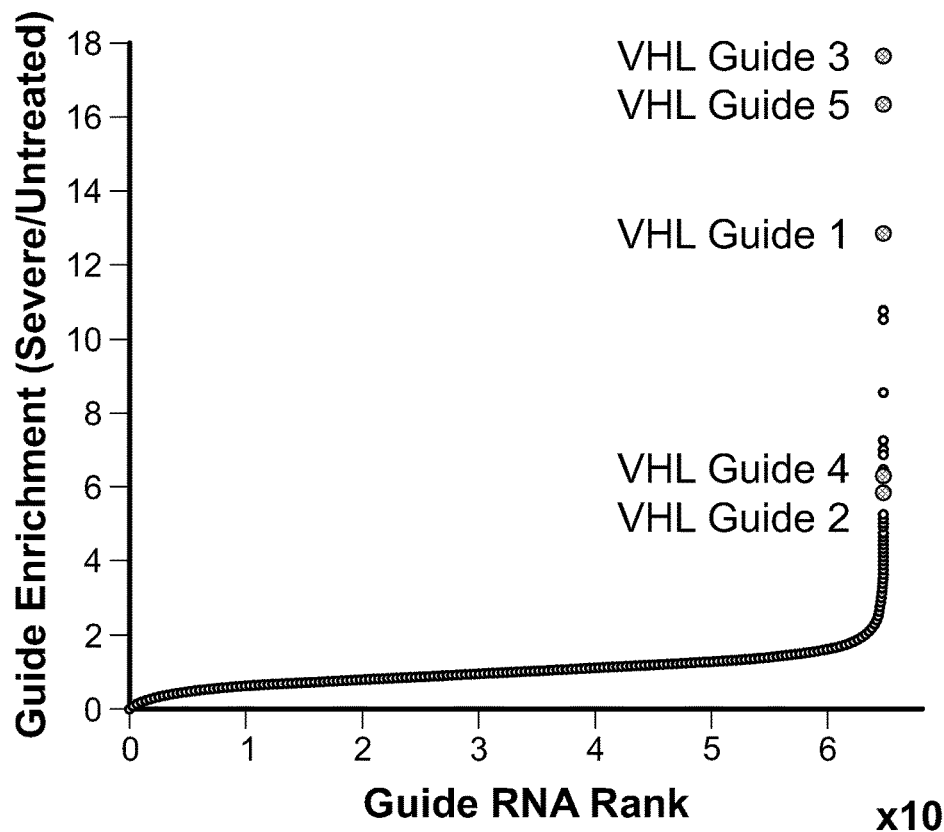
FIG. 6 shows sgRNA enrichment in disease conditions relative to pre-treatment conditions highlighting VHL sgRNAs.
Figure 7:
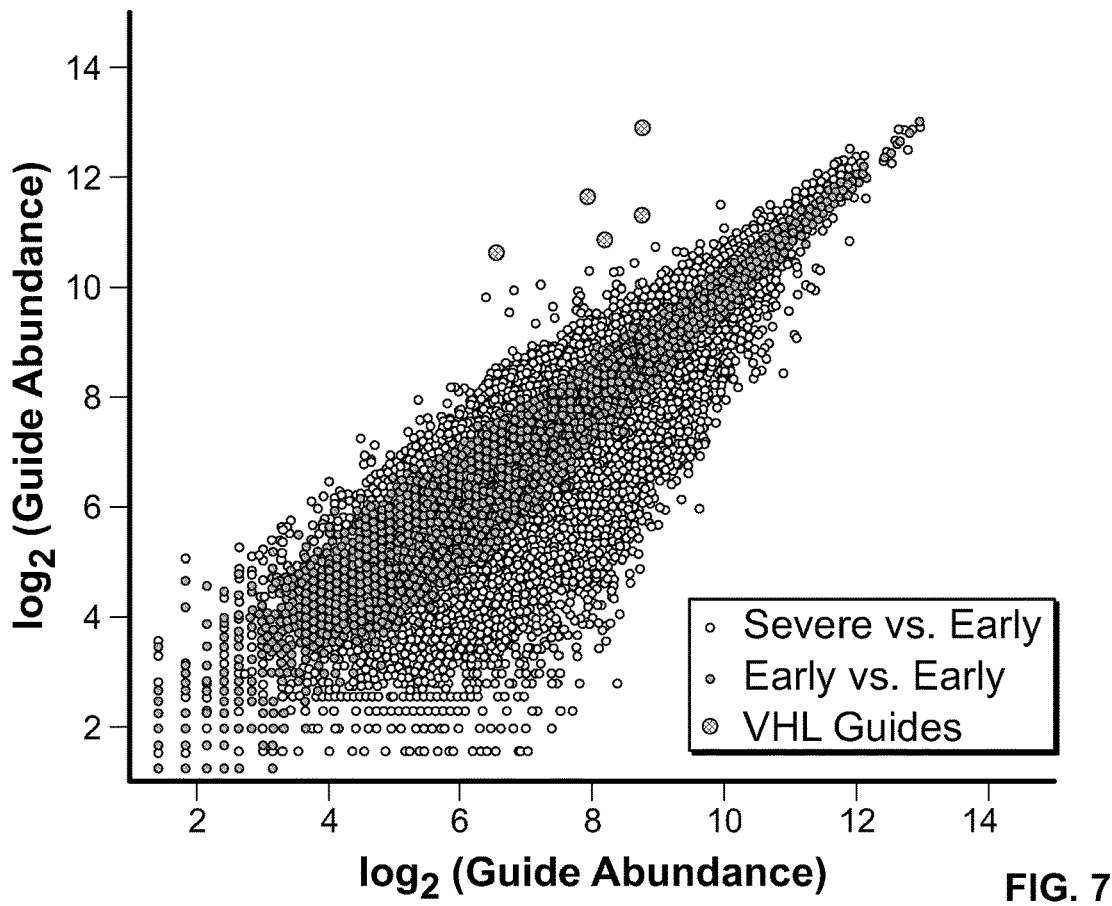
FIG. 7 shows sgRNA enrichment in disease conditions relative to pre-treatment conditions as a log plot.
Figure 8:
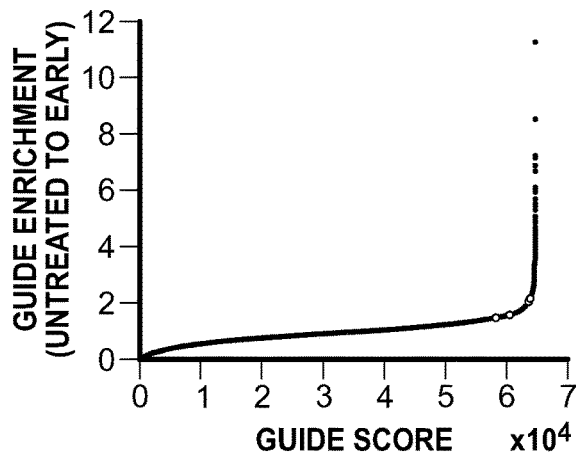
FIG. 8 shows sgRNA enrichment in disease conditions relative to pre-treatment conditions.
Figure 8:
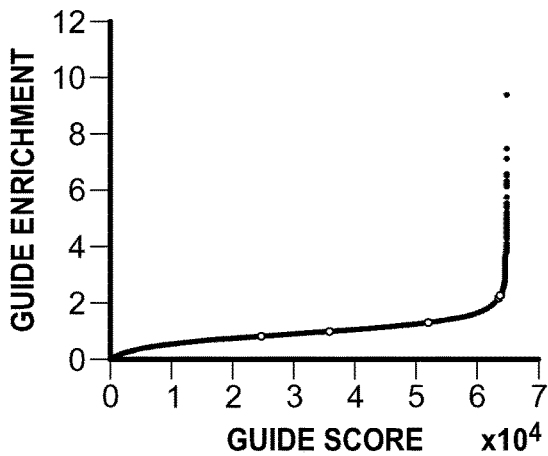
Figure 8:
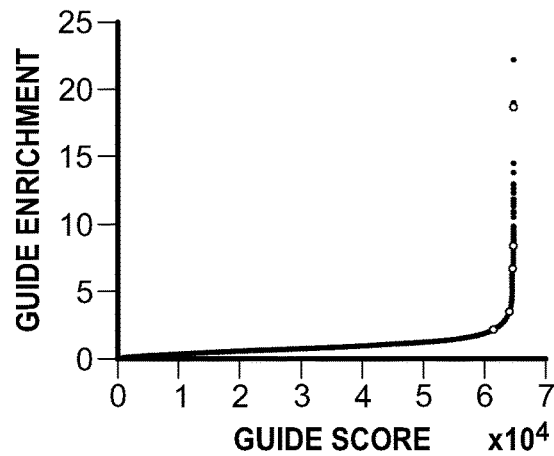
Figure 8:
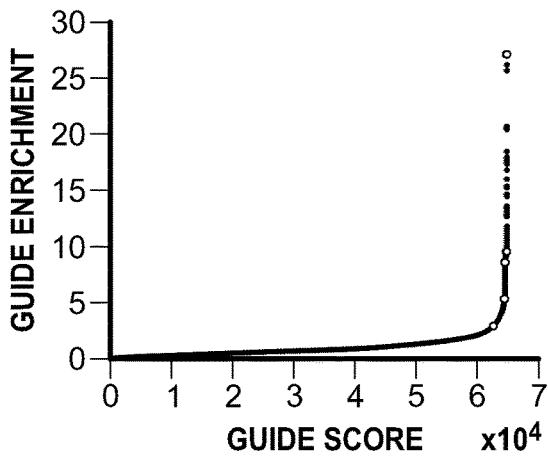
Figure 8:
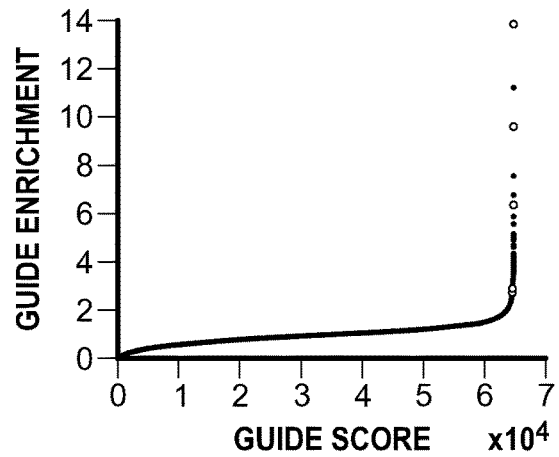
Figure 8:
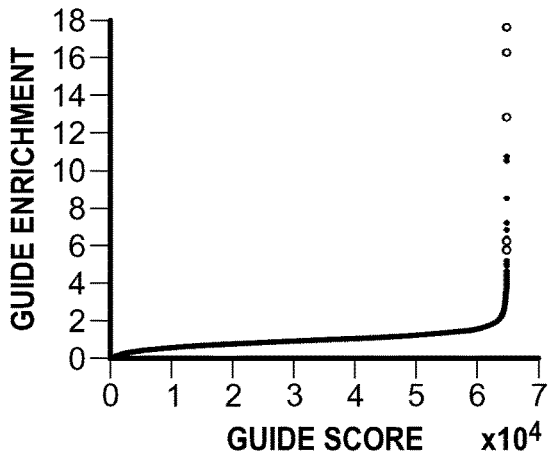
Figure 9:
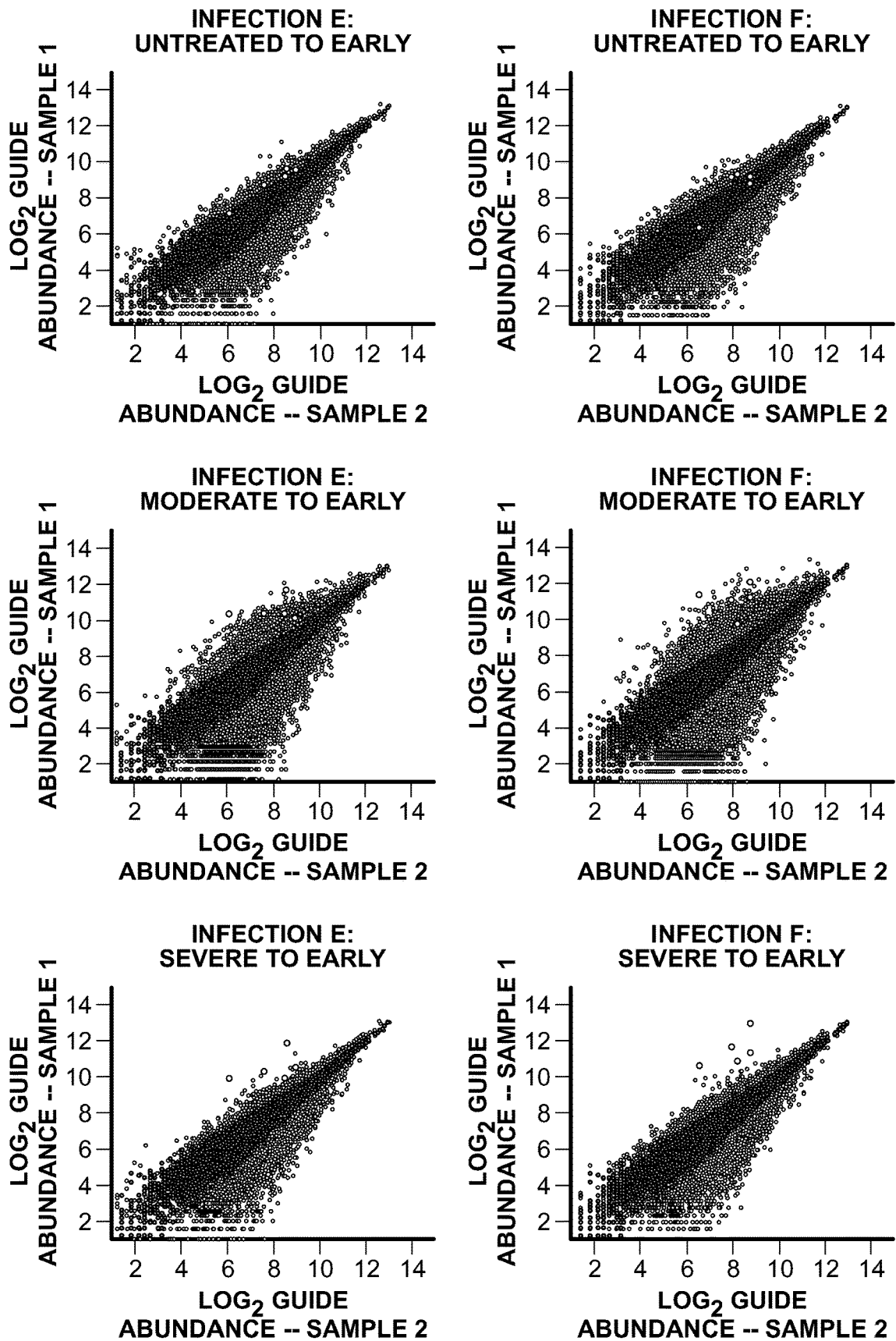
FIG. 9 shows sgRNA enrichment in disease conditions relative to pre-treatment conditions as a log plot.

Mitochondrial disease was modeled in the suspension cell line, K562, and a CRISPR screen was performed to identify potential drug targets. The natural product, Antimycin, was used as a complex III inhibitor of the respiratory chain. In the presence of Antimycin, the respiratory chain is unable to oxidize high energy reducing equivalents to power ATP production. However, redox recycling by the cytoplasmic lactate dehydrogenase reaction, allows other NAD+ dependent reactions to proceed. Removal of pyruvate in the presence of respiratory chain inhibition resulted in reductive stress, further preventing cell proliferation (King, Science, 246:500-03 (1989)). Mitochondrial disease was modeled with the addition of Antimycin alone (moderate disease) or Antimycin in combination with removal of pyruvate (severe disease), using cell growth as a proxy for disease magnitude (FIG. 3). K562 cells were infected with a 65,000 sgRNA library, targeting ~18,000 genes (Shalem et al., Science, 343:84-88 (2014)). After one week of genome editing, the pool of knockout cells were divided into experimental conditions of untreated, moderate disease and severe disease states (FIG. 4). Samples for an enrichment screen were collected by allowing the knockout pool to grow in selection conditions for three weeks. The relative growth between untreated and moderate disease conditions was 100-fold and between untreated and severe disease conditions was 10,000-fold (FIG. 5).

Three weeks of genome editing in untreated cells led to a significant depletion of sgRNAs corresponding to essential genes, including those related to transcription, translation, and splicing. Nearly 20% of the 500 most essential genes were mitochondrial proteins, especially mitochondrial ribosomal proteins and electron transport chain subunits (Table 1). As mitochondrial proteins make up approximately 5% of the proteome, this enrichment highlighted the dramatic effects of mitochondrial dysfunction on viability. Lesions in such essential mitochondrial genes are likely to be disease-causing.

TABLE 1

Examples of essential mitochondrial protein genes

| HGNC symbol | EntrezGene ID | MitoCarta |
|---|---|---|
| ABHD11 | 83451 | 1 |
| ACSM2A | 123876 | 1 |
| AIFM1 | 9131 | 1 |
| ATP5I | 521 | 1 |
| ATP5J2 | 9551 | 1 |
| ATPAF2 | 91647 | 1 |
| BCS1L | 617 | 1 |
| CARS2 | 79587 | 1 |
| CLPP | 8192 | 1 |
| COX15 | 1355 | 1 |
| COX6C | 1345 | 1 |
| CTU1 | 90353 | 1 |
| CYB5B | 80777 | 1 |
| DAP3 | 7818 | 1 |
| DARS2 | 55157 | 1 |
| DNAJA3 | 9093 | 1 |
| DNAJC11 | 55735 | 1 |
| FDXR | 2232 | 1 |
| FH | 2271 | 1 |
| FPGS | 2356 | 1 |
| GADD45GIP1 | 90480 | 1 |
| GFM1 | 85476 | 1 |
| GLRX5 | 51218 | 1 |
| GRPEL1 | 80273 | 1 |
| HSCB | 150274 | 1 |
| HSD17B10 | 3028 | 1 |
| ISCA2 | 122961 | 1 |
| LETM1 | 3954 | 1 |
| LIPT1 | 51601 | 1 |
| LIPT2 | 387787 | 1 |
| LYRM4 | 57128 | 1 |
| METTL17 | 64745 | 1 |
| MRPL12 | 6182 | 1 |
| MRPL13 | 28998 | 1 |
| MRPL16 | 54948 | 1 |
| MRPL17 | 63875 | 1 |
| MRPL20 | 55052 | 1 |
| MRPL28 | 10573 | 1 |
| MRPL47 | 57129 | 1 |
| MRPL49 | 740 | 1 |
| MRPL53 | 116540 | 1 |
| MRPS18A | 55168 | 1 |
| MRPS18B | 28973 | 1 |
| MRPS24 | 64951 | 1 |
| MRPS25 | 64432 | 1 |
| MRPS28 | 28957 | 1 |
| MRPS34 | 65993 | 1 |
| MRPS35 | 60488 | 1 |

TABLE 1-continued

Examples of essential mitochondrial protein genes

| HGNC symbol | EntrezGene ID | MitoCarta |
|---|---|---|
| MRPS7 | 51081 | 1 |
| MTCH2 | 23788 | 1 |
| MTHFD2 | 10797 | 1 |
| MTIF3 | 219402 | 1 |
| NDUFA2 | 4695 | 1 |
| NDUFAF3 | 25915 | 1 |
| NDUFAF5 | 79133 | 1 |
| NDUFB10 | 4716 | 1 |
| NDUFB4 | 4710 | 1 |
| NDUFB9 | 4715 | 1 |
| NDUFS2 | 4720 | 1 |
| NNT | 23530 | 1 |
| NUBPL | 80224 | 1 |
| PARS2 | 25973 | 1 |
| PDSS2 | 57107 | 1 |
| PGS1 | 9489 | 1 |
| PHB | 5245 | 1 |
| PHB2 | 11331 | 1 |
| PNPT1 | 87178 | 1 |
| POLG2 | 11232 | 1 |
| PPA2 | 27068 | 1 |
| RFK | 55312 | 1 |
| ROMO1 | 140823 | 1 |
| RPL35A | 6165 | 1 |
| RPS15A | 6210 | 1 |
| SDHA | 6389 | 1 |
| SDHB | 6390 | 1 |
| SHMT2 | 6472 | 1 |
| SLC16A1 | 6566 | 1 |
| SLC25A26 | 115286 | 1 |
| SOD2 | 6648 | 1 |
| SUPV3L1 | 6832 | 1 |
| TFB2M | 64216 | 1 |
| TIMM44 | 10469 | 1 |
| TIMMDC1 | 51300 | 1 |
| TOMM22 | 56993 | 1 |
| TXN2 | 25828 | 1 |
| VARS2 | 57176 | 1 |
| YARS2 | 51067 | 1 |

Figure 10:
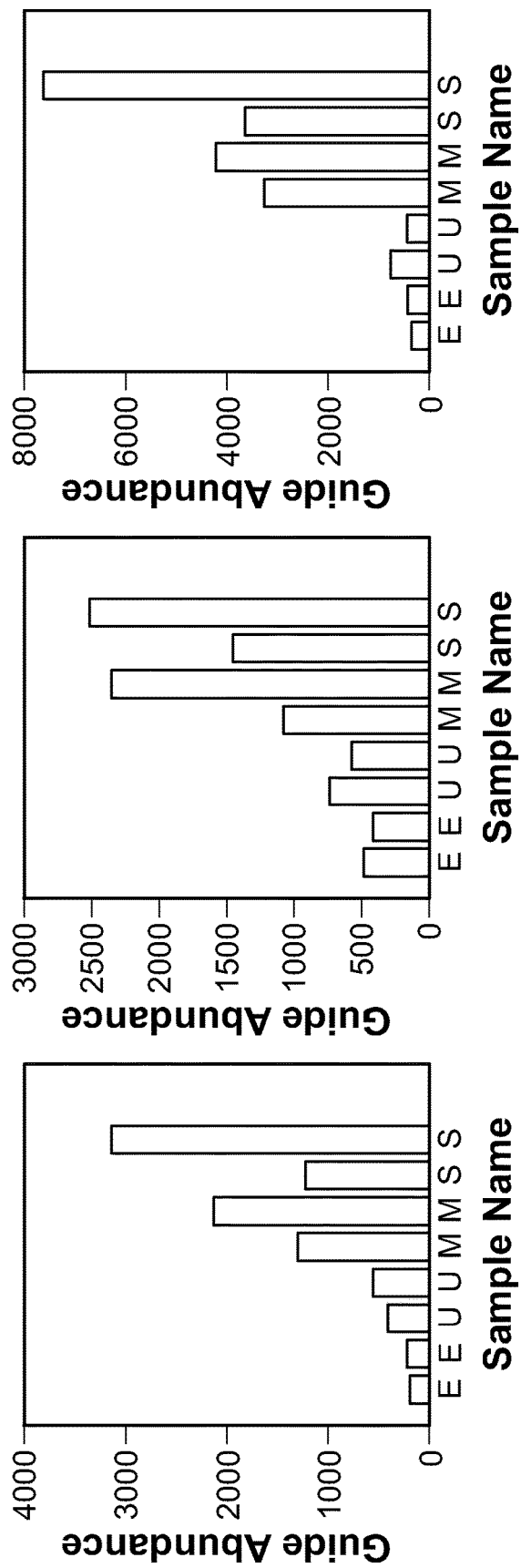
FIG. 10 shows relative cell count with VHL sgRNA comparing untreated (U) to treated conditions (early, E; moderate, M; and severe, S) in K562 cells.
Figure 10:
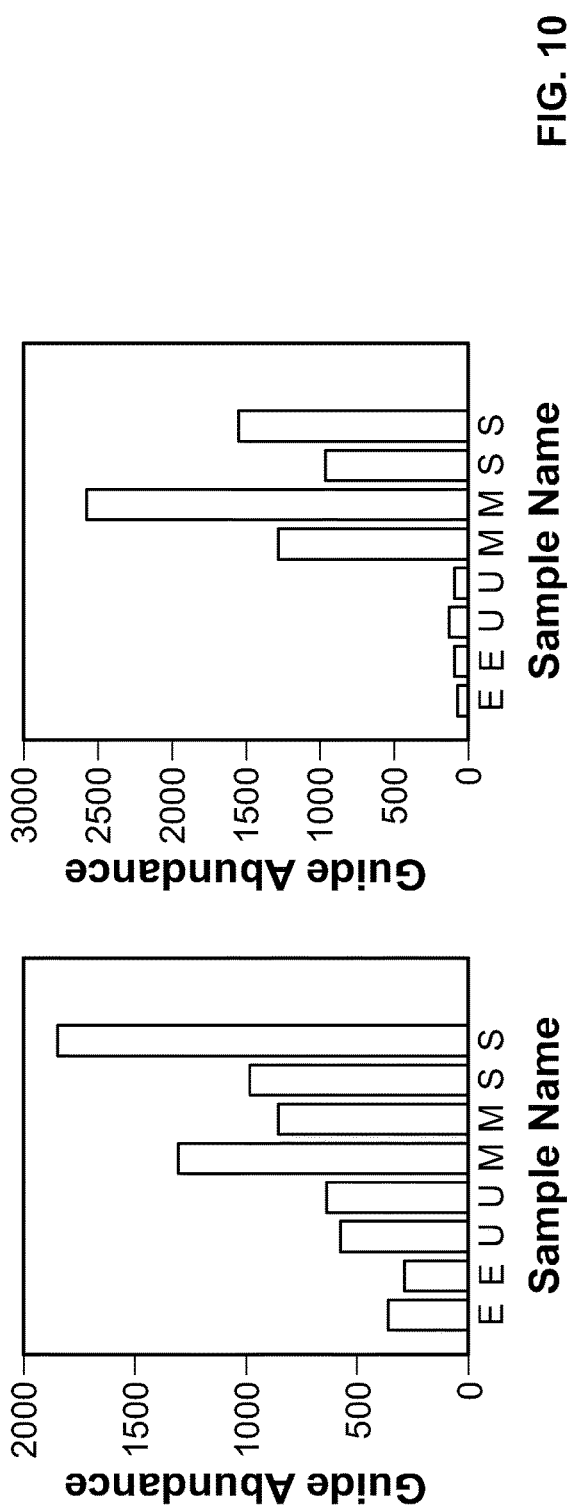

Out of the approximately 18,000 genes tested, the CRISPR screen identified the inhibition of Von Hippel Lindau (VHL) factor as the most effective genetic suppressor for mitochondrial disease, in both the moderate and severe disease conditions. RNAi Gene Enrichment Ranking (RIGER) analysis ranked VHL knockout cells as the most enriched over time in both infection replicates corresponding to severe and moderate disease. For example, the five sgRNAs spanning all three exons of VHL ranked 1, 2, 3, 12 and 14 out of approximately 65,000 total guides for enrichment in disease conditions relative to pre-treatment conditions (Table 2 and FIGS. 6-9). Furthermore, the most significant VHL sgRNAs were enriched greater than 20-fold in disease states (FIG. 10). Even the second-ranked gene target was appreciably less enriched relative to VHL, reflecting the limited therapeutic targets available for mitochondrial respiratory chain dysfunction. Of note, VHL knockout cells were also enriched in untreated conditions over time, reflecting an overall effect on cell growth. However, this enrichment was significantly less than in disease conditions.

TABLE 2

Enrichment of sgRNAs and corresponding genes based on CRISPR in disease conditions relative to pre-treatment conditions.

| Gene | CRISPR Guide Ranks | Rank |
|---|---|---|
| VHL | 1, 2, 3, 12, 14 | 1 |
| RGS20 | 13, 145, 2266, 8296, 27675, 29239 | 2 |
| SIN3A | 32, 242 | 3 |
| ESPNL | 168, 199, 8244, 8519, 12532, 58512 | 4 |
| EXOC3L4 | 47, 267, 6259, 7589 | 5 |
| DOCK7 | 177, 299, 4796, 10550, 18350, 23644 | 6 |
| NDUFS6 | 8, 403, 2876, 7677 | 7 |
| CLSTN1 | 7, 412, 11644, 46491 | 8 |
| CD101 | 139, 372, 14840, 30593, 57365, 61388 | 9 |
| TRIO | 277, 342, 1831, 23700, 37855 | 10 |

VHL activity is a key regulator of the hypoxia response pathway (Ohh et al., Nature Cell Biol. 2:423-27 (2000)). Organisms have evolved elaborate defense mechanisms to cope with changing oxygen tensions and extreme environments. In normoxic conditions, the hypoxia inducible transcription factors (HIF) are constitutively made and hydroxylated by the prolyl-hydroxylase (PHD) enzymes (FIG. 1) (Majmunder et al., Molecular Cell. 40:294-309 (2010)). The hydroxylated form is recognized by the ubiquitin ligase, VHL, and targeted for degradation. During hypoxia, the PHD reaction does not take place, allowing HIF1α stabilization and activation of the hypoxia transcriptional program. VHL-knockout cells show HIF1α stabilization, even during normoxic conditions, thereby bypassing cellular oxygen sensing mechanisms (Ivan et al., Proc. Natl. Acad. Sci. U.S.A. 99:13459-64 (2002)).

Figure 11:
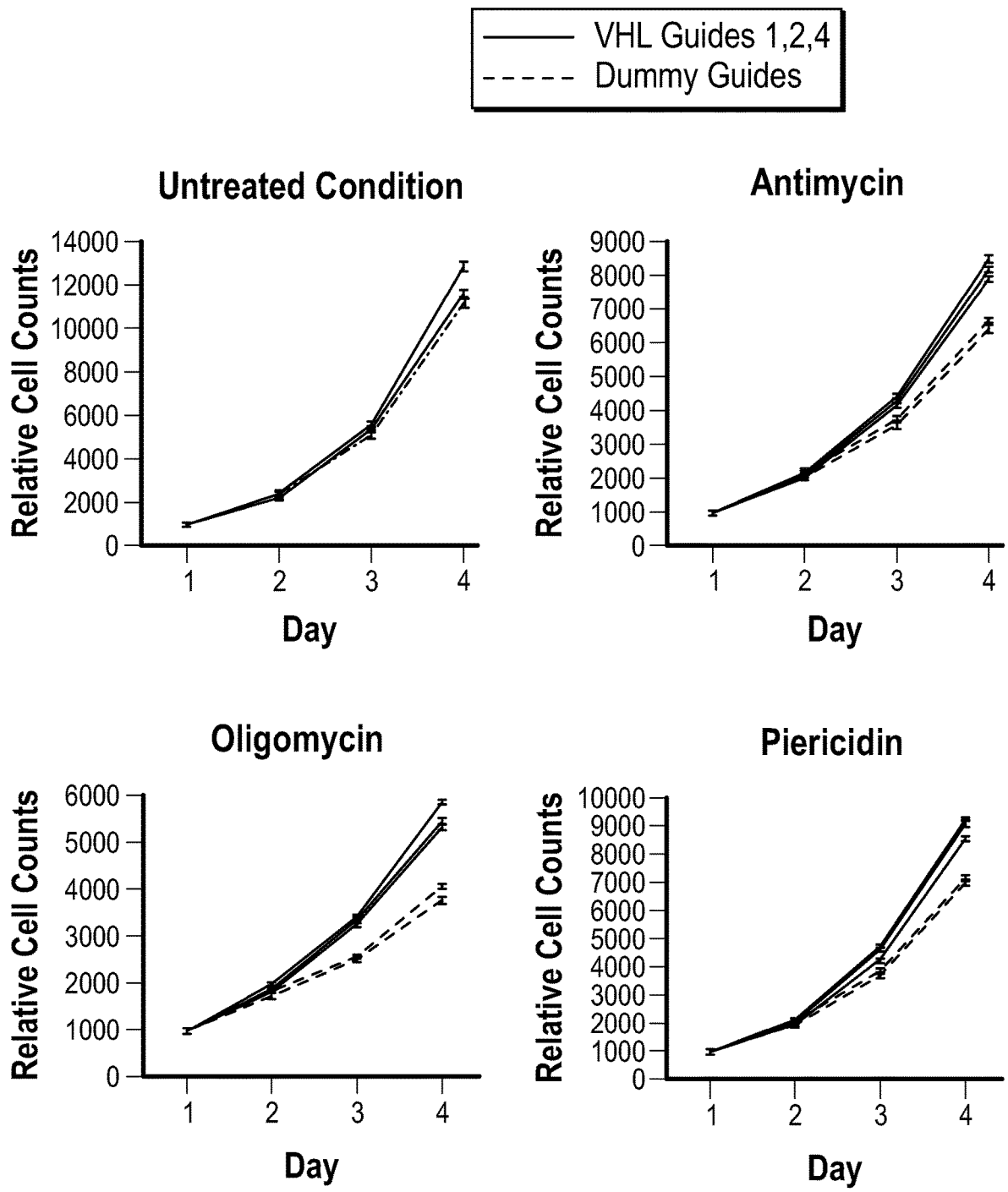
FIG. 11 shows relative cell count with VHL sgRNA comparing untreated to treated conditions in K562 cells.

VHL was validated and characterized as a therapeutic target by testing the ability of VHL-knockout cells to withstand respiratory chain dysfunction. VHL-modified cells showed increased cell proliferation in the presence of Antimycin (moderate and severe disease conditions) relative to non-targeting (dummy) sgRNA-modified cells (FIG. 11). Furthermore, there was a strong positive correlation between the degree of VHL sgRNA enrichment in the CRISPR screen and the rescue effect size of individual sgRNAs, likely reflecting differences in genome editing efficiencies. The therapeutic value in the context of complex III deficiency could be extended to lesions in other mitochondrial complexes. VHL-knockout cells were also more resistant to Complex I inhibition by Piericidin and ATP synthase inhibition by Oligomycin, demonstrating the broad utility of this therapeutic approach. As mitochondrial disease encompasses such a diverse set of genetic lesions impacting the respiratory chain complexes in varying combinations, such a generic therapeutic is especially attractive. A genome-wide CRISPR screen identified the hypoxia response pathway as the strongest suppressor of mitochondrial disease.

Example 2: Genome-Wide CRISPR Screen

Virus Production

The genome-scale CRISPR knockout (GECKO) library v1 was generously provided by the Zhang Lab. Library details have previously been published (Shalem et al., Science, 343:84-88 (2014)). For library lentivirus production, 1.2e7 cells were placed in each of 25, T225 flasks in 50 ml of full DMEM (Life Technologies 11995) media (containing Pen/Strep, 10% FBS). 18 h later, media in each flask was replaced with 13 ml of DMEM (no Pen/Strep, 10% FBS) and 2 h later, media was replaced with 20 ml OptiMEM (Life Technologies 31985-070; no serum, no Pen/Strep). A transfection mastermix was made by combining individually prepared mastermix A (94 ml of OptiMEM, 2.4 ml of Lipofectamine 2000 (Life Technologies)) and mastermix B (94 ml OptiMEM, 2.1 ml of PLUS Reagent (Life Technologies), 240 µg of pVSVg plasmid, 360 µg of psPAX2 plasmid and 480 µg of GECKO plasmid library). Mastermixes A and B were combined at RT for 20 m. 8 ml of the final mastermix was added to each T225 flask of HEK 293 cells. After 6 h, the media was changed to 30 ml of DMEM media (w/1% BSA (Sigma)) and cells were incubated for 48-72 h, before virus-containing supernatant was collected. Virus was concentrated by spinning for 2 h at 24,000 rpm using a SW32Ti rotor. Virus was resuspended overnight at 4 C, allowing pellets to dissolve. Library virus was stored at −80 C prior to use.

Screen

K562 cells were obtained from ATCC and maintained in full DMEM media (10% FBS, Pen/Strep). K562 cells were grown in 1 L spinner flasks (Matrical) on magnetic stir plates (Bellco). Cells were always passaged before reaching confluency (1e6/ml) and subcultured at a concentration of 1e5/ml.

Virus Infection

250e6 K562 cells were resuspended to a concentration of 1.5e6 cells/ml. Polybrene (Sigma) was added to 120 ml of the K562 cell suspension at a final concentration of 4 µg/µl. 2 ml of this cell suspension was placed in each well of 5, 12-well plates. 10 ul of virus was added to each well for a target MOI of 0.3, ensuring that most cells incorporated 1 or 0 lentivirus particles. Plates were spinfected for 2 h at 1000 g and placed in an incubator for 1 h, after which media was aspirated. 2 ml of full DMEM media (10% FBS, Pen/Strep) was placed in each well and cells were resuspended. 12 h later, all wells were pooled into a spinner flask with 800 ml of full DMEM media. A sample was taken for virus titration to ensure that the target MOI was obtained. 24 h after the spinfection, Puromycin (Invitrogen, final concentration of 2 µg/ml) was added to begin selection for infected cells. Two independent infections were performed to control for variability in library infection.

Passaging

Infected cells were passaged before reaching 1e6/ml and maintained in Puromycin-containing conditions for one week after infection. At this point, 70e6 cells were pelleted and stored as pre-treatment (Early) samples for each infection replicate.

Experimental Selection

After 1 week of Puromycin selection, cells from each infection replicate were transferred to experimental conditions of (a) untreated cells, (b) moderate disease and (c) severe disease. 70e6 cells were pelleted and resuspended in media corresponding to each experimental condition. The untreated condition was defined as complete DMEM media, (11965-092) with 1 mM pyruvate (Invitrogen) added. The moderate disease condition was defined as complete DMEM media with 100 nM Antimycin (Sigma) and 1 mM pyruvate. The severe disease condition was defined as 100 nM Antimycin, without pyruvate.

Passaging in Experimental Conditions

Cells were subcultured at 1e5/ml and passaged before reaching 1e6/ml. At each passage, 70e6 cells were pelleted and stored for intermediate screen time points.

Library Prep

Sequencing libraries were prepared as previously described (Shalem et al., Science, 343:84-88 (2014)).

Briefly, DNA was extracted using the Qiagen Blood and Cell Culture DNA Maxi Kit from 70e6 cells per experimental condition, for each infection replicate. DNA was then purified using Micro Bio-Spin columns (BioRad 732-6224). 25 PCR reactions were performed using Herculase II Fusion DNA Polymerase (Agilent) to amplify the sgRNAs from genomic DNA, at a minimum coverage of 450× per sgRNA. 30 ul from the first pooled PCR samples were used as input for the second PCR reaction, allowing for attachment of barcodes and sequencing adapters. Barcode replicates were included for the moderate disease condition to ensure that PCR errors were not substantially contributing to signal. The final PCR products were run on an agarose gel and the correct size PCR products were gel extracted and sequenced on an Illumina HiSeq 2500 platform at the Broad Institute.

Analysis

Processing of sgRNA Reads

Custom Python and Matlab scripts were written for processing of sequencing reads. Reads were trimmed to remove barcodes and sequences corresponding to the GECKO library backbone. A custom bowtie library was created for mapping between sgRNA sequences and guide/gene names. Bowtie alignment was performed, allowing for single mismatches. Finally, guide abundance was compiled for each experimental condition and a matrix mapping guide name to abundance for all samples was created.

Identification of Enriched and Depleted SgRNAs

Cell Viability Screen

In order to identify genes which are essential to cell viability, guide abundance was first normalized to total number of reads per sample. The fold-enrichment was calculated for untreated samples (day 21 after experimental selection) relative to pre-treatment conditions (day 1 before experimental selection), for both infection replicates. As infection replicates were very well correlated ($r^2 > 0.8$), the top 500 most depleted genes (by RIGER analysis; Luo et al., Proc. Natl. Acad. Sci. U.S.A. 105:20380-85 (2008)) were found for each infection replicate. The intersect of the 500 most essential genes across both infection replicates was determined and crossed with the known list of mitochondrial proteins, or MitoCarta to identify essential mitochondrial genes (Pagliarini et al., Cell. 134:112-23 (2008)). RIGER output was generated for each infection replicate (untreated relative to pre-treated conditions) and used for Gene Set Enrichment Analysis (GSEA) (Subramanian et al., Proc. Natl. Acad. Sci. U.S.A. 102:15545-50 (2005)).

Enrichment Screen

In order to identify gene knockouts which allow cells to cope with mitochondrial dysfunction, fold-enrichment was calculated for moderate or severe disease conditions relative to pre-treatment conditions. The most enriched genes were then individually checked for their overall effect on cell viability (untreated relative to pre-treatment conditions). Alternatively, fold enrichment was also calculated for untreated vs. disease conditions. However, this form of analysis confounds genes which are enriched in disease conditions or selectively depleted in untreated conditions. The top hit was found using either approach.

RIGER Analysis

RIGER analysis (Luo et al., 2008) was used to generate a summary statistic by combining information corresponding to all sgRNAs for a given gene. SgRNAs were pre-ranked by fold-enrichment between two conditions. The Kolmogorov-Smirnov method was used with 1000 permutations. Gene scores were not adjusted for the number of sgRNAs corresponding to a given gene.

GSEA Analysis

Output from RIGER analysis was used for gene set enrichment analysis (Subramanian et al., 2005). All curated gene sets were used during analysis in GseaPreranked mode. All other parameters were set to default values.

Example 3: Activating the Hypoxia Response

Figure 12:
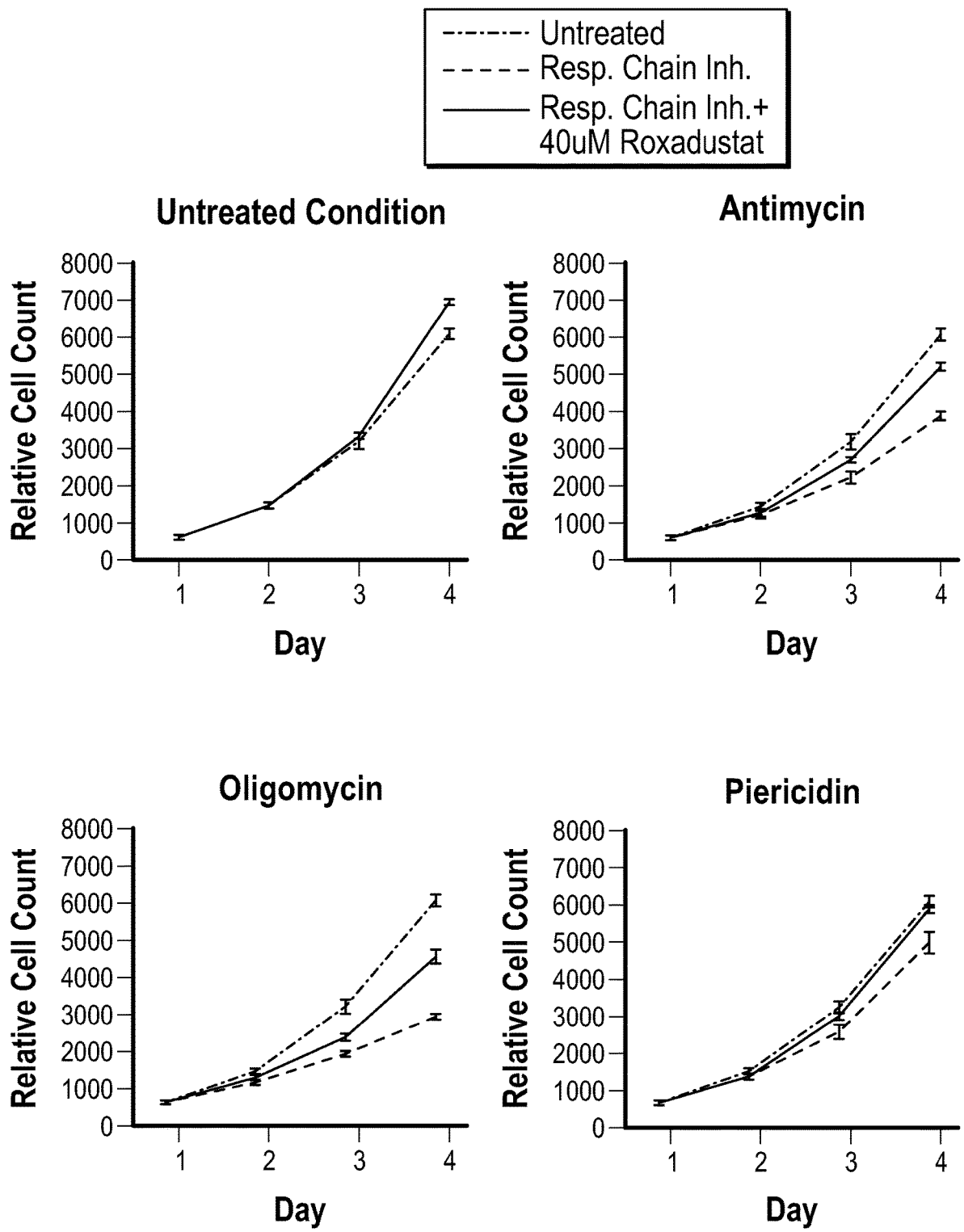
FIG. 12 shows relative cell count with VHL sgRNA comparing untreated to treated conditions in K562 cells.
Figure 13:
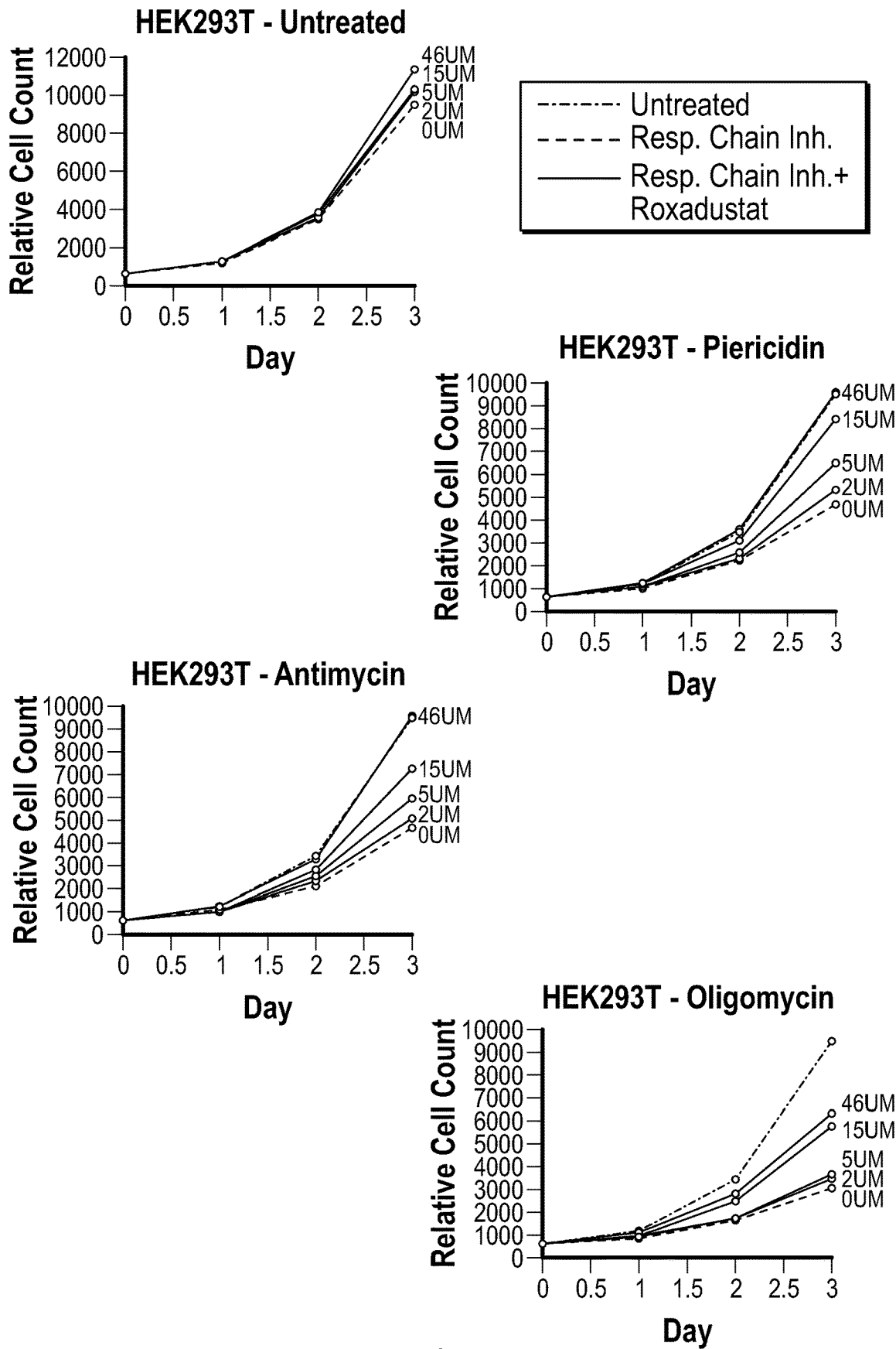
FIG. 13 shows relative cell count with VHL sgRNA comparing untreated to treated conditions in HEK 293 cells.

After VHL was confirmed as an effective therapeutic target for mitochondrial disease, clinically-relevant options for triggering the hypoxia response were studied. While a VHL-inhibitor has been reported (Buckley et al., J. Am. Chem. Soc. 134:4465-68 (2012)), it is not cell permeable. However, PHD inhibitors have been extensively developed for the treatment of anemia of chronic kidney disease and ischemic injury (Rabinowitz, J. Med. Chem. 56:9369-9402 (2013)). The small molecule PHD inhibitor, FG-4592, also known as roxadustat, is currently in Phase III clinical trials for chronic kidney disease. FG-4592 shows efficacy in treatment of kidney disease by upregulating the canonical marker of the hypoxia response, erythropoietin (EPO). FG-4592 treatment may mimic VHL-knockout, thus triggering a broader hypoxia transcriptional program. Compounds that trigger the hypoxia response including VHL-inhibitors and PHD inhibitors are therapeutics for mitochondrial dysfunction. Pre-treatment and incubation with FG-4592 almost completely rescued the growth defects caused by deficiency of multiple respiratory complexes, in multiple cell lines (FIGS. 12-13). Normal growth rates were minimally increased by FG-4592. Complex I, III or V inhibition stunts cell growth in most cell lines, including HT-29s, HEK 293s and K562s. Administering ~50 uM FG-4592 in advance and during respiratory chain dysfunction nearly or completely rescued this growth defect, in a dose-dependent manner (FIG. 12-13). Even ATP synthase inhibition, which additionally affects membrane potential, was significantly rescued by FG-4592. The nearly full rescue of the disease state across different cell lines and across chemical lesions highlights the general utility of this approach.

Figure 14:
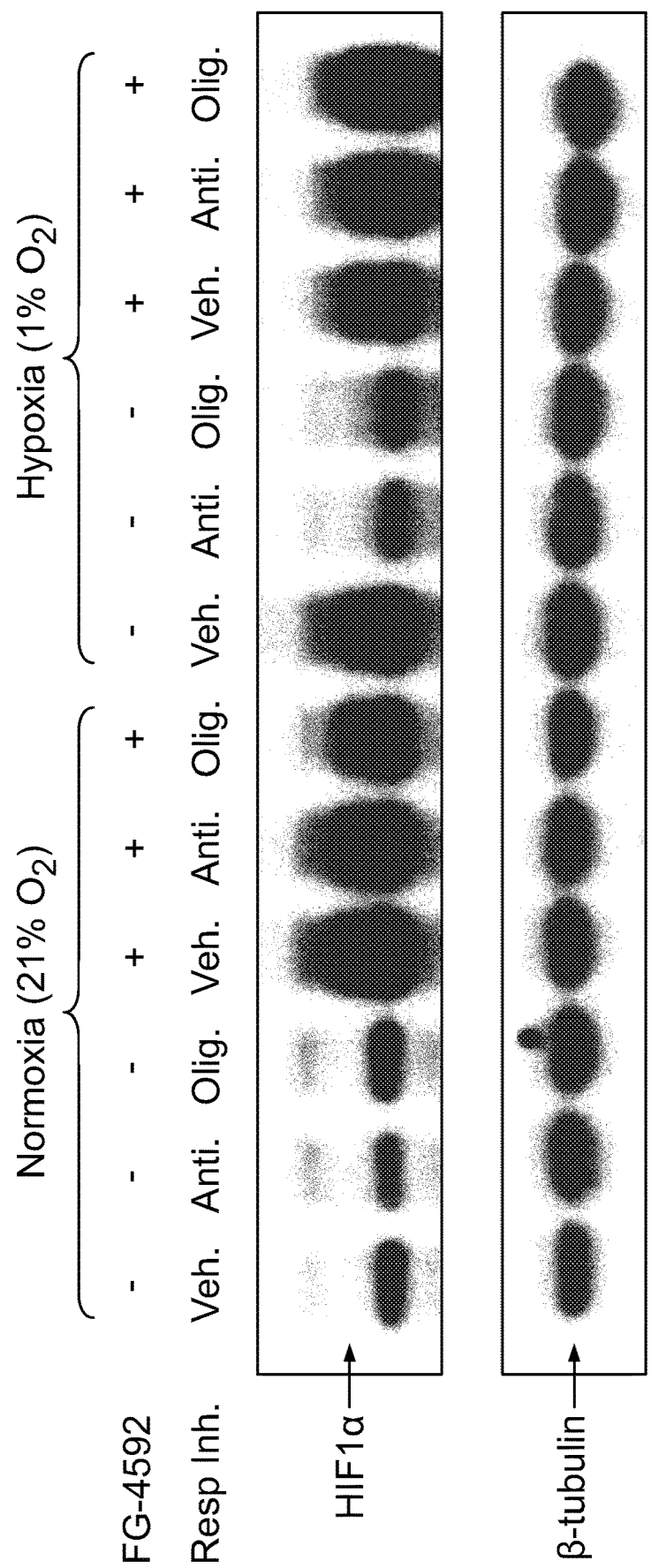
FIG. 14 shows HIF1a stabilization in the face of mitochondrial dysfunction during states of normoxia or hypoxia with FG-4592.

The rescue mechanism of FG-4592 was characterized by studying its effect on the hypoxia response and energy metabolism. While HIF1α is undetectable during normoxic conditions, treatment with FG-4592 stabilized the transcription factor even during normoxia. In hypoxic conditions, FG-4592 stabilized HIF1α beyond the endogenous hypoxia response of untreated cells. It has previously been noted that a paradox exists between mitochondrial dysfunction and cellular sensing of hypoxia (Chandel et al., Proc. Natl. Acad. Sci. U.S.A. 95:11715-20 (1998)). In cell culture, inhibition of the respiratory chain prevents HIF stabilization, even under low oxygen conditions that would otherwise trigger the hypoxia response. Proposed explanations include higher cellular oxygen tensions and increased ROS production during states of mitochondrial dysfunction. While this phenomenon has been noted in the hypoxia field, it has received less attention in the context of mitochondrial disease pathogenesis. If such a paradox extends to mitochondrial disease patients, such individuals may be unable to stabilize HIF in physiological conditions of hypoxia. For example, mitochondrial disease patients may have an aberrant response to ischemia, stroke, high altitudes and tumor growth. This paradox was replicated in cell culture, demonstrating that respiratory chain inhibition by Antimycin or Oligomycin prevented HIF1α stabilization during hypoxia. Of note, FG-4592 treatment bypassed this paradox and enabled HIF1α stabilization in the face of mitochondrial dysfunction, during states of normoxia or hypoxia (FIG. 14). Thus, if this paradox contributes to disease pathology in mitochondrial disease patients, FG-4592 may serve as a therapeutic bypass.

Figure 15:
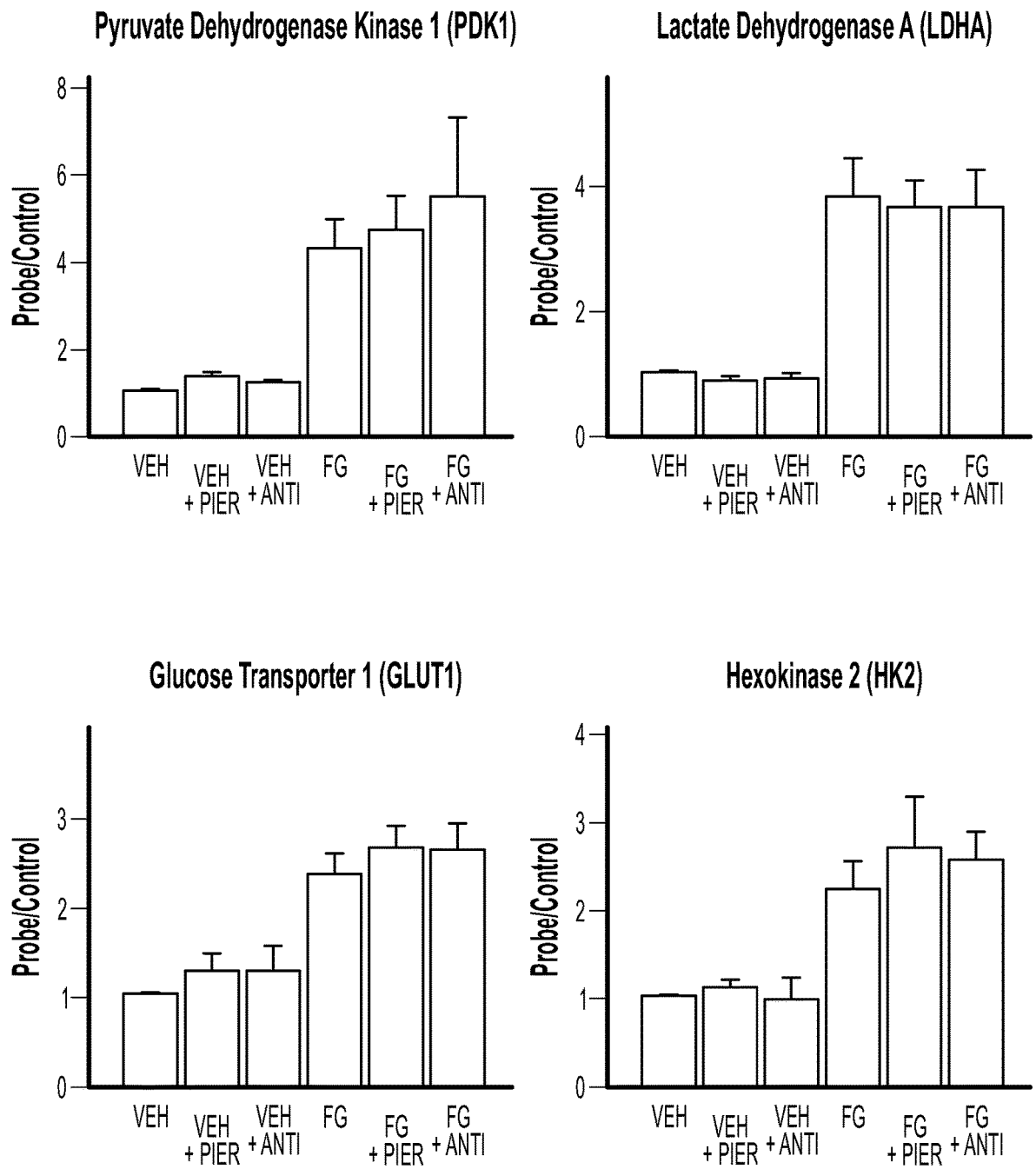
FIG. 15 shows upregulated transcription of exemplary genes involved in energy metabolism with FG-4592.

The HIF transcriptional response is believed to be protective during states of hypoxia, at least in part by causing a rewiring of energy metabolism. By shifting from aerobic respiration to anaerobic glycolysis, the HIF1α response can maintain the energy supply at low oxygen tensions. FG-4592 caused normoxic stabilization of HIF proteins. Treatment with FG-4592 for 24 h, upregulated transcription of genes involved in energy metabolism (FIG. 15). Glycolytic enzymes such as hexokinase 2 (HK2) and glucose transporter 1 (GLUT1) were upregulated in multiple cell types. Glucose import and phosphorylation are rate-limiting steps in the glycolytic flux of many tissues. Lactate dehydrogenase (LDHA) maintains the redox balance during respiratory chain inhibition and was similarly upregulated with FG-4592 treatment. HIF1α activation is also known to shunt the carbon supply away from the TCA cycle and towards the LDH reaction. Several mechanisms have been proposed for this shift away from aerobic respiration, including pyruvate dehydrogenase phosphorylation. In support of this mechanism, a significant upregulation of pyruvate dehydrogenase kinase (PDK1) was observed after FG-4592 treatment. Of note, none of the aforementioned enzymes were upregulated by respiratory chain inhibition alone. Thus, cells were unable to mount the appropriate transcriptional response by endogenous mechanisms. However, FG-4592 treatment triggered the hypoxia transcriptional program, even during respiratory chain inhibition (FIG. 15).

The shift in energy metabolism was confirmed by measuring lactic acid as the end-product of anaerobic glycolysis and oxygen consumption as a proxy for aerobic respiration. In multiple cell types, anaerobic glycolysis was slightly increased by respiratory chain inhibition, likely as a result of allosteric mechanisms. However, treatment with FG-4592 increased glycolysis by nearly 60% in HT-29 cells, under basal conditions and with respiratory chain inhibition. Thus cells are able to shift towards glycolysis using endogenous defense mechanisms; however, a transcriptional response is needed to increase the glycolytic flux enough to maintain cellular growth rates. Furthermore, basal oxygen consumption was decreased with FG-4592 treatment. This may be protective in the setting of mitochondrial dysfunction, as it may limit the amount of ROS produced by impaired electron transport. Genetic and small molecule activation of the HIF pathway enabled cells to cope with mitochondrial dysfunction at multiple steps of the electron transport chain and in multiple cell types. The small molecule, FG-4592, normoxically stabilized HIF and thereby increased glycolysis beyond allosteric mechanisms. Furthermore, it bypassed the paradox between mitochondrial dysfunction and HIF stabilization during hypoxia.

Example 4: Zebrafish Model of Mitochondrial Disease

A zebrafish reporter strain was used to monitor activation of the hypoxia transcriptional response (Santhakumar et al., Cancer Res. 72, 4017-27 (2012)). The reporter fish has a promoter containing hypoxia response elements (HREs) fused to GFP. Hypoxia exposure or VHL knockdown causes an increase in GFP expression, allowing for in vivo monitoring of the hypoxia response. This model system could be used to monitor drug-target engagement and pharmacodynamics of a HIF activator (Chowdhury et al., ACS Chem Biol. 8:1488-96 (2013)). Furthermore, zebrafish embryos have been shown to have a dose-responsive sensitivity to multiple, specific respiratory chain inhibitors including Antimycin (Pinho et al., Br. J. Pharmacol. 169:1072-90 (2013)).

Figure 16:
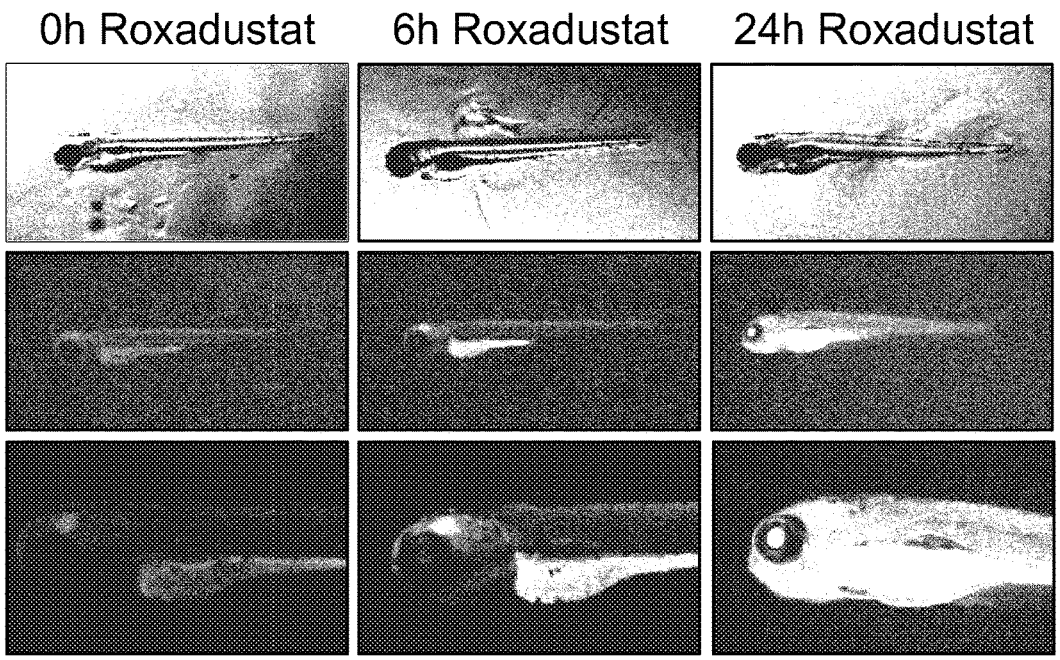
FIG. 16 shows time-dependent increase in activation of the hypoxia response in reporter fish, upon addition of an PHD inhibitor.
Figure 17:
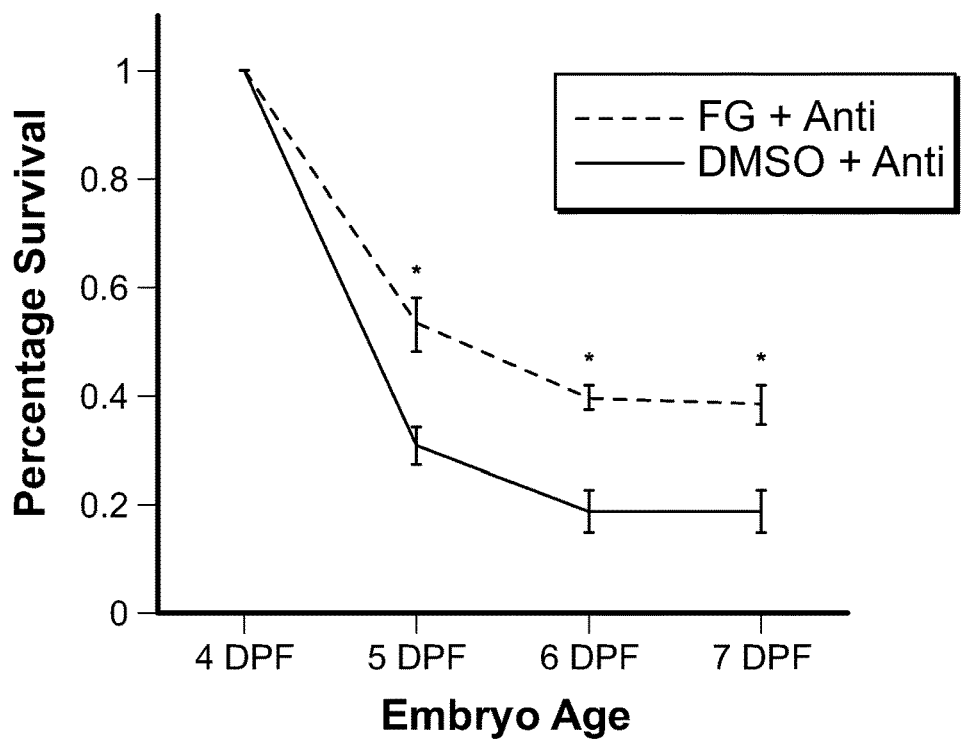
FIG. 17 shows survival of zebrafish with respiratory chain inhibitors in a model of mitochondrial respiratory chain disorder.

FG-4592 treatment resulted in a time-dependent increase in fluorescence of individual reporter fish. After even 6 hours of exposure to 2.5 µM FG-4592, a robust increase in fluorescence was detected (FIG. 16). Thus, FG-4592 engaged the zebrafish prolyl-hydroxylases and triggered the hypoxia transcriptional program. Antimycin inhibits oxygen consumption of zebrafish embryos (Stackley, et al., PLOS One. 6, e25652 (2011)). Prolonged treatment of Antimycin at low nanomolar concentrations resulted in death of embryos. Antimycin-induced death of zebrafish embryos was prevented by treating the fish with FG-4592. At intermediate concentrations of Antimycin, FG-4592 treatment nearly doubled survival (FIG. 17). As both the hypoxia response pathway and mitochondrial functions are particularly well conserved, this is expected to be relevant for higher organisms.

Example 5: Hypoxia as a Therapeutic in a Mouse Model of Leigh Syndrome

The genome-wide screen and cellular and zebrafish models identified the hypoxia response as a suppressor of mitochondrial dysfunction. Extending these findings to an in vivo model, chronic exposure to moderate environmental hypoxia—at 11% $O_2$, a level known to be tolerated in humans—was evaluated to determine whether it could alleviate the disease phenotype in a genetic mouse model of mitochondrial disease.

Leigh syndrome is the most common pediatric form of mitochondrial disease. Though relatively healthy at birth, patients develop irreversible neurodegeneration by two years of age (Lake et al., Journal of Neuropathology & Experimental Neurology. 74(6), 482-492 (2015)). These patients suffer deep, bilaterally symmetric lesions in the gray matter of the brain stem and basal ganglia, with marked gliosis. Most patients die between the ages of 3-16 months. To date, over 60 different genes have been identified that can underlie this devastating syndrome, with Complex I deficiency being the most frequent biochemical cause of disease.

A mouse model of Leigh Syndrome has been generated by disruption of the murine Ndufs4 gene (Kruse et al., Cell metabolism. 7(4), 312-320 (2008)). Loss of NDUFS4 in humans leads to one of the more severe recessive forms of Leigh syndrome. The murine model has been studied at atmospheric (21% $O_2$) levels and faithfully recapitulates much of the reported human disease phenotype. Ndufs4 knockout (KO) mice display retarded growth rates, have impaired visual acuity, and have a delayed startle response. Their body temperature falls progressively until reaching 32° C., shortly before death at 50-60 days of age. Diseased mice also display locomotor deficits and failure to thrive by 50 days. Their neuro-histopathology closely resembles clinical findings, with a substantial inflammatory response in the brainstem and cerebellum. Since this mouse model is well characterized and representative of mitochondrial disease progression, chronic hypoxic exposure was tested as a therapeutic strategy in this model.

Ndufs4 KO mice were first studied to determine whether they were able to tolerate brief hypoxic exposure and mount a hypoxic response in a manner similar to wild type (WT) mice. Three WT mice and three KO mice were exposed to breathing 8.5% oxygen at sea level pressure for 6 hours. This gave the mice sufficient time to mount a transcriptional and translational response. Acute exposure of WT mice to hypoxia triggers HIF stabilization, resulting in Epo transcription and translation. After 6 hours of exposure, Epo protein levels in plasma were measured and showed that both WT and KO mice upregulated Epo production to a similar extent, increasing circulating EPO levels by approximately 40-fold. These results demonstrated that KO mice are able to mount a hypoxia transcriptional response.

Environmental hypoxia of 11% $O_2$ was generated by adjusting the relative concentration of nitrogen and oxygen in the input gas mixture. This created environmental oxygen tensions similar to those found in the high mountain communities of Nepal and Peru (4,500M) (Pawson et al., Proceedings of the Royal Society of London B: Biological Sciences 194(1114), 83-98 (1976)). A control ambient environment breathing 21% $O_2$ was created with an identical chamber set-up.

Mice were placed in 60 liter plexiglass chambers that were given a gas mixture of compressed air and 100% $N_2$, compressed air alone, or compressed air and 100% $O_2$ (Airgas Inc.). The gas flow rates were measured and controlled with rotameters and valves. Oxygen concentrations were measured several times each day at the outlet of the chambers using an oxygen analyzer (MiniOx I Oxygen Analyzer, Ohio Medical Corporation) and the flow rates of air, nitrogen and oxygen were modified if necessary in order to obtain a stable oxygen concentration of 11% in the hypoxic chamber (and 55% in the mild-hyperoxia chamber). Soda lime (Sodasorb, Smiths Medical) (approximately 250 g), was placed on the floor of each chamber to scavenge carbon dioxide ($CO_2$) produced by the animals and replaced every 3 days. The $CO_2$ concentration in each chamber as well as the temperature and the humidity were monitored continuously using a dedicated infrared $CO_2$ analyzer, thermometer and humidity meter (Extech CO200 Monitor, Extech Instruments). The total flow of fresh gas flushing each chamber was adjusted between 5 and 10 L/min to maintain the chamber $CO_2$ level below 0.4% and the relative humidity between 30% and 70%. Mice were exposed to gas treatment continuously for 24 hours per day, 7 days a week.

Ndufs4 KO and control mice were continuously exposed to normoxia or hypoxia (11% $O_2$) after enrollment in the experiment, excluding temporary removal for behavior tests and maintenance three times per week. Untreated Ndufs4 KO mice typically begin to show significant disease progression after approximately 30 days of post-birth air exposure, which is about ten days after weaning. Since hypoxia-related vascular responses (constriction of pulmonary circulation, dilation of ductus arteriosus) occur in early post-natal development, chronic hypoxic exposure treatments were initiated when mice were 30 days old.

Chronic normobaric hypoxia rescued this model of mitochondrial disease. All normoxia-exposed Ndufs4 KO mice either fulfilled criteria for humane euthanasia or died at a median age of approximately 60 days with none surviving past 75 days (FIG. 18A). However, there were no deaths in Ndufs4 KO mice exposed chronically to breathing 11% $O_2$ (FIG. 18A). Several mice showed a mild clasping phenotype at ages greater than 120 days.

The hypoxia-treated mice showed a striking rescue in all aspects of health that were tested, including body weight gain, core temperature maintenance, and neurologic behavior. All Ndufs4 KO mice continued to gain weight between 30-37 days of age (FIGS. 18B-C). At this stage, untreated KO mice lost weight, became hypothermic, and died. In contrast, Ndufs4 KO mice breathing 11% $O_2$ gained weight for several weeks, at which point body weight gain slowed, similar to the growth kinetics of WT mice. The growth rate of hypoxia-treated Ndufs4 KO mice matched that of hypoxia-treated WT mice, suggesting that the primary cause of weight loss in Ndufs4 KO mice was alleviated by hypoxic exposure. At 30 days of age, untreated Ndufs4 KO mice have similar core body temperatures to WT mice. By 50 days, there is nearly a 4° C. drop in temperature in the Ndufs4 KO mice (FIG. 18D). However, Ndufs4 KO mice treated with chronic 11% $O_2$ breathing showed no reduction of core body temperature (FIG. 18D). Thus, chronic hypoxic breathing rescues the underlying metabolic phenotype that directly or indirectly results in alterations of energy and nutrient metabolism.

Ndufs4 KO mice, as well as patients suffering from Leigh syndrome, exhibit striking defects in locomotor activity. Ataxia and failure to thrive are hallmarks of mitochondria dysfunction. Behavioral tests were performed in 10 day intervals in normoxia and hypoxia-treated, WT and KO mice. The rotarod test (Caston et al., Neurobiology of learning and memory, 64:195-202 (1995)) measures the ability of mice to maintain grip strength, balance, and fatigue resistance on an accelerating, rotating rod. A rotarod machine (Ugo Basile) was used to measure the ability of mice to stay on an accelerating, rotating rod. Rotarod parameters were as follows: acceleration of 5 rpm/m and a maximum speed of 40 rpm. On each measurement day, three trials were performed, with individual trials at least 10 minutes apart to allow mice to recuperate. The median time on rotarod is reported. If mice used their body to grasp the rod (rather than walking on it) for more than 10 seconds, this time was recorded as time of fall. Age of measurements is +/−5 days for practical purposes without any age bias between groups.

At 30 days of age, KO mice breathing air display a slight depression in the median time they can stay on a rotarod (FIG. 18E). This ability declines by 40 days and at 50 days, untreated KO mice are no longer able to stay on the rod for more than a few seconds, due to a combination of muscular weakness, inability to balance, and loss of visual activity. Hypoxia-treated WT mice performed similarly to normoxia-treated control mice. Remarkably, KO mice breathing 11% $O_2$ displayed a near complete rescue of this locomotor phenotype.

As a further neurological-behavioral test, spontaneous locomotor activity was measured as total distance traveled within an hour. The open field instrument (Med Associates Inc.) was used to measure spontaneous locomotor activity. Mice were blindly chosen for a given day and placed in open field chambers for 1 hour. Spontaneous locomotor activity was measured based on beam breaks and recorded by the instrument. The traces shown in FIG. 18F are representative of a sick, Ndufs4 KO mouse exposed to 21% $O_2$ (age of such sickness varies slightly between mice), age-matched KO and WT mice exposed to 11% $O_2$, and WT mice exposed to 21% $O_2$. Age of measurements is +/−5 days for practical purposes without any age bias between groups. Untreated KO mice show drastically reduced spontaneous locomotor activity (FIG. 18F). This defect was significantly rescued in hypoxia-treated mice, however only to 50% of the values of control mice (FIGS. 18F and 20).

Example 6: Modest Hyperoxic Exposure is Lethal for a Murine Model of Leigh Syndrome The striking therapeutic effect of hypoxia suggested that oxygen itself may be a key molecular parameter determining Leigh disease progression. Thus, the converse environmental scenario of chronic mild hyperoxic exposure was evaluated. WT and Ndufs4 KO mice were exposed to breathing 55% normobaric oxygen starting at 30 days of age. No effect on survival was observed in WT mice exposed to 55% oxygen. However, all nine Ndufs4 KO mice died of severe acute pulmonary edema after 2 to 11 days of breathing 55% $O_2$ (FIG. 18A). On the other hand, Ndufs4 KO mice breathing air die at approximately 3 weeks after starting treatments. The dramatic reduction of survival in 55% $O_2$ breathing KO mice, along with the dramatic extension of their apparently healthy survival in 11% $O_2$ breathing KO mice, points to the role of arterial oxygen tension in determining the progression of mitochondrial disease.

Example 7: Clinical Chemistry and Histopathology Following Treatment with Hypoxia Ndufs4 KO mice were further characterized following treatment with chronic hypoxia. Complex 1 Activity was measured in cerebellum tissue from mice. Tissue was homogenized in 1 ml of ice-cold PBS using a Qiagen TissueLyser II. Approximately 50-100 mg of tissue was used as input material for the Complex I Enzyme Activity Microplate Assay Kit (ab109721, Abcam). Absorbance was read at 450 nm wavelength and recorded every 30 seconds for 135 total measurements. Background signal was not subtracted in data shown.

Figures 1, 19:
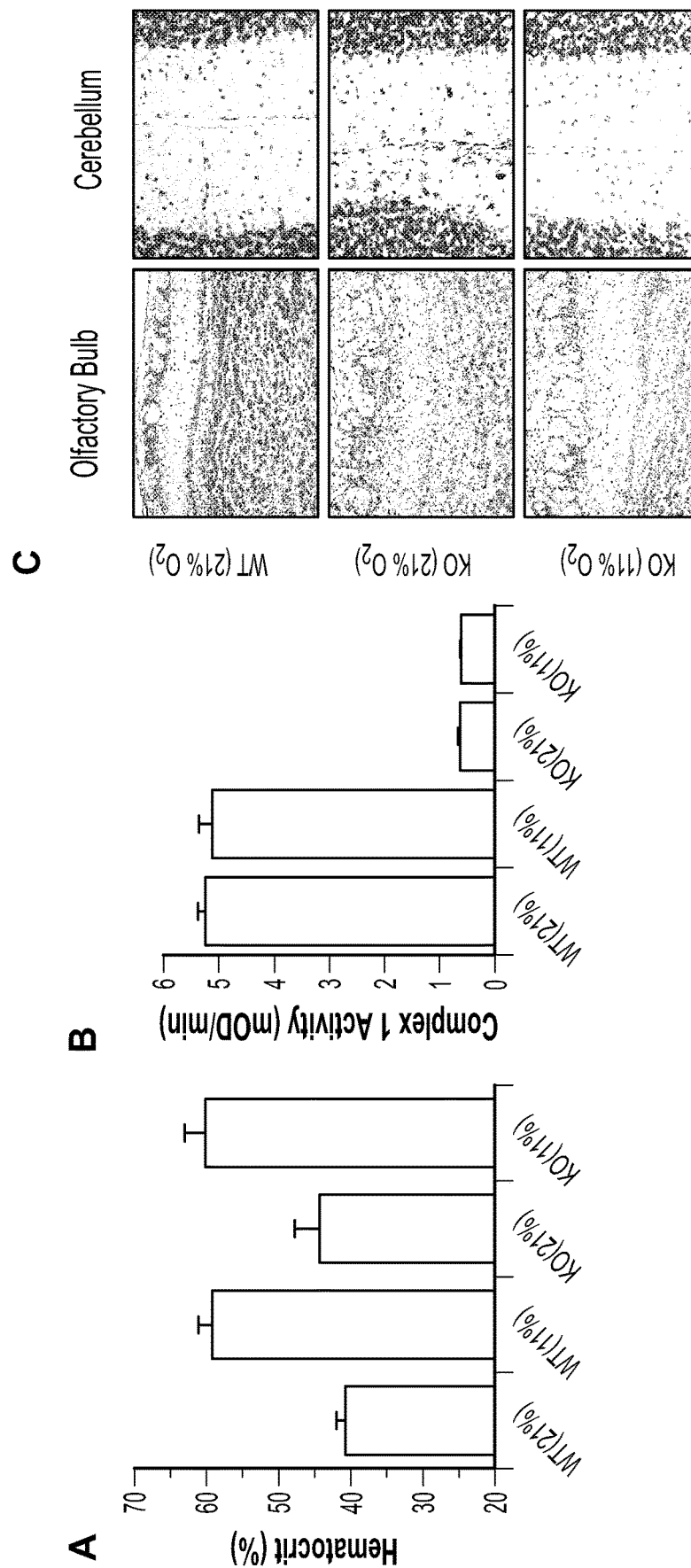

The circulating blood hematocrit in the KO mice was elevated from 40% during normoxia to approximately 60% during hypoxia, indicating EPO target engagement by hypoxic breathing (FIG. 19-1A). Furthermore, although Ndufs4 KO mice appear quite healthy following hypoxia treatment, brain Complex I activity remained dramatically reduced to the same levels as untreated Ndufs4 KO mice (FIG. 19-1B).

Normoxia-treated KO mice exhibit substantial neuronal degeneration. Lesions are accompanied by Iba-1+ microglial proliferation within olfactory lobes, cerebellum and brainstem as documented elsewhere (Quintana et al., Proc. Natl. Acad. Sci. U.S.A. 107, 10996-11001 (2010)). Mice were anesthetized and the chest cavity was opened and a catheter was placed in the left ventricle. The whole body was perfused with ice cold PBS and then with 4% PFA. The brain was dissected out, stored overnight in 4% PFA and then placed in 30% sucrose (in PBS) for two days. Formalin-perfused brains were sectioned parasagittally at the olfactory lobes. Two transverse sections of cerebellum and brainstem were also collected: a rostral section with subjacent pons, and a more caudal section with medulla oblongata. Immunohistochemistry was performed on adjacent tissue sections using an antibody recognizing the microglial marker Iba-1 (Wako; 2 µg/ml). In contrast to normoxia-treated KO mice, KO mice breathing 11% $O_2$ exhibited minimal to no lesions (FIG. 19-1C), and were virtually indistinguishable histologically from WT controls.

α-hydroxybutyrate has been identified as a circulating plasma marker of Leigh syndrome (Legault et al., Cell reports. 13, 981:89 (2015)). Lactate and α-hydroxybutyrate were quantified in mouse plasma by spiking in each corresponding isotope labeled standard (CDN isotope). A series of standard solutions of metabolites at seven different concentrations were prepared in a surrogate matrix buffer (PBS buffer with 30 g/L human serum albumin). 30 uL of the mouse plasma sample were combined with 20 uL of isotope labeled internal standard, vortexed for 10 seconds and spun down for 10 seconds. Metabolite extractions were performed using 70% acetonitrile. A Q Exactive Plus Orbitrap Mass Spectrometer coupled to a Dionex UltiMate 3000 UHPLC system (Thermo Fisher Scientific) was used for LC-MS. The Xbridge amide HILIC column (2.1×100 mm, 2.5 µM particle size, from Waters 186006091) was used to separate metabolites and MS was acquired under the negative ionization mode. The column was maintained at 27° C. during runs. The mobile phase A was 20 mM ammonium acetate, 0.25% ammonium hydroxide pH adjusted to 9. The mobile phase B was 100% acetonitrile. The MS data acquisition was full scan mode in a range of 70-1000 m/z, with the resolution set at 140,000, the AGC target at 3E6, and the maximum injection time at 400 msec.

α-hydroxybutyrate was elevated in air-breathing Ndufs4 KO mouse plasma (FIG. 19-2D). Treatment with chronic hypoxia rescued the elevation of this disease marker (FIG. 19-2D). Similarly, plasma lactate levels were increased in Ndufs4 KO mice breathing air between 50-65 days of age, while this was partially rescued by 11% hypoxic exposure (FIG. 19-2E). Collectively, these laboratory and histopathological studies confirm that chronic hypoxic exposure to breathing 11% $O_2$ activates the endogenous hypoxia response. Hypoxia does not fix the proximal lesion within mitochondrial Complex I, but rather, prevents the onset of subsequent biochemical and histopathological defects.

Example 8: Effects of Treatment with Hypoxia on Disease Pathology

To assess whether hypoxic therapy can reverse established neurodegenerative disease, we compared the effects of hypoxia on early-stage disease and late-stage disease. Ndufs4 mice were chronically exposed to hypoxia treatment starting at 30 days of age, termed early-stage treatment. Alternatively, Ndufs4 mice were chronically exposed to hypoxia beginning at 55 days of age, termed late-stage treatment. Early-stage treatment began prior to the development of any disease symptoms, allowing for the prevention of disease. Late-stage treatment began after the disease had already manifested, thus testing for the reversal of disease.

Figure 21:
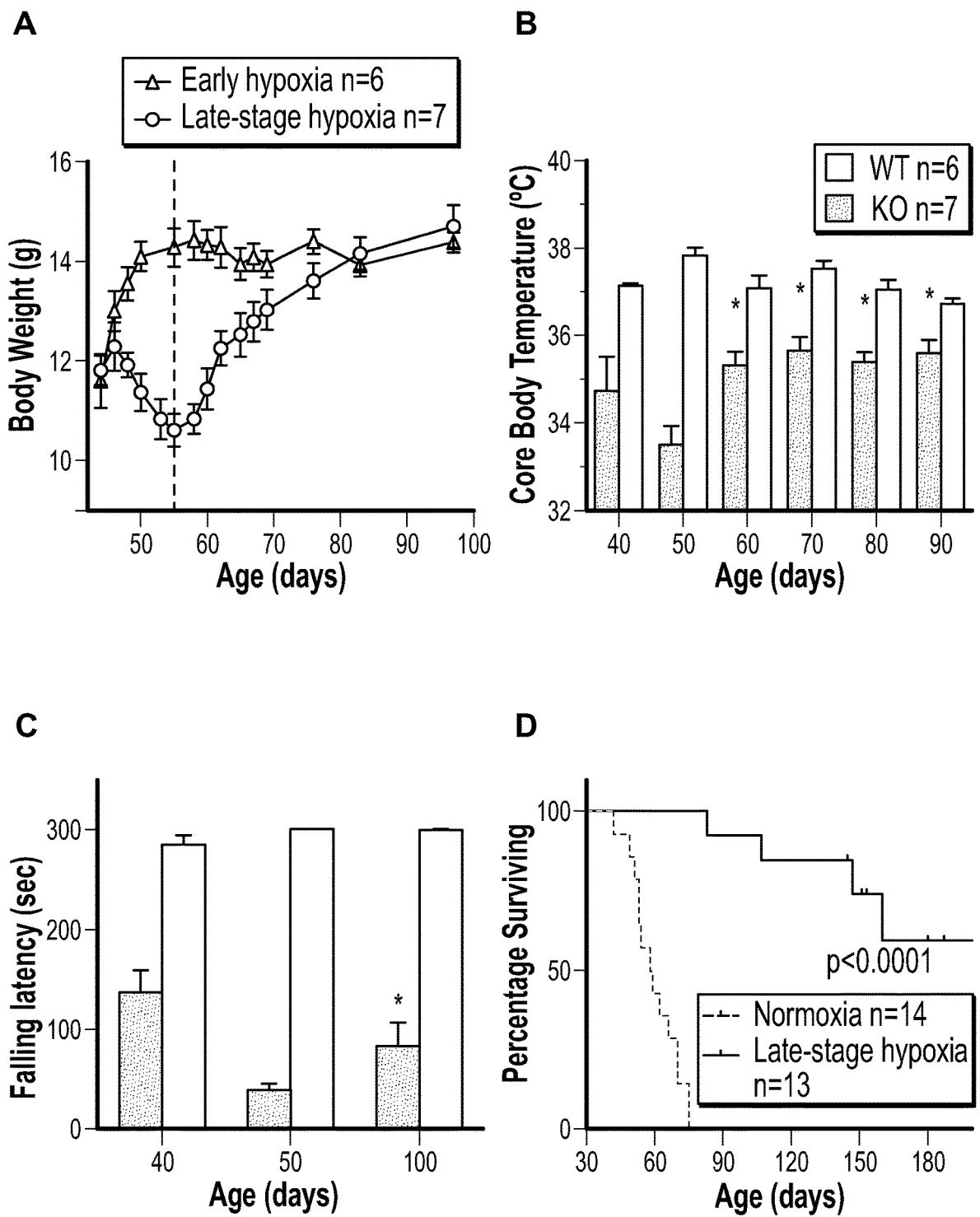
FIGS. 21A-D show that hypoxic breathing (11% $O_2$) rescues mice with severe neurological disease, and enables long term survival, augments body weight and enhances the behavior of Ndufs4 KO mice who have developed late-stage neurologic impairment. (A) Growth curves of Ndufs4 KO female mice exposed to therapeutic hypoxic breathing, starting at 30 days of age (triangles) and late-stage hypoxic breathing, starting at 55 days of age (circles). (B) Body temperature and (C) latency of falling from an accelerating rod in Ndufs4 KO mice with late-stage disease and WT controls exposed to breathing 11% $O_2$ starting at 55 days of age. (D) Survival rates of mice in normoxia (unbroken lines) or hypoxia beginning late-stage disease (dashed lines). Data shown as mean±SE.

By 55 days of age, the early-stage hypoxia treatment group weighed 14.2 g, due to the ameliorative effects of hypoxia. In contrast, normoxic mice of this age weighed 10.6 g. Chronically exposing these mice to late-stage hypoxia resulted in an improvement of body weight and body temperature trajectory. After one month of hypoxic therapy, the body weights of early-stage treatment and late-stage treatment groups were indistinguishable (FIG. 21A). Core body temperature in normoxic mice was 33.5° C. at 55 days of age. Late-stage hypoxic treatment resulted in an increase of core temperature from 33.5° C. to 35.3° C. within five days of hypoxia exposure (p<0.05) (FIG. 21B).

Behavior was additionally improved as measured by the ability to stay on an accelerating, rotating rod. By 50 days of age, normoxic KO mice can only stay on a rotating rod for 35 seconds. Exposing these mice to 50 days of late-stage hypoxia treatment partially rescued their ability to stay on the rod from 35 seconds to 82 seconds (FIG. 21C). Furthermore, late-stage hypoxia significantly improved the survival rate of KO mice (FIG. 21D). The median survival age of the rescued cohort was 200+ days versus 58 days of normoxic controls (HR 9.4 (8.2-65.6) 95CI, p<0.001).

Figure 22:
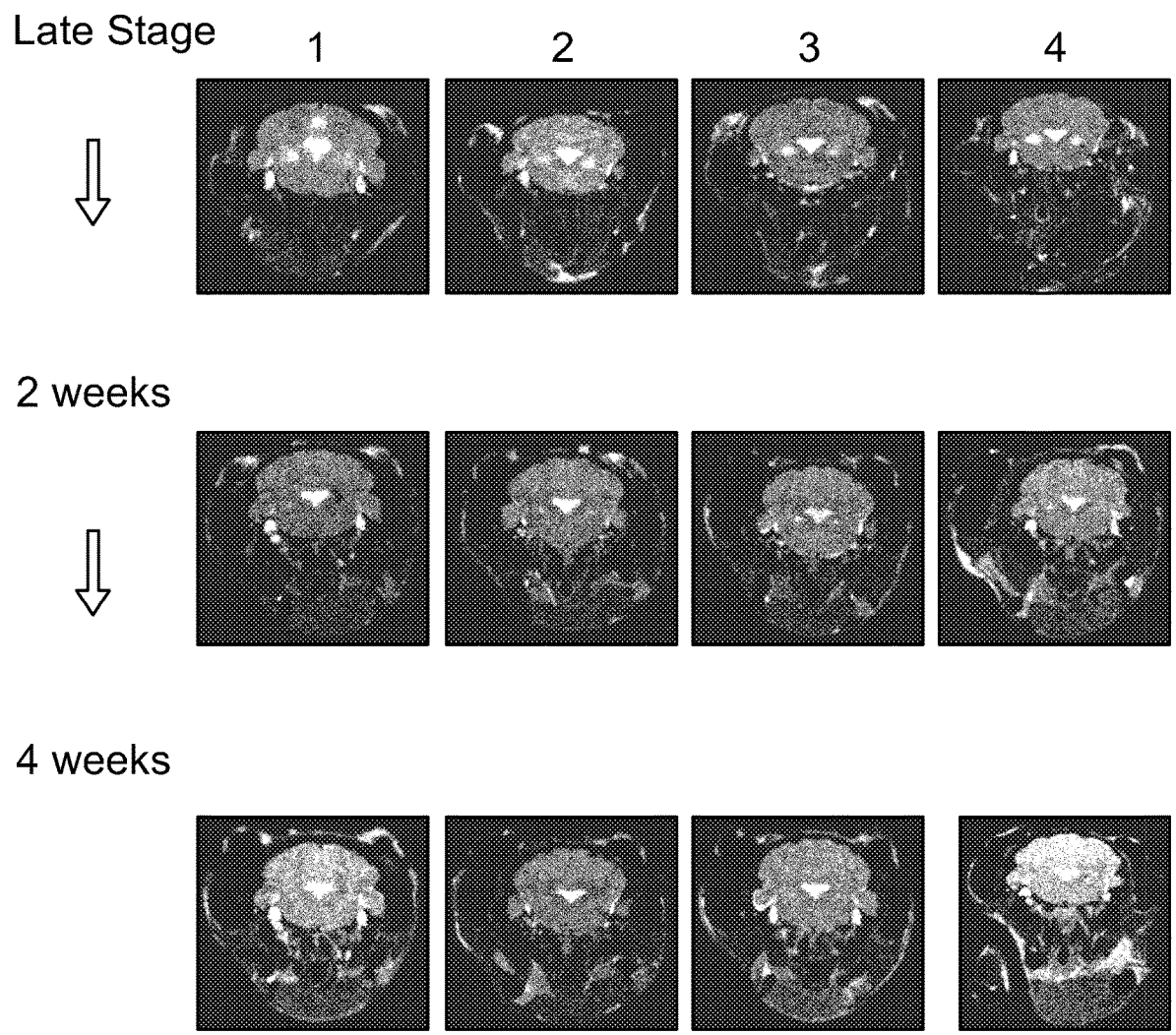
FIG. 22 displays a series of photographs showing that breathing 11% $O_2$ reverses the established neurological lesions of Ndufs4 KO mice who were breathing air. Four Ndufs4 KO mice breathed normoxic air (21% $O_2$) until they developed late-stage debilitating neurological disease (55 days). MRI scans were performed and detected hyperintense lesions, apparent in the vestibular nuclei (top row, white arrows). Subsequently, mice breathed 11% oxygen and were scanned again at two and four weeks after hypoxic treatment (middle and bottom rows respectively). Neurological lesions on MRI had disappeared by four weeks of hypoxic breathing.

Leigh syndrome patients develop symmetric, bilateral lesions in the brain. The same mode of pathogenesis has previously been demonstrated in normoxic Ndufs4 KO mice. To determine whether the survival and behavior rescue effected by late-stage hypoxia treatment are accompanied by a reversal of the cerebral lesions, sequential brain MM scans were performed in four Ndufs4 KO mice receiving late-stage hypoxia therapy. After the first scan, mice were treated with hypoxia for two weeks and a second scan was performed (FIG. 22). After four weeks of 11% $O_2$ breathing, a third scan was performed. Neuroimaging demonstrated a progressive reduction of intensity and size of lesions in the brainstem and olfactory bulbs, which is observable after the first two weeks of treatment. In late-stage disease mice, the IV ventricle appears more diffuse, likely as a consequence of parenchymal atrophy. This abnormal imaging morphology is reversed upon hypoxia treatment. The aforementioned disease pattern was reversed in all four mice that were studied.

The initial cohort of hypoxia-treated mice remained alive at 170 days of age. Hypoxic exposure was continued to determine the full extent of the survival rescue. 50% survival was observed at 270 days of age. Thus, survival duration of hypoxic rescue treatment was nearly 5-fold that of normoxic KO mice, however it was not a complete rescue relative to wild-type survival. In order to understand the cause of death in this cohort, we began by studying the neurological status of the old, hypoxia-treated mice to determine whether the original disease had manifested.

Figure 23:
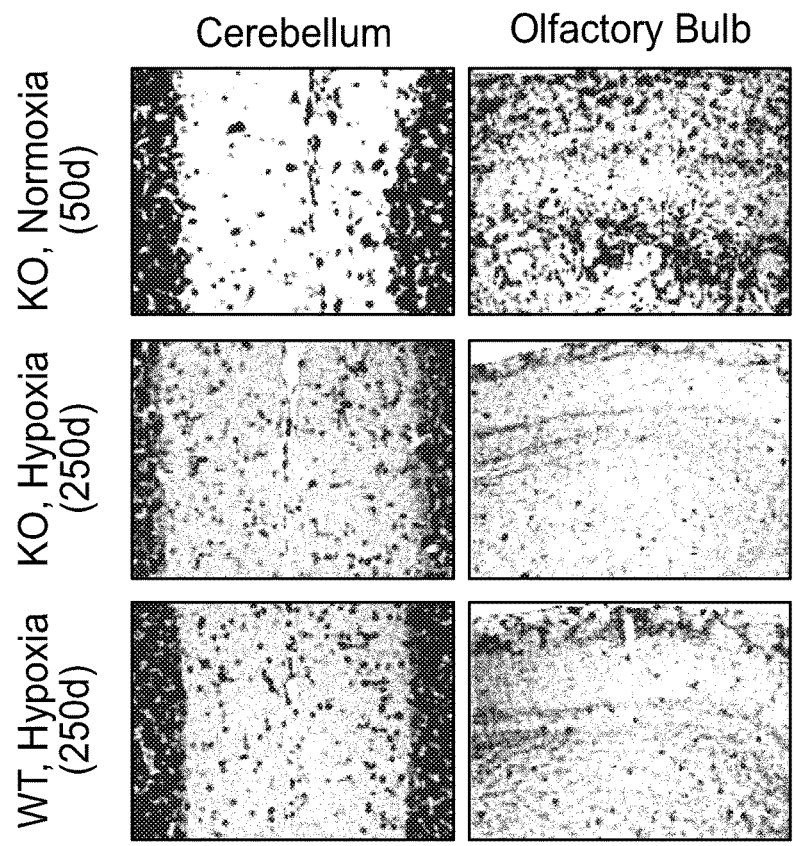
FIGS. 23A-B are a series of photographs showing the absence of neurodegenerative pathology in 250 day old hypoxia-treated Ndufs4 KO mice. (A) Representative images with staining of the microglial activation marker, Iba-1. Normoxic breathing Ndufs4 KO mice at 50 days have a significant inflammatory response in the cerebellum and olfactory bulb. Analogous images in 250 day old hypoxic Ndufs4 KO mice and WT mice do not show brain inflammation. (B) Axial MRI head scans showing bilateral, symmetric hyperintense lesions in the vestibular nucleus and olfactory bulbs of normoxic Ndufs4 KO mice. These lesions were not present in chronically hypoxic Ndufs4 KO mice at 250 days of age.
Figure 23:
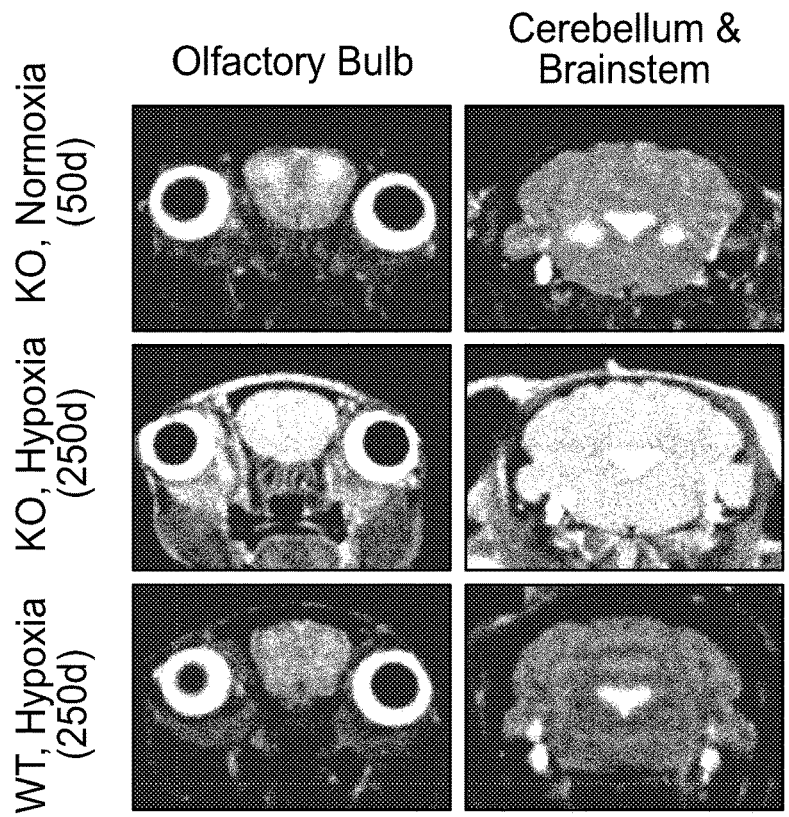

Immunostaining for the inflammatory marker Iba-1 was performed to determine whether hypoxia delays death by delaying neuropathology. Both the cerebellum and olfactory bulb display significant microglial activation in sick, normoxic KO mice. However, none of the hypoxia-treated mice that were greater than 200 days of age displayed any evidence of neuroinflammation by histopathology (FIG. 23A). T2-weighted MRI imaging was also performed to detect the neurological lesions. Mice breathing normoxia at 60 days developed lesions in the postero-lateral portion of the brainstem, localized in the vestibular nuclei (FIG. 23B). These anatomical areas are closely connected to the respiratory center and are responsible for the loss of balance and for overcoming central respiratory failure, typically a terminal event. However, none of the older, hypoxia-treated mice had neurological lesions that were detectable by MM. Thus, hypoxia appears to reverse neurological lesions as detected by Mill and histopathology, even at greater than 200 days of age. This suggests that death in old, hypoxia-treated KO mice is likely to be attributable to other organ dysfunction (e.g., myocardial failure).

Figure 24:
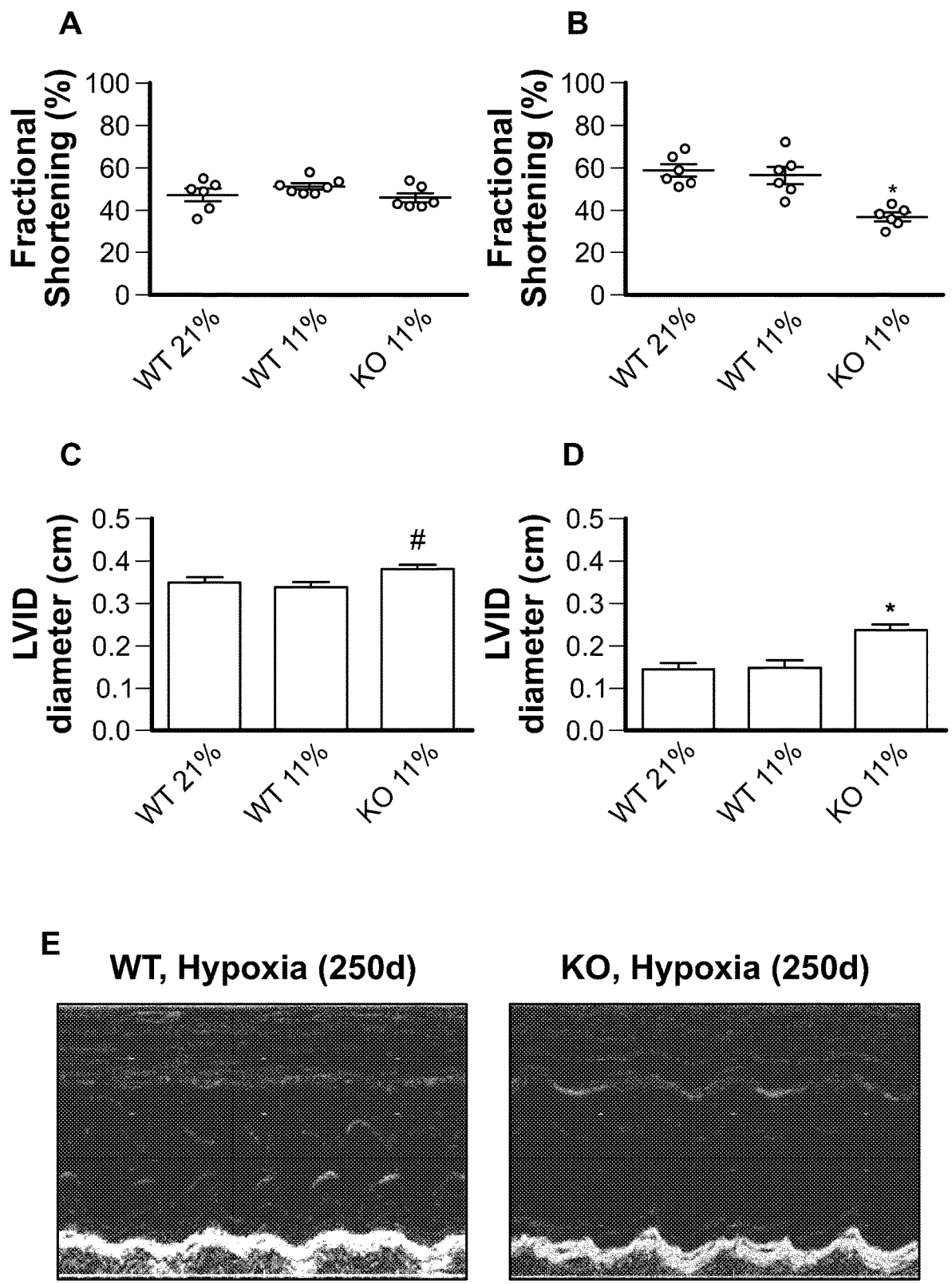
FIGS. 24A-E show depressed myocardial function in Ndufs4 KO mice breathing 11% 02 at 250 days. (A) Left ventricular fractional shortening (FS %) of six mice breathing different oxygen concentrations at 50 days of age. (B) FS % of six mice breathing various oxygen concentrations at 250 days of age. (C) Left ventricular cavity interior diastolic diameter (LVID) at 250 days of age. (D) Left ventricular interior systolic diameter (LVIS) of six mice at 250 days of age. (E) Representative M-mode scans of the left ventricle in WT and KO mice breathing 11% 02 at 250 days. Scans were obtained during light sedation with isoflurane while breathing 21% 02. Data mean±SE; *p<0.05 vs WT; # p<0.05 vs WT 11%.

Cardiomyopathy is a common presentation of mitochondrial disease. The acute nature of death in the old, hypoxia-treated mice suggested that cardiac dysfunction may play a role in the pathology. A series of echocardiograms was obtained during air breathing to investigate the cause of death in 250 day-old Ndufs4 KO mice breathing hypoxia. Using high-resolution ultrasound, LV myocardial contractility was studied and found to be significantly impaired in older, KO mice treated with chronic hypoxia but not in WT controls treated with chronic hypoxia. LV Fractional shortening was 37% versus 60% in WT controls (FIG. 24B). In addition, echocardiograms were strongly suggestive of chronic pericardial effusions and numerous arrhythmias were noted during the scans. Of note, the right ventricle did not appear hypertrophied. However, measurement of left ventricular internal diameters showed enlarged left ventricular lumens both in systole and diastole (FIG. 24C-E). To determine whether such findings are present at an earlier stage in Ndufs4 KO mice breathing 11% oxygen, the same exam was performed at 50 days of age (after about 3 weeks of hypoxia exposure). No alteration of LV contractility was detected at this stage (FIG. 24A). This highlights that the pathologic LV cardiac dysfunction observed in old Ndufs4 KO mice breathing hypoxia was not present in the younger mice breathing normoxia. Indeed, it was preceded by lethal neurologic disease. This suggests that different tissues have altered temporal and oxygen level thresholds for producing oxygen toxicity.

Figures 1, 25:
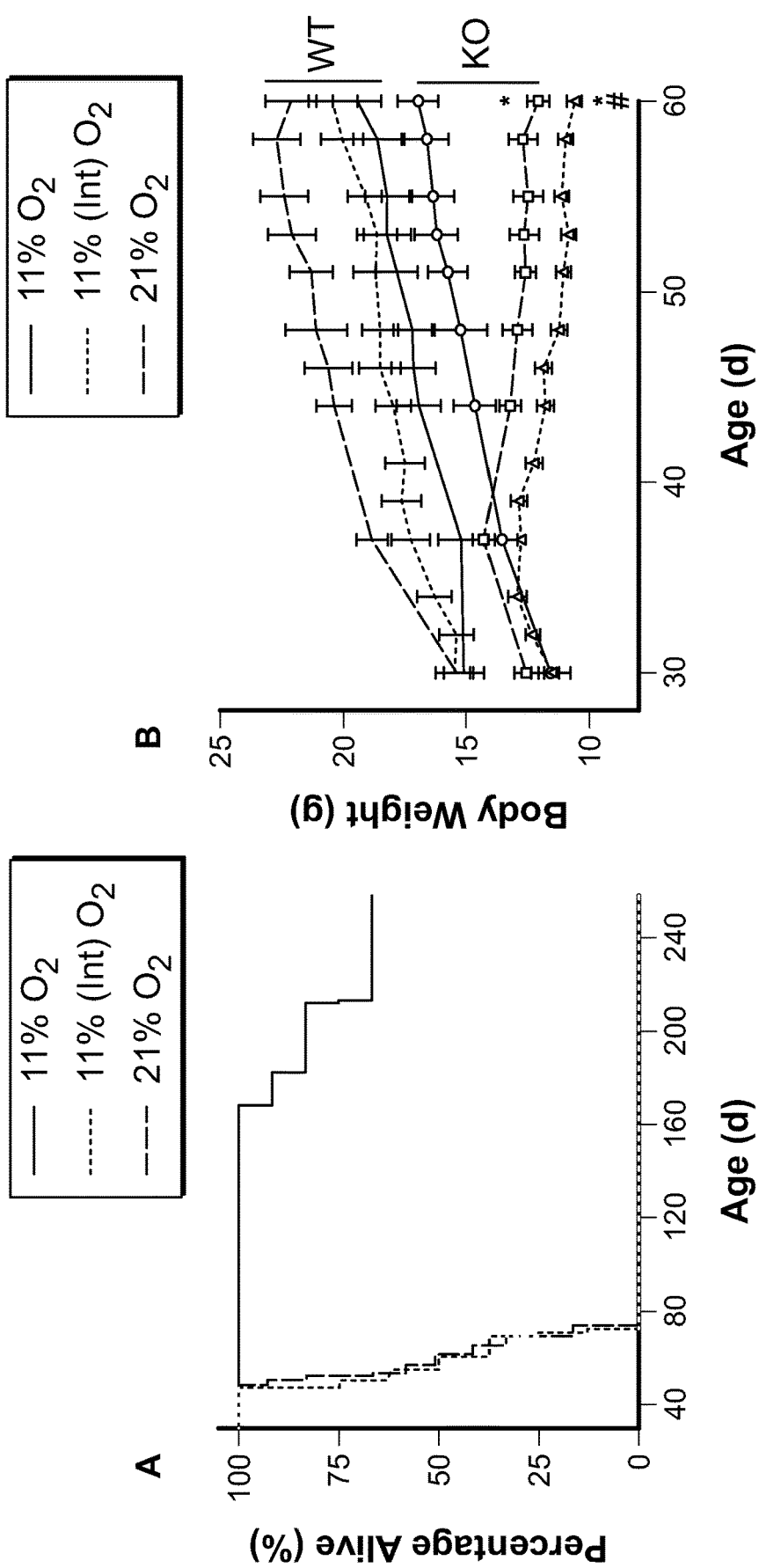
Figures 2, 25:
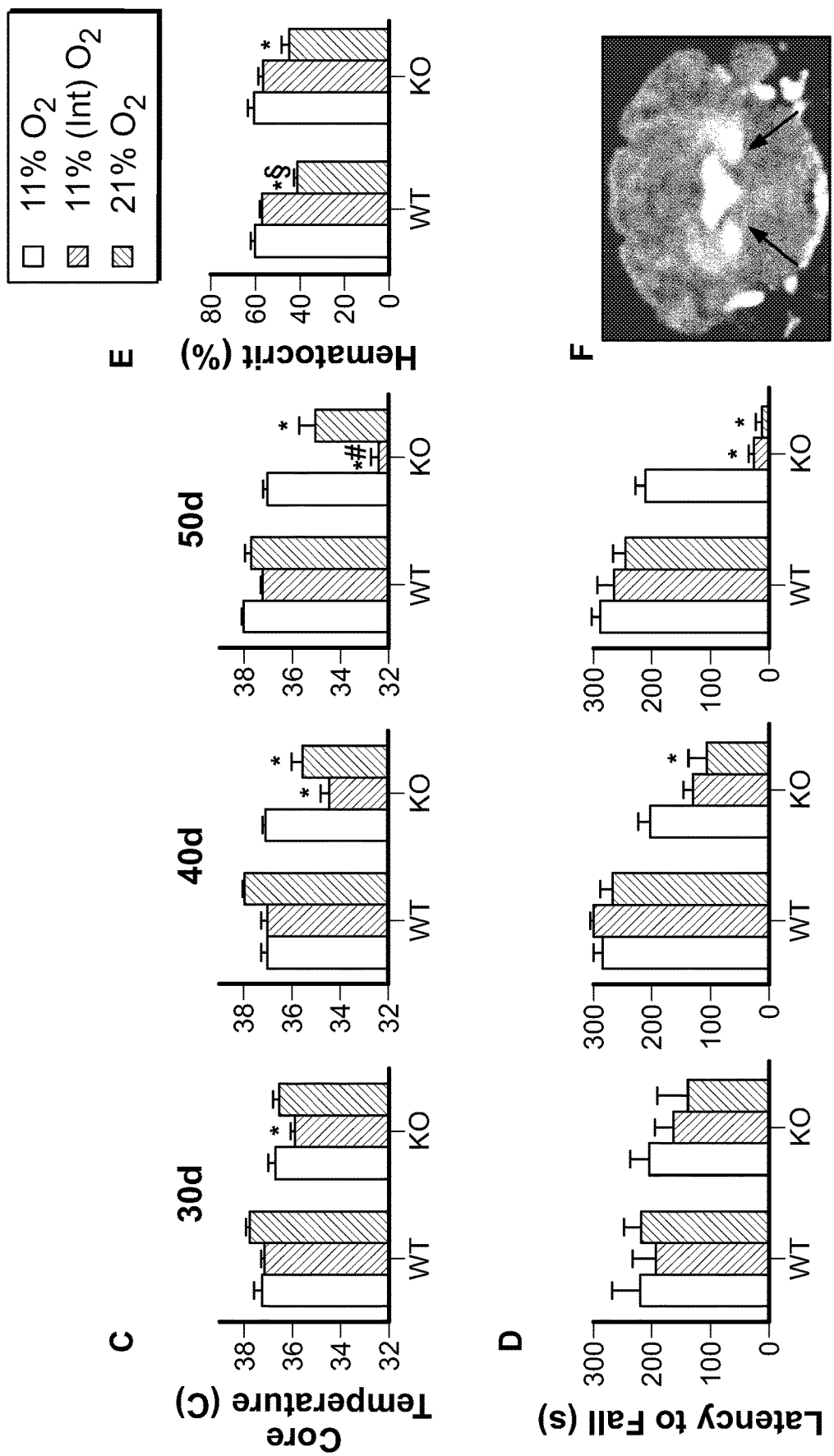

Ndufs4 KO mice were assessed breathing 11% oxygen for ten hours per day from 9 am to 7 pm, and breathing at normoxia for the remaining 14 hours/day. Given that mice are nocturnal creatures, in this protocol they were breathing normoxia while awake and hypoxia while asleep. This intermittent exposure to hypoxia increased hematocrit to 55% within three weeks, indicative of sufficient physiological adaptation to hypoxia (FIG. 25-2E). However, survival rates were identical to untreated (normoxic) KO mice (FIG. 25-1A). During exposure to intermittent hypoxia, body weight decreased until either a natural death or humane euthanasia was administered. Mice undergoing the intermittent protocol presented at 60 days with a lower body weight compared to normoxic KO controls (FIG. 25-1B). Furthermore, body temperature was 32° C. in mice treated with intermittent hypoxia, versus 35° C. of normoxic KO controls (FIG. 25-2C). The ability of KO mice to remain on an accelerating, rotating rod was tested. No significant improvement was recorded when comparing KO mice exposed to intermittent hypoxia vs. normoxia (FIG. 25-2D). All MM scans of Ndufs4 KO mice exposed to intermittent hypoxia revealed hyperintense lesions in the brainstem and olfactory bulbs, resembling the neurological lesions of Ndufs4 KO mice breathing normoxia (FIG. 25-2F). Thus, although this regimen of intermittent hypoxia is sufficient to trigger certain aspects of the hypoxia adaptive program (such as hematocrit elevation), it did not prevent disease progression. In the initial studies of chronic hypoxia described herein, KO mice were briefly exposed to normoxia 3-5 times per week to allow for maintenance of their cages and behavior studies. These mice never developed brain lesions by neuropathology. Thus, some but not all intermittent hypoxia/normoxia regimens are effective.

Figures 1, 26:
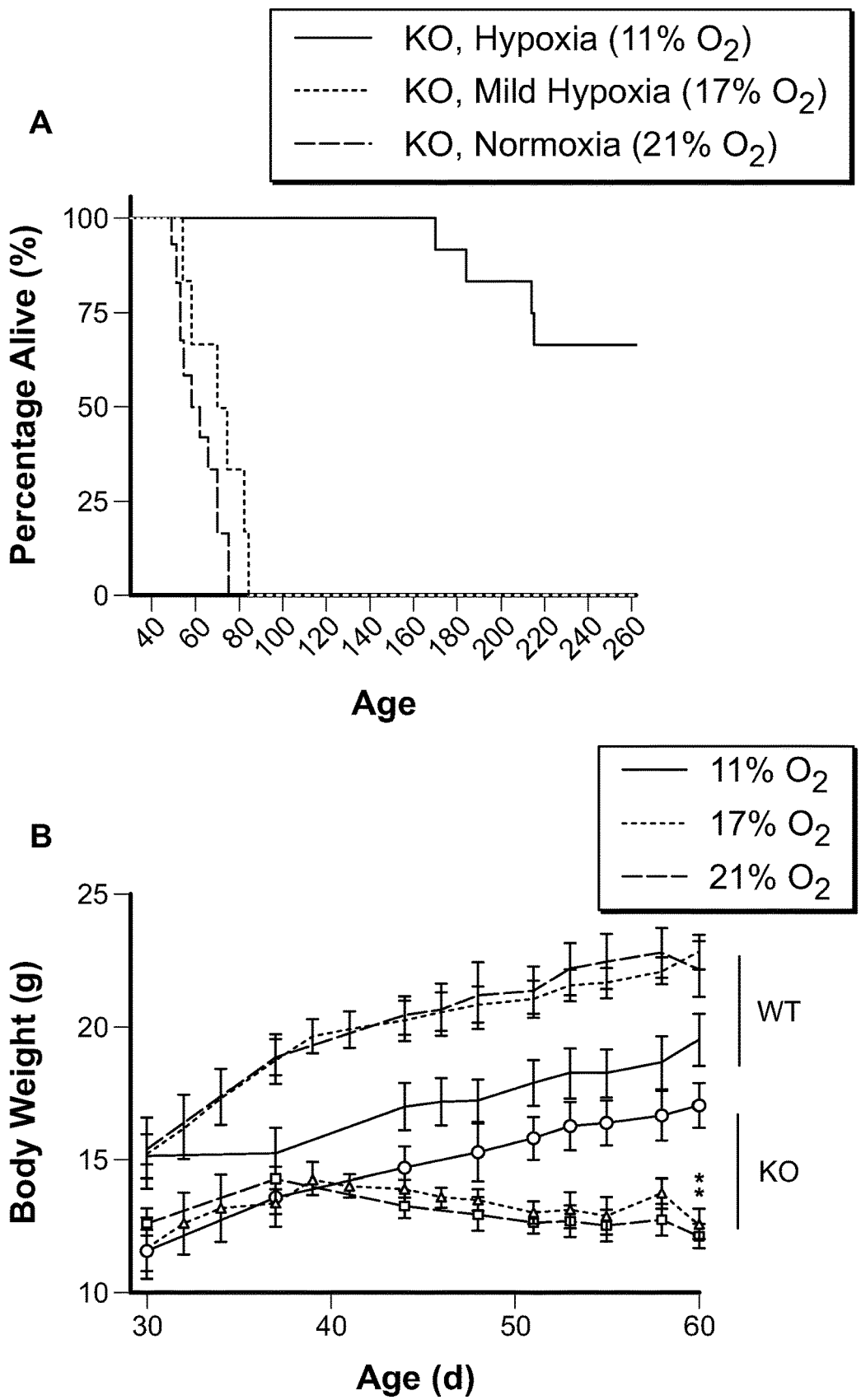
Figures 2, 26:
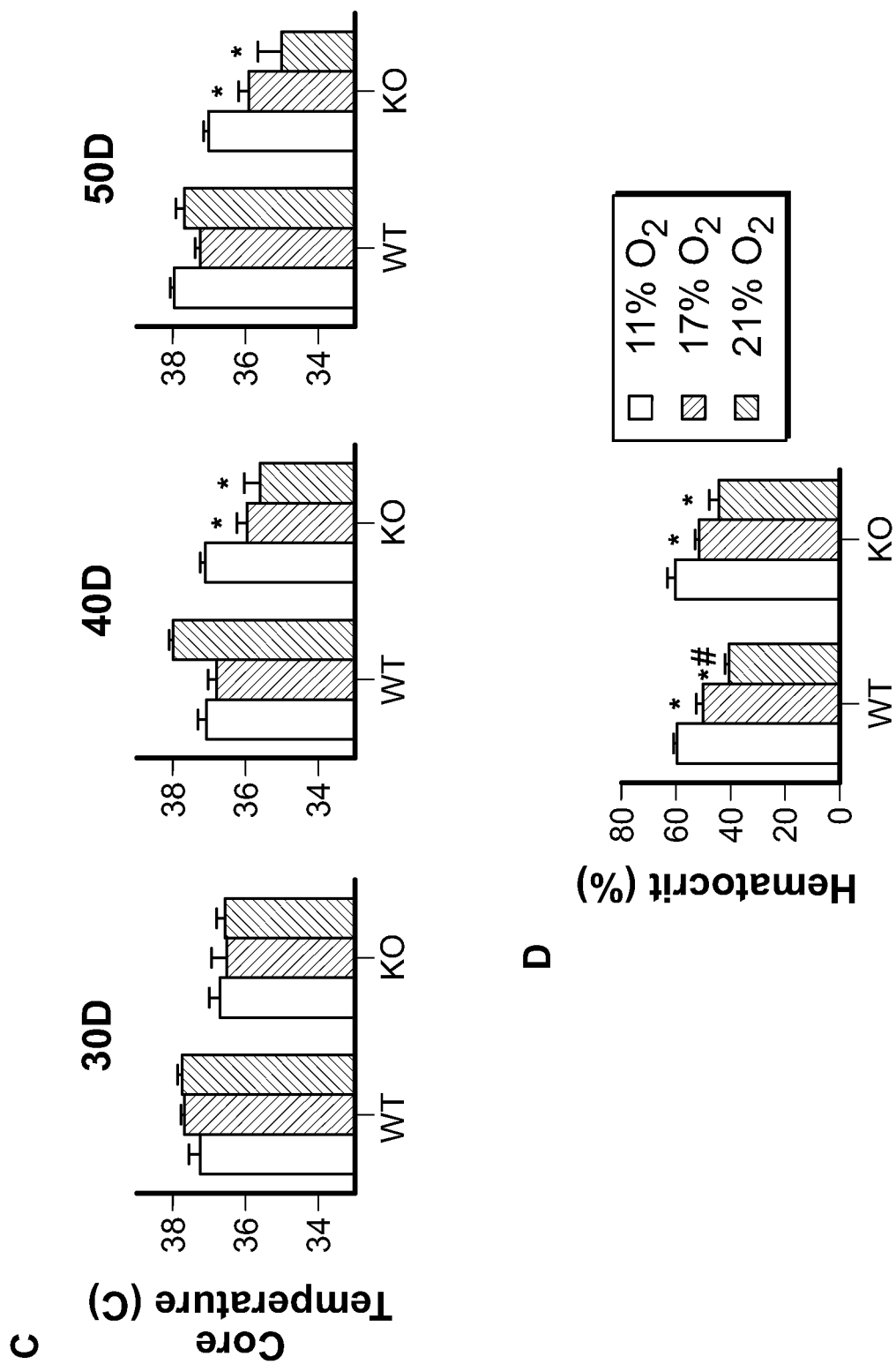

Hypoxic breathing at 11% oxygen is equivalent to breathing the partial pressure of oxygen found at 4,500 m of altitude. A very mild level of hypoxia was also assessed, equivalent to 1,500 m of altitude. Breathing 17% $O_2$ did not prevent neurological disease in Ndufs4 KO mice. The clinical manifestations were similar to Ndufs4 KO mice breathing normoxic air. A loss in body core temperature was recorded from 36.5° C. to 35.9° C. at 50 days of age (FIG. 26-2C). Significant weight loss was also measured (FIG. 26-1B). After 3 weeks of chronic 17% oxygen exposure, the tail venous blood hematocrit was 51% (compared to 60% after three weeks of 11% oxygen exposure) (FIG. 26-2D). These findings suggest that this particular regimen of mild hypoxia is capable of triggering an intermediate physiological response that does not, however, prevent neurological disease progression. In this cohort of mice, the median survival time was increased to 70 days, versus 58 days for normoxic controls, a slight, but statistically insignificant improvement of survival time (FIG. 26-1A).

Example 9: Combination Therapy of Hypoxia and Nitric Oxide

Figure 27:
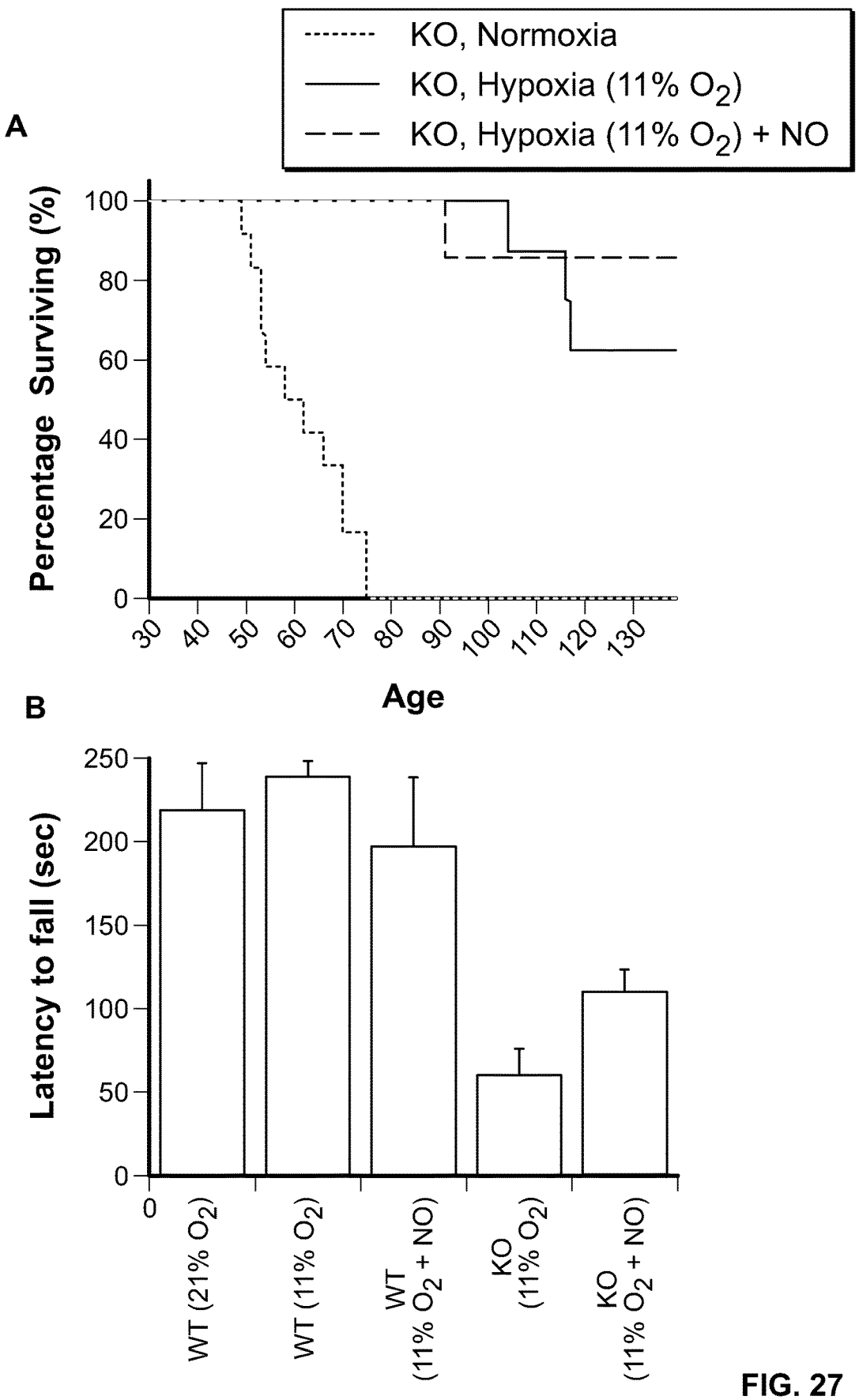
FIGS. 27A-B show that hypoxia and nitric oxide combination therapy improves behavioral performance. (A) Survival curve for Ndufs4 KO mice breathing normoxia, hypoxia or hypoxia combined with low-dose NO (ordering of lines from top to bottom at right side of graph: KO, hypoxia+NO; KO, hypoxia; KO, normoxia). (B) Rotarod test for muscle and grip strength in WT and KO mice exposed to normoxia or hypoxia, with or without nitric oxide. Data mean±SE.

High altitudes and chronic hypoxia exposure are known to cause hypoxic pulmonary vasoconstriction (HPV), which ultimately leads to increased pulmonary arterial pressure and vascular remodeling. Over time, this can result in right ventricular hypertrophy and affect myocardial function. Nitric oxide has a known vasodilatory effect and has previously been shown to decrease human HPV. Nitric Oxide is also a known anti-inflammatory molecule by many pathways and removes superoxide. Mice exposed to breathing a gas mixture of 11% oxygen and low-dose (20-40 ppm) nitric oxide survived significantly longer than normoxia treated mice (FIG. 27A). Mice exposed to hypoxia are able to remain on the rotating rod longer than normoxia treated mice (FIG. 27B). Initial results suggested that diseased mice treated with a gas mixture of 11% oxygen, combined with low-dose nitric oxide perform even better than just hypoxia-treated mice.

Example 10: Hypoxia Protects Against LPS-Toxicity in KO Mice

Mitochondrial disease patients are particularly susceptible to infections. It is believed that that the hyperimmune response of mitochondrial disease patients may contribute to disease pathogenesis. Furthermore, the mouse model of Leigh Syndrome shows a significant inflammatory response in the brain regions that ultimately suffer from neurodegeneration and cause death by respiratory failure. We investigated whether the Ndufs4 KO mouse model demonstrated increased susceptibility to infection, using LPS as the immune trigger.

Figure 28:
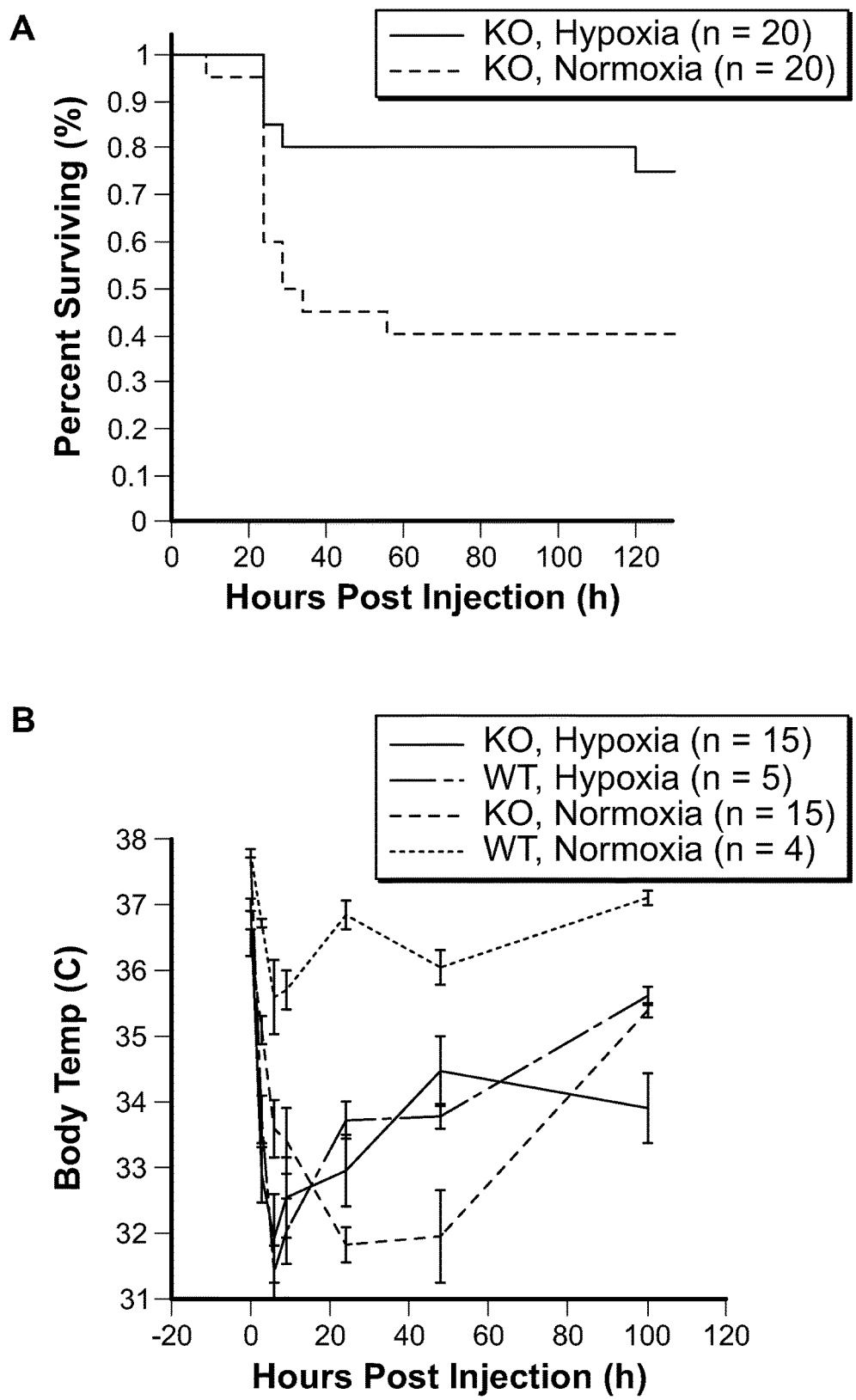
FIGS. 28A-B show that hypoxia is protective against low-dose LPS sensitivity of Ndufs4 KO mice. (A) Survival curve for Ndufs4 KO mice breathing hypoxia or normoxia after i.p. injection of LPS (5 mg/kg), a well-tolerated dose in WT mice (ordering of lines from top to bottom at right side of graph: KO, hypoxia; KO, normoxia). (B) Core temperature in WT and KO mice exposed to either hypoxia or normoxia after low-dose LPS injection (ordering of lines from top to bottom at right side of graph: WT, normoxia; WT, hypoxia; KO, normoxia; KO, hypoxia).

A low dose of LPS, which is completely benign to WT mice, was extremely toxic to Ndufs4 KO mice (FIG. 28A). No deaths were observed in WT animals within the first few days following LPS injection (5 mg/kg), however a nearly 70% death rate was apparent in Ndufs4 KO mice in the same time. Of note, LPS injections were given at a young age to WT and KO mice, before the typical disease symptoms are apparent in the Ndufs4 KO mice. Thus, the increased sensitivity to LPS is not attributable to a terminal decline in health status.

In order to further understand the mechanism by which hypoxia rescues disease symptoms, we investigated whether hypoxia protects against the pathology associated with the hyperimmune response in KO mice. Indeed, acute hypoxic exposure of LPS-treated KO mice improved survival duration nearly 3-fold (FIG. 28A). Body temperature loss upon LPS treatment was not significantly rescued by hypoxia treatment, as hypoxia itself causes acute changes in body temperature in both WT and KO mice (FIG. 28B). This finding indicates that the therapeutic effects of hypoxia may involve an ability to suppress the toxic effects of the hyperimmune response in mitochondrial disease mice. As the inflammatory response involves a significant oxidative stress component, this is a prime example of the therapeutic effect of hypoxia in the setting of an oxidative stress pathology.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or preventing mitochondrial dysfunction in a subject in need thereof, the method comprising administering to the subject by inhalation continuously for at least two hours a therapeutically effective amount of a therapeutic gas comprising between 5 to 20% $O_2$.

2. The method of claim 1, wherein the subject has a mitochondrial disorder.

3. The method of claim 2, wherein the mitochondrial disorder is a monogenic mitochondrial disorder.

4. The method of claim 3, wherein the mitochondrial disorder is characterized by a mutation in a gene selected from the group consisting of AARS2, AASS, ABAT, ABCB6, ABCB7, ABCD1, ACACA, ACAD8, ACAD9, ACADM, ACADS, ACADSB, ACADVL, ACAT1, ACO2, ACSF3, ACSL4, ADCK3, ADCK4, AFG3L2, AGK, AGXT, AIFM1, AK2, ALAS2, ALDH18A1, ALDH2, ALDH3A2, ALDH4A1, ALDH5A1, ALDH6A1, ALDH7A1, AMACR, AMT, APOPT1, ATIC, ATP5A1, ATP5E, ATP6, ATP5, ATPAF2, ATXN2, AUH, BAX, BCKDHA, BCKDHB, BCKDK, BCS1L, BOLA3, C10orf2, C12orf65, CA5A, CARS2, CASP8, CAT, CEP89, CHCHD10, CISD2, CLPB, CLPP, COA5, COA6, COASY, COQ2, COQ4, COQ6, COQ9, COX1, COX10, COX14, COX15, COX2, COX20, COX3, COX4I2, COX6A1, COX6B1, COX7B, CPDX, CPS1, CPT1A, CPT2, CYB5A, CYB5R3, CYC1, CYCS, CYP11A1, CYP11B2, CYP24A1, CYP27A1, CYP27B1, CYTB, D2HGDH, DARS2, DBT, DGUOK, DHCR24, DHODH, DHTKD1, DIABLO, DLAT, DLD, DMGDH, DMPK, DNA2, DNAJC19, DNM1L, EARS2, ECHS1, ELAC2, ETFA, ETFB, ETFDH, ETHE1, FARS2, FASTKD2, FBXL4, FECH, FH, FKBP10, FOXRED1, FXN, GARS, GATM, GCDH, GCSH, GDAP1, GFER, GFM1, GK, GLDC, GLRX5, GLUD1, GLYCTK, GPI, GPX1, GRHPR, GTPBP3, HADH, HADHA, HADHB, HARS2, HCCS, HIBCH, HK1, HMBS, HMGCL, HMGCS2, HOGA1, HSD17B10, HSD17B4, HSPD1, HTRA2, IDH2, IDH3B, ISCA2, ISCU, IVD, KARS, KIF1B, KRT5, L2HGDH, LARS2, LIAS, LONP1, LRPPRC, LYRM4, LYRM7, MAOA, MARS2, MCCC1, MCCC2, MCEE, MFN2, MGME1, MICU1, MLH1, MLYCD, MMAB, MMACHC, MMADHC, MOCS1, MPC1, MPV17, MRPL12, MRPL3, MRPL44, MRPS16, MRPS22, mt-12S rRNA, mt-tRNATyr, mt-tRNATrp, mt-tRNAVal, mt-tRNAThr, mt-tRNASer1, mt-tRNASer2, mt-tRNAArg, mt-tRNAGln, mt-tRNAPro, mt-tRNAAsn, mt-tRNAMet, mt-tRNALeu1, mt-tRNALeu2, mt-tRNALys, mt-tRNAIle, mt-tRNAHis, mt-tRNAGly, mt-tRNAPhe, mt-tRNAGlu, mt-tRNAAsp, mt-tRNACys, mt-tRNAAla, MTFMT, MTO1, MTPAP, MUT, MUTYH, NAGS, NARS2, NCOA4, ND1, ND2, ND3, ND4, ND4L, ND5, ND6, NDUFA1, NDUFA10, NDUFA11, NDUFA12, NDUFA2, NDUFA4, NDUFA9, NDUFAF1, NDUFAF2, NDUFAF3, NDUFAF4, NDUFAF5, NDUFAF6, NDUFB11, NDUFB3, NDUFB9, NDUFS1, NDUFS2, NDUFS3, NDUFS4, NDUFS6, NDUFS7, NDUFS8, NDUFV1, NDUFV2, NFU1, NNT, NUBPL, OAT, OGDH, OGG1, OPA1, OPA3, OTC, OXCT1, PAM16, PANK2, PARK7, PARS2, PC, PCCA, PCCB, PCK2, PDHA1, PDHB, PDHX, PDP1, PDSS1, PDSS2, PET100, PEX11B, PEX6, PHYH, PINK1, PNPO, PNPT1, POLG, POLG2, PPM1K, PPOX, PRODH, PTRH2, PTS, PUS1, PYCR1, QDPR, RARS, RARS2, RMND1, RPL35A, RPS14, RRM2B, SARS2, SCO1, SCO2, SCP2, SDHA, SDHAF1, SDHAF2, SDHB, SDHC, SDHD, SECISBP2, SERAC1, SFXN4, SLC16A1, SLC19A3, SLC25A1, SLC25A12, SLC25A13, SLC25A15, SLC25A19, SLC25A20, SLC25A22, SLC25A3, SLC25A38, SLC25A4, SNAP29, SOD1, SPG7, SPR, SPTLC2, STAR, SUCLA2, SUCLG1, SUOX, SURF1, TACO1, TARS2, TAZ, TCIRG1, TIMM8A, TK2, TMEM126A, TMEM70, TMLHE, TPI1, TRIT1, TRMU, TRNT1, TSFM, TTC19, TUBB3, TUFM, TYMP, UNG, UQCR10, UQCRB, UQCRC2, UQCRQ, VARS2, WDR81, WFS1, XPNPEP3, and YARS2.

5. The method of claim 2, wherein the mitochondrial disorder is characterized by a point mutation in the mitochondrial DNA (mtDNA), deletion within the mtDNA, duplication within the mtDNA, or depletion of the mtDNA.

6. The method of claim 2, wherein the mitochondrial disorder is characterized by a biochemical deficiency of respiratory chain Complex I, II, III, IV, V, or a combination thereof.

7. The method of claim 2, wherein the mitochondrial disorder is Kearns-Sayre syndrome (KSS), Leber's hereditary optic neuropathy (LHON), myoclonic epilepsy ragged red fiber syndrome (MERRF), mitochondrial encephalopathy, lactic acidosis, and stroke (MELAS) syndrome, sensory ataxic neuropathy, dysarthria, and ophthalmoparesis (SANDO) syndrome, maternally inherited Leigh syndrome (MILS), myopathy and external ophthalmoplegia, neuropathy, gastrointestinal encephalopathy (MNGIE) syndrome, Leigh syndrome, maternally inherited diabetes and deafness (MIDD) syndrome, Alpers-Huttenlocher syndrome, Sengers syndrome, mitochondrial myopathy, lactic acidosis and sideroblastic anemia (MLASA), chronic progressive external ophthalmoplegia (CPEO), autosomal dominant progressive external ophthalmoplegia (AdPEO), neuropathy, ataxia, retinitis pigmentosa (NARP) syndrome, GRACILE syndrome, diabetes insipidus, diabetes mellitus, optic atrophy, and deafness (DIDMOAD) syndrome, or Pearson's syndrome.

8. The method of claim 1, wherein the subject has an age-associated disorder.

9. The method of claim 8, wherein the age-associated disorder is type 2 diabetes, insulin resistance, neurodegeneration, peripheral neuropathy, sarcopenia, muscle atrophy, deafness, atherosclerosis, cardiovascular disease, heart failure, chronic kidney disease, cancer, arthritis, cataracts, or osteoporosis.

10. A method of treating or preventing an oxidative stress disorder in a subject in need thereof, the method comprising administering to the subject by inhalation continuously for at least two hours a therapeutically effective amount of a therapeutic gas comprising between 5 to 20% $O_2$.

11. The method claim 10, wherein the oxidative stress disorder is Parkinson's disease, Alzheimer's disease, amyotrophic lateral sclerosis, Huntington's disease, multiple sclerosis, Asperger syndrome, attention deficit hyperactivity disorder, diabetes, cardiovascular disease, cancer, Lafora disease, atherosclerosis, heart failure, myocardial infarction, fragile X syndrome, sickle cell disease, lichen planus, vitiligo, or autism.

12. The method of claim 1, wherein the therapeutic gas is administered to the subject by inhalation continuously for at least four hours.

13. The method of claim 10, wherein the therapeutic gas is administered to the subject by inhalation continuously for at least four hours.

14. The method of claim 1, wherein the therapeutic gas is administered to the subject by inhalation continuously for at least eight hours.

15. The method of claim 10, wherein the therapeutic gas is administered to the subject by inhalation continuously for at least eight hours.

16. The method of claim 1, wherein the therapeutic gas is administered to the subject by inhalation continuously for at least 12 hours.

17. The method of claim 10, wherein the therapeutic gas is administered to the subject by inhalation continuously for at least 12 hours.

18. The method of claim 1, wherein the therapeutic gas is administered to the subject by inhalation continuously for at least 24 hours.

19. The method of claim 10, wherein the therapeutic gas is administered to the subject by inhalation continuously for at least 24 hours.

20. The method of claim 1, wherein the therapeutic gas is administered to the subject by inhalation continuously for at least 48 hours.

21. The method of claim 10, wherein the therapeutic gas is administered to the subject by inhalation continuously for at least 48 hours.

22. The method of claim 1, wherein the therapeutic gas comprises between 10 to 15% $O_2$.

23. The method of claim 1, wherein the therapeutic gas comprises between 10 to 12% $O_2$.

24. The method of claim 1, wherein the therapeutic gas comprises about 11% $O_2$.

25. The method of claim 10, wherein the therapeutic gas comprises between 10 to 15% $O_2$.

26. The method of claim 10, wherein the therapeutic gas comprises between 10 to 12% $O_2$.

27. The method of claim 10, wherein the therapeutic gas comprises about 11% $O_2$.

28. The method of claim 1, wherein the therapeutic gas comprises nitric oxide.

29. The method of claim 28, wherein the concentration of nitric oxide in the therapeutic gas is in the range of 0.5 ppm to 80 ppm.

30. The method of claim 1, wherein the therapeutic gas comprises xenon.

31. The method of claim 30, wherein the therapeutic gas comprises between 20-70% xenon.

32. The method of claim 10, wherein the therapeutic gas comprises nitric oxide.

33. The method of claim 32, wherein the concentration of nitric oxide in the therapeutic gas is in the range of 0.5 ppm to 80 ppm.

34. The method of claim 10, wherein the therapeutic gas comprises xenon.

35. The method of claim 34, wherein the therapeutic gas comprises between 20-70% xenon.

* * * * *

UNITED STATES PATENT AND TRADEMARK OFFICE
CERTIFICATE OF CORRECTION

PATENT NO. : 10,842,812 B2
APPLICATION NO. : 15/751585
DATED : November 24, 2020
INVENTOR(S) : Vamsi K. Mootha et al.

It is certified that error appears in the above-identified patent and that said Letters Patent is hereby corrected as shown below:

In the Specification

In Column 1, Line 11 (approx.), after "application" insert -- is a § 371 National Stage Application of PCT/US2016/046791, filed Aug. 12, 2016, which --

In the Claims

In Column 47, Line 33, in Claim 4, delete "ATP5," and insert -- ATP8, --

In Column 49, Line 6, in Claim 11, after "method" insert -- of --

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*